US009339532B2

(12) United States Patent
Purtle et al.

(10) Patent No.: US 9,339,532 B2
(45) Date of Patent: May 17, 2016

(54) POTOMAC HORSE FEVER ISOLATES

(71) Applicant: Intervet Inc., Summit, NJ (US)

(72) Inventors: Lisa Purtle, Olathe, KS (US); Mark Mellencamp, St. Joseph, MO (US); Wendy Vaala, Alma, WI (US)

(73) Assignee: Intervet Inc., Madison, NJ (US)

( * ) Notice: Subject to any disclaimer, the term of this patent is extended or adjusted under 35 U.S.C. 154(b) by 0 days.

(21) Appl. No.: 14/101,659

(22) Filed: Dec. 10, 2013

(65) Prior Publication Data

US 2014/0186385 A1 Jul. 3, 2014

Related U.S. Application Data

(62) Division of application No. 13/221,356, filed on Aug. 30, 2011, now Pat. No. 8,628,947.

(60) Provisional application No. 61/378,261, filed on Aug. 30, 2010, provisional application No. 61/381,326, filed on Sep. 9, 2010.

(51) Int. Cl.

| | |
|---|---|
| ***A61K 39/02*** | (2006.01) |
| ***G01N 33/569*** | (2006.01) |
| ***C07H 21/04*** | (2006.01) |
| ***C07K 14/29*** | (2006.01) |
| ***C12N 1/20*** | (2006.01) |
| ***C12Q 1/68*** | (2006.01) |
| ***C12Q 1/02*** | (2006.01) |
| ***C12R 1/01*** | (2006.01) |
| *A61K 39/00* | (2006.01) |

(52) U.S. Cl.

CPC .............. *A61K 39/0233* (2013.01); *C12N 1/20* (2013.01); *C12R 1/01* (2013.01); *A61K 2039/521* (2013.01); *A61K 2039/552* (2013.01); *C12Q 1/689* (2013.01); *G01N 2333/29* (2013.01)

(58) Field of Classification Search

None

See application file for complete search history.

(56) References Cited

U.S. PATENT DOCUMENTS

| | | | |
|---|---|---|---|
| 4,578,269 | A | 3/1986 | Morein |
| 4,744,983 | A | 5/1988 | Morein |
| 4,759,927 | A | 7/1988 | Dutta |
| 5,254,339 | A | 10/1993 | Morein |
| 6,375,954 | B1 | 4/2002 | Dutta et al. |
| 2003/0216318 | A1 | 11/2003 | Jaworski et al. |
| 2004/0191262 | A1 | 9/2004 | Dutta et al. |
| 2004/0219163 | A1 | 11/2004 | Frelinger et al. |
| 2005/0123556 | A1 | 6/2005 | Nuttall et al. |
| 2005/0287169 | A1 | 12/2005 | Belitsky |
| 2009/0246233 | A1 | 10/2009 | Devane et al. |

FOREIGN PATENT DOCUMENTS

| | | |
|---|---|---|
| EP | 0528898 | 5/1991 |
| WO | 2007140506 | 12/2007 |

OTHER PUBLICATIONS

Rikihisa (Veterinary Microbiology, vol. 27 No. 3-4, pp. 339-350), 1991.*

NCBI Blast Search—*N. risticii*-ssa2 protein (Oregon strain), dated Nov. 15, 2012.

NCBI Blast Search—*N. risticii*-ssa3 protein (Oregon strain), dated Nov. 15, 2012.

NCI Blast Search—*N. risticii*-ssa1 protein (Oregon strain), dated Nov. 15, 2012.

Colman, "Effects of amino acid sequence changes on antibody-antigen interactions", Research Immunology, 1994, pp. 33-36, vol. 145.

Genbank Accession No. AEK71066, Strain-specific antigen 3 [*Neorickettsia risticii*], dated Jul. 27, 2011.

Gibson, et al., "*Neorickettsia risticii* surface-exposed proteins: proteomics identification, recognition by naturally-infected horses, and strain variations", Veterinary Research, 2011, pp. 1-14, vol. 42(71).

Greenspan, et al., "Defining epitopes: It's not as easy as it seems", Nature Biotechnology, 1999, pp. 936-937, vol. 17.

Lin, et al., "Analysis of complete genome sequence of *Neorickettsia risticii*: causative agent of Potomac horse fever; " Nucleic Acids Research, 2009, pp. 6076-6091, vol. 37(18).

* cited by examiner

*Primary Examiner* — Robert A Zeman

(57) ABSTRACT

The present invention discloses novel isolates of *Neorickettsia risticii*, compositions comprising such isolates, vaccines and methods for using such vaccines against Potomac Horse Fever.

3 Claims, 55 Drawing Sheets

+ Majority

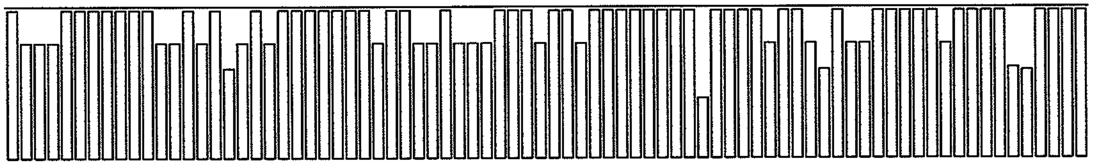

```
Majority                          MSNETLLSVLSDETHFANLVDELLLSLVKDSIFTQVIKGEGKTELKDILTDXTGKFKELIGSSGKDILKSILTDGSGNFK
                                           10        20        30        40        50        60        70        80
N ristìcii_ILLstrain-CP001431     MSNETLLSVLSDETHFANLVDELLLSLVKDSIFTQVIKGEGKTELKDILTDSTGKFKELIGSSGKDILKSILTDGSGNFK 80
N risticii_Oregon                 MPGDTLLSVLSNDTYFSSLTDELLLSLIKDTVFNGMIKGDGKIELKDILTDNTGKFRELVESSSKDILKSILTDSTGNFK 80
N risticii_25D                    MSNETLLSVLSDETHFANLVDELLLSLVKDSIFTQVIKGEGKTELKDILTDNTGKFKELIGSSGKDILKSILTDGSGNFK 80
N risticii_90-12                  MSNETLLSVLSDETHFNNLVDELLLSLVKDSIFTQVIKGEGKTELKDILTDNTGKFKELIESAGKDILKEILTDNTGNFK 80
N risticii_Michigan               MSNETLLSVLSDETHFNNLVDELLLSLVKDSIFTQVIKGEGKTELKDILTDNTGKFKELIGSSGKDILKSILTDGSGNFK 80
N risticii_New York               MSNETLLSVLSDETHFANLVDELLLSLVKDSIFTQVIKGEGKTELKDILTDSTGKFKELIGSSGKDILKSILTDGSGNFK 80
```

FIG. 4A-1

Decoration 'Decoration #1': Box residues that differ from the Consensus.

+ Majority

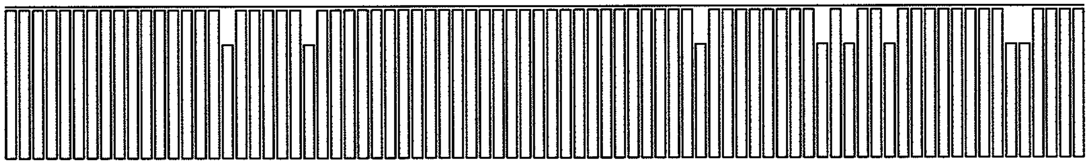

Majority MTDDTLLSVLSNETHFNNLIDEFLLSLVKDAMFNQVIKGEGKTELKDILTDTTGKFKELIGGSGKAILKSILTDNTGNFK 10 20 30 40 50 60 70 80

N risticii_ILLstrain-CP001431 MTDDTLLSVLSNETHFNNLIDEFLLSLVKDAMFNQVIKGEGKTELKDILTDTTGKFKELIGGSQKAILKSILTDNTGNFK 80
N risticii_New York MTDDTLLSVLSNETHFNNLIDEFLLSLVKDAMFNQVIKGEGKTELKDILTDTTGKFKELIGGSGKAILKSILTDNTGNFK 80
N risticii_90-12 MTDDTLLSVLSNETHFNNLIDEFLLSLVKDAMFNQVIKGEGKTELKDILTDTTGKFKELIGGSGKAILKSILTDNTGNFK 80
N risticii_25D MTDDTLLSVLSNETHFNNLIDEFLLSLVKDAMFNQVIKGEGKTELKDILTDTTGKFKELIGGSGKAILKSILTDNTGNFK 80
N risticii_Oregon MTDDTLLSVLSNETHFSNLIDESLLSLVKDAMFNQVIKGEGKTELKDILTDSTGKFKELIEGTGKDILKSILTDGSGNFK 80
N risticii_Michigan MTDDTLLSVLSNETHFNNLIDEFLLSLVKDAMFNQVIKGEGKTELKDILTDTTGKFKELIGGSGKAILKSILTDNTGNFK 80

FIG.5A-1

+ Majority

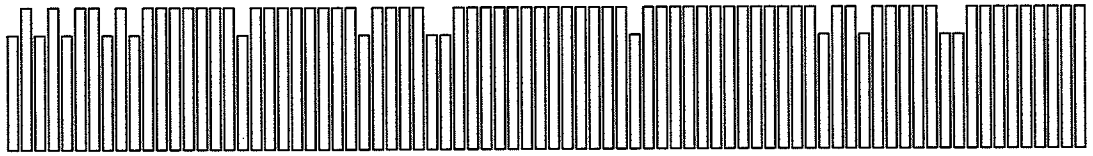

```
Majority                          ALIEGNGKTQAKEVLTHEKFKELFSTADRAGIAKEVLTAEQFEKLLKGSGKTQAKEVLTNENFNKLFDTTSSAKIAKEVL
                                          90        100       110       120       130       140       150       160

N risticii_ILLstrain-CP001431     ALIEGNGKTQAKEVLTHEKFKELFSTADRAGIAKEVLTAEQFEKLLKGSGKTQAKEVLTNENFNKLFDTTSSAKIAKEVL 160
N risticii_New York               ALIEGNGKTQAKEVLTHEKFKELFSTADRAGIAKEVLTAEQFEKLLKGSGKTQAKEVLTNENFNKLFDTTSSAKIAKEVL 160
N risticii_90-12                  ALIEGNGKTQAKEVLTHEKFKELFSTADRAGIAKEVLTAEQFEKLLKGSGKTQAKEVLTNENFNKLFDTTSSAKIAKEVL 160
N risticii_25D                    ALIEGNGKTQAKEVLTHEKFKELFSTADRAGIAKEVLTAEQFEKLLKGSGKTQAKEVLTNENFNKLFDTTSSAKIAKEVL 160
N risticii_Oregon                 GLMESNGRTEAKEVLTHGKFKELFSTSDRAGVTKEVLYAEQFEKLLEGSGKTQAKEVLTNKNFKKLFDTADSAKIAKEVL 160
N risticii_Michigan               ALIEGNGKTQAKEVLTHEKFKELFSTADRAGIAKEVLTAEQFEKLLKGSGKTQAKEVLTNENFNKLFDTTSSAKIAKEVL 160
```

FIG.5A-2

+ Majority

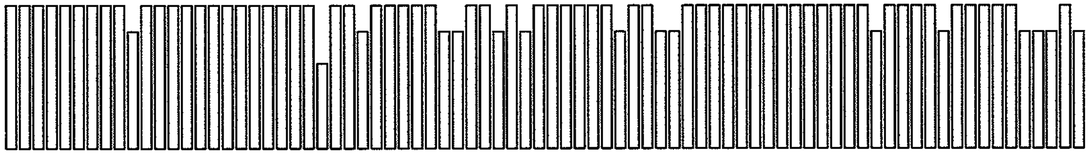

Majority TAEQFEKLLKGSGKTQAKEVLTNENFNKLFDTTGSADIAKEVLTAEQFEKLLKGSGKTQAKEVLTNENFNKLFDTTGSAD 170 180 190 200 210 220 230 240

N risticii_ILLstrain-CP001431 TAEQFEKLLKGSGKTQAKEVLTNKNFNKLFDTTGSADIAKEVLTAEQFEKLLKGSGKTQAKEVLTNENFNKLFDTTGSAD 240
N risticii_New York TAEQFEKLLKGSGKTQAKEVLTNENFNKLFDTTGSADIAKEVLTAEQFEKLLKGSGKTQAKEVLTNENFNKLFDTTGSAD 240
N risticii_90-12 TAEQFEKLLKGSGKTQAKEVLTNKNFNKLFDTTGSADIAKEVLTAEQFEKLLKGSGKTQAKEVLTNENFNKLFDTTGSAD 240
N risticii_25D TAEQFEKLLKGSGKTQAKEVLTNENFNKLFDTTGSADIAKEVLTAEQFEKLLKGSGKTQAKEVLTNENFNKLFDTTGSAD 240
N risticii_Oregon TAEQFEKLLEGSGKTQAKEVLTNENFKKLFDTADSAGIVKEVLTAQQFKQLLKGSGKTQAKEVLINENFNSLFDTADRAG 240
N risticii_Michigan TAEQFEKLLKGSGKTQAKEVLTNENFNKLFDTTGSADIAKEVLTAEQFEKLLKGSGKTQAKEVLTNENFNKLFDTTGSAD 240

FIG.5A-3

+ Majority 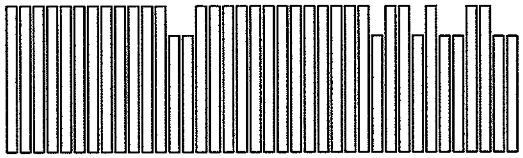

```
Majority                            ISELKDLIHGEDGKHEEKLKAFGDKLKEAKTPDSKKKN-
                                               490       500       510

N risticii_ILLstrain-CP001431       ISELKDLIHCEDGKHEEKLKAFGDKLKEAKTPDSKKKN.
N risticii_New York                 ISELKDLIHCEDGKHEEKLKAFGDKLKEAKTPDSKKKN.
N risticii_90-12                    ISELKDLIHCEDGKHEEKLKAFGDKLKEAKTPDSKKKN.
N risticii_25D                      ISELKDLIHCEDGKHEEKLKAFGDKLKEAKTPDSKKKN.
N risticii_Oregon                   ISELKDLIHCEDSQHEEKLKAFGDKLKKAKNPNQKKEK.
N risticii_Michigan                 ISELKDLIHCEDGKHEEKLKAFGDKLKEAKTPDSKKKN.
```

Decoration 'Decoration #1': Box residues that differ from the Consensus.

FIG.5C

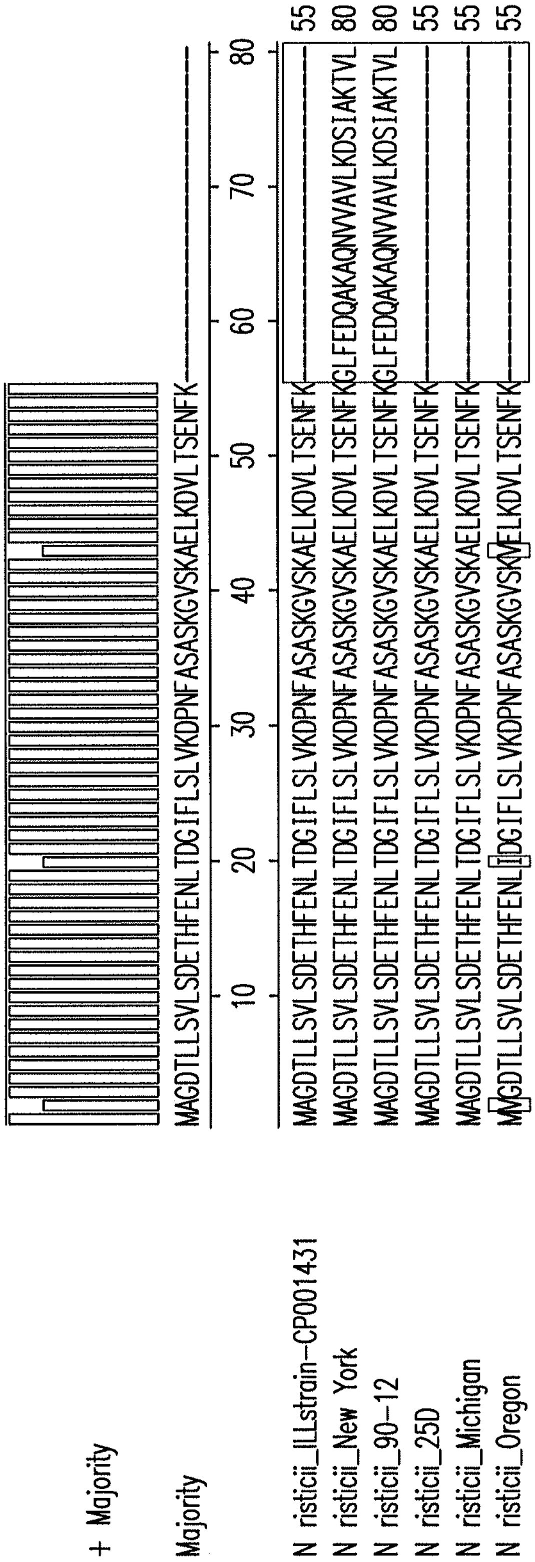

FIG.6A-1

```
                    MAGDTLLSVLSDETHFENLTDGIFLSLVKDPNFASASKGVSKAELKDVLTSENFK                          55
+ Majority          MAGDTLLSVLSDETHFENLTDGIFLSLVKDPNFASASKGVSKAELKDVLTSENFKGLFEDQAKAQNVVAVLKDSIAKTVL  80

                            10        20        30        40        50        60        70        80

  Majority          MAGDTLLSVLSDETHFENLTDGIFLSLVKDPNFASASKGVSKAELKDVLTSENFK                          55
  N risticii_ILLstrain-CP001431  MAGDTLLSVLSDETHFENLTDGIFLSLVKDPNFASASKGVSKAELKDVLTSENFKGLFEDQAKAQNVVAVLKDSIAKTVL  80
  N risticii_New York            MAGDTLLSVLSDETHFENLTDGIFLSLVKDPNFASASKGVSKAELKDVLTSENFKGLFEDQAKAQNVVAVLKDSIAKTVL  80
  N risticii_90-12               MAGDTLLSVLSDETHFENLTDGIFLSLVKDPNFASASKGVSKAELKDVLTSENFK                          55
  N risticii_25D                 MAGDTLLSVLSDETHFENLTDGIFLSLVKDPNFASASKGVSKAELKDVLTSENFK                          55
  N risticii_Michigan            MAGDTLLSVLSDETHFENLTDGIFLSLVKDPNFASASKGVSKMELKDVLTSENFK                          55
  N risticii_Oregon              MVGDTLLSVLSDETHFENLIDGIFLSLVKDPNFASASKGVSKAELKDVLTSENFK                          55
```

+ Majority

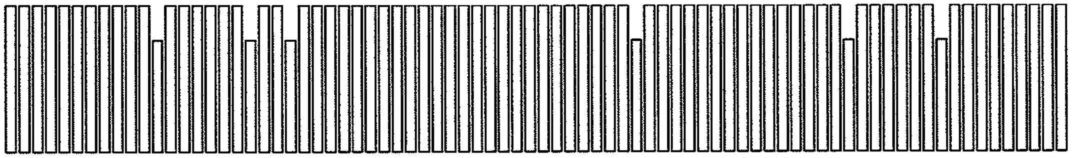

```
Majority                              LFEDQAKAQNVVAVLKDSIAKAVLESDKFKALLQTQGKAELQDLLTNDNFKGLFEDQAKAQNVVAVLKDSIAKAVLESDK
                                                170       180       190       200       210       220       230       240

N risticii_ILLstrain-CP001431         LFEDQAKAQNVVAVLKDSIAKAVLESDKFKALLQTQGKAELQDLLTNDNFKGLFEDQAKAQNVVAVLKDSIAKAVLESDK 136
N risticii_New York                   LFEDQAKAQNVVAVLKDSIAKAVLESDKFKALLQTQGKAELQDLLTNDNFKGLFEDQAKAQNVVAVLKDSIAKAVLESDK 240
N risticii_90-12                      LFEDQAKAQNVVAVLKDSIAKAVLESDKFKALLQTQGKAELQDLLTNDNFKGLFEDQAKAQNVVAVLKDSIAKAVLESDK 240
N risticii_25D                        LFEDQAKAQNVVAVLKDSIAKTVLESDKFKALLQTQGKAELQDLLTNDNFKGLFEDQAKAQNVVAVLKDSIAKAVLESDK 138
N risticii_Michigan                   LFEDQAKAQNVVAVLKDSIAKAVLESDKFKALLQTQGKAELQDLLTNDNFKGLFEDQAKAQNVVAVLKDSIAKAVLESDK 188
N risticii_Oregon                     LFEDQAKAQNVAAVLKDSAAKAVLESDKFKALLQTQGKAELQDLLTNENFKGLFEDQAKAQNVAAVLKDSAAKAVLESDK 136
```

FIG.6A-3

+ Majority

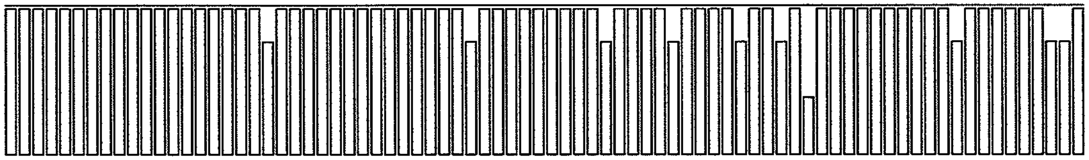

```
Majority                        FKALLQTQGKAELQDLLTNDNFKGLFEDQAKASSIKTILTNQNATGVLTDQTASNVITNXTAKEVLKNANAAELLKDNNA
                                         250       260       270       280       290       300       310       320
N risticii_ILLstrain-CP001431   FKALLQTQGKAELQDLLTNDNFKGLFEDQAKASSIKTILTNQNATGVLTDGTASNVITNDTAKEVLKNANAAELLKDNNA 216
N risticii_New York             FKALLQTQGKAELQDLLTNDNFKGLFEDQAKASSIKTILTNQNATGVLTDGTASNVITNNTAKEVLKNANAAELLKDNNA 320
N risticii_90-12                FKALLQTQGKAELQDLLTNDNFKGLFEDQAKASSIKTILTNQNATGVLTDGTASNVITNNTAKEVLKNANAAELLKDNNA 320
N risticii_25D                  FKALLQTQGKAELQDLLTNDNFKGLFEDQAKASSIKTILTNQNATGVLTDGTASNVITNDTAKEVLKNANAAELLKDNNA 216
N risticii_Michigan             FKALLQTQGKAELQDLLTNDNFKGLFEDQAKASSIKTILTNQNATGVLTDGTASNVITNNTAKEVLKNANAAELLKDNNA 288
N risticii_Oregon               FKALLQTQGKAELQDLLTNENEKGLFEDQAKASSAKTILTNQNAIGVLTNGTASAVINNDTAKEVLKNANSAELLKDSTA 216
```

FIG.6B-1

+ Majority

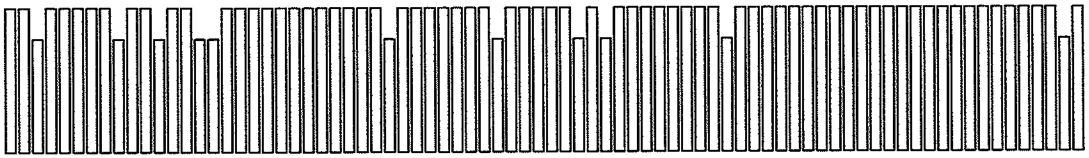

```
Majority                        AEVLKDETAKEILKNIKFKEILKGAGKDIIKNILTDGTGTFKGLLECAGKDKVGNVLTNQTFKKLFESPGNEEIKDILIN
                                          330       340       350       360       370       380       390       400

N ristici_ILLstrain-CP001431    AEVLKDETAKEILKNIKFKEILKGAGKDIIKNILTDGTGTFKGLLECAGKDKVGNVLTNQTFKKLFESPGNEEIKDILIN 296
N risticii_New York             AEVLKDETAKEILKNIKFKEILKGAGKDIIKNILTDGTGTFKGLLECAGKDKVGNVLTNQTFKKLFESPGNEEIKDILIN 400
N risticii_90-12                AEVLKDETAKEILKNIKFKEILKGAGKDIIKNILTDGTGTFKGLLECAGKDKVGNVLTNQTFKKLFESPGNEEIKDILIN 400
N risticii_25D                  AEVLKDETAKEILKNIKFKEILKGAGKDIIKNILTDGTGTFKGLLECAGKDKVGNVLTNQTFKKLFESPGNEEIKDILIN 296
N risticii_Michigan             AEVLKDETAKEILKNIKFKEILKGAGKDIIKNILTDGTGTFKGLLECAGKDKVGNVLTNQTFKKLFESPGNEEIKDILIN 348
N risticii_Oregon               AEILKDETIKEMLKSSKFKEILKGAGKDTIKNILTDSTGTFKELMECAGKDKVENVLTNQTFKKLFESPGNEEIKDILTN 296
```

FIG.6B-2

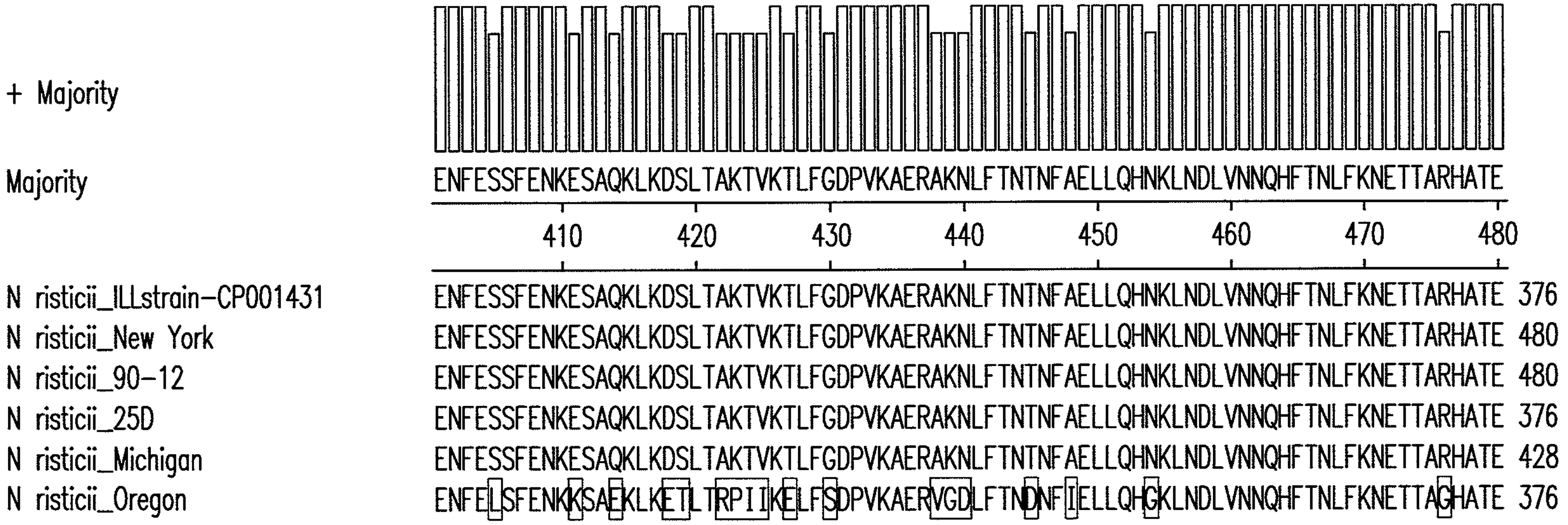

FIG.6B-3

| | 410 | 420 | 430 | 440 | 450 | 460 | 470 | 480 | |
|---|---|---|---|---|---|---|---|---|---|
| N risticii_ILLstrain-CP001431 | ENFESSFENKESAQKLKDSLTAKTVKTLFGDPVKAERAKNLFTNTNFAELLQHNKLNDLVNNQHFTNLFKNETTARHATE | | | | | | | | 376 |
| N risticii_New York | ENFESSFENKESAQKLKDSLTAKTVKTLFGDPVKAERAKNLFTNTNFAELLQHNKLNDLVNNQHFTNLFKNETTARHATE | | | | | | | | 480 |
| N risticii_90-12 | ENFESSFENKESAQKLKDSLTAKTVKTLFGDPVKAERAKNLFTNTNFAELLQHNKLNDLVNNQHFTNLFKNETTARHATE | | | | | | | | 480 |
| N risticii_25D | ENFESSFENKESAQKLKDSLTAKTVKTLFGDPVKAERAKNLFTNTNFAELLQHNKLNDLVNNQHFTNLFKNETTARHATE | | | | | | | | 376 |
| N risticii_Michigan | ENFESSFENKESAQKLKDSLTAKTVKTLFGDPVKAERAKNLFTNTNFAELLQHNKLNDLVNNQHFTNLFKNETTARHATE | | | | | | | | 428 |
| N risticii_Oregon | ENFELSFENKKSAEKLKETLTRPTIKELFSDPVKAERVGDLFTNDNFIELLQHGKLNDLVNNQHFTNLFKNETTAGHATE | | | | | | | | 376 |

+ Majority

Majority  ENFESSFENKESAQKLKDSLTAKTVKTLFGDPVKAERAKNLFTNTNFAELLQHNKLNDLVNNQHFTNLFKNETTARHATE + Majority Majority
ILTSPHFKASLENNEAVTNLKKLLTHSALRELFSNDNLENATSFAKKLRELGIVRTR—
          490           500           510           520           530

N risticii_ILLstrain-CP001431    ILTSPHFKASLENNEAVTNLKKLLTHSALRELFSNDNLENATSFAKKLRELGIVRTR.
N risticii_New York              ILTSPHFKASLENNEAVTNLKKLLTHSALRELFSNDNLENATSFAKKLRELGIVRTR.
N risticii_90-12                 ILTSPHFKASLENNEAVTNLKKLLTHSALRELFSNDNLENATSFAKKLRELGIVRTR.
N risticii_25D                   ILTSPHFKASLENNEAVTNLKKLLTHSALRELFSNDNLENATSFAKKLRELGIVRTR.
N risticii_Michigan              ILTSPHFKASLENNEAV[A]NLKKLLT[N]SALRELFSNDNLENATSFAKKLRELGIVRTR.
N risticii_Oregon                ILTSPHFKASLENNEAVTNLKKLLTHSALRELFSNDNLE[D]ATSFAKKL[VE]LGI[T]ARIK.

Decoration 'Decoration #1': Box residues that differ from the Consensus.

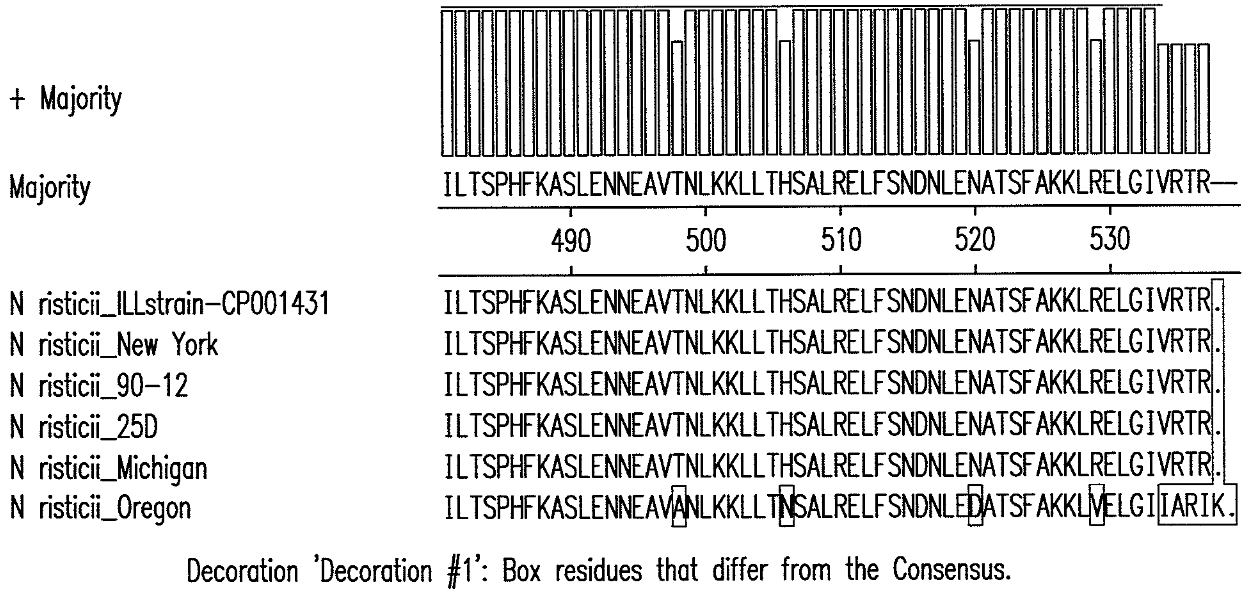

FIG.6C

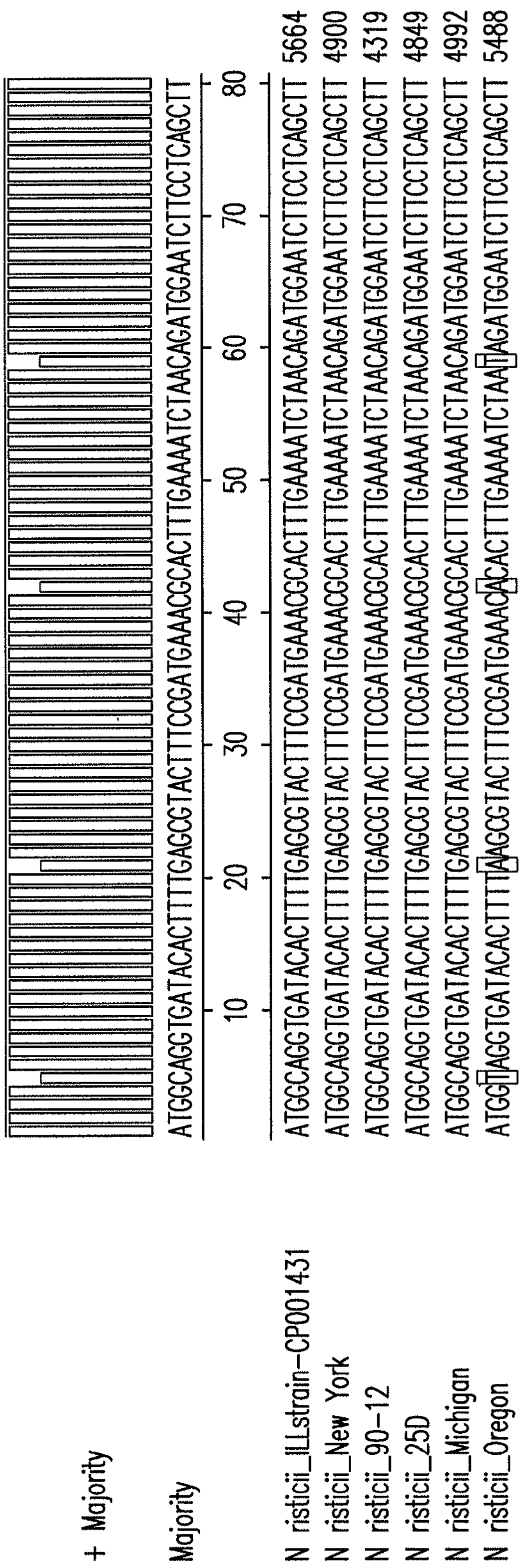

FIG.7A-1

| | | |
|---|---|---|
| Majority | ATGGCAGGTGATACACTTTTGAGCGTACTTTCCGATGAAACGCACTTTGAAAATCTAACAGATGGAATCTTCCTCAGCTT | 80 |
| N risticii_ILLstrain-CP001431 | ATGGCAGGTGATACACTTTTGAGCGTACTTTCCGATGAAACGCACTTTGAAAATCTAACAGATGGAATCTTCCTCAGCTT | 5664 |
| N risticii_New York | ATGGCAGGTGATACACTTTTGAGCGTACTTTCCGATGAAACGCACTTTGAAAATCTAACAGATGGAATCTTCCTCAGCTT | 4900 |
| N risticii_90-12 | ATGGCAGGTGATACACTTTTGAGCGTACTTTCCGATGAAACGCACTTTGAAAATCTAACAGATGGAATCTTCCTCAGCTT | 4319 |
| N risticii_25D | ATGGCAGGTGATACACTTTTGAGCGTACTTTCCGATGAAACGCACTTTGAAAATCTAACAGATGGAATCTTCCTCAGCTT | 4849 |
| N risticii_Michigan | ATGGCAGGTGATACACTTTTGAGCGTACTTTCCGATGAAACGCACTTTGAAAATCTAACAGATGGAATCTTCCTCAGCTT | 4992 |
| N risticii_Oregon | ATGGCAGGTAGGTGATACACTTTAAGCGTACTTTCCGATGAAACACACTTTGAAAATCTAATAGATGGAATCTTCCTCAGCTT | 5488 |

\+ Majority

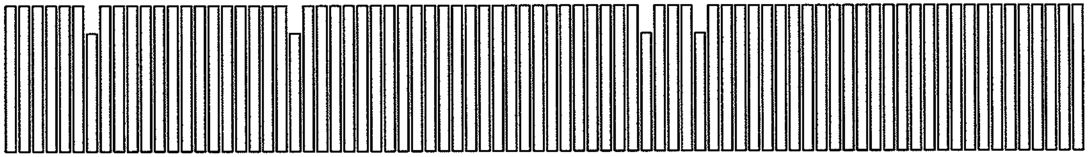

| | | |
|---|---|---|
| Majority | GGTTAAGGATCCGAATTTTGCTAGTGCATCAAAAGGCGTGAGTAAGGCAGAGTTGAAAGATGTACTCACTAGCGAAAACT | |
| | 90 100 110 120 130 140 150 160 | |
| N ristícii_ILLstrain-CP001431 | GGTTAAGGATCCGAATTTTGCTAGTGCATCAAAAGGCGTGAGTAAGGCAGAGTTGAAAGATGTACTCACTAGCGAAAACT | 5744 |
| N risticii_New York | GGTTAAGGATCCGAATTTTGCTAGTGCATCAAAAGGCGTGAGTAAGGCAGAGTTGAAAGATGTACTCACTAGCGAAAACT | 4980 |
| N risticii_90-12 | GGTTAAGGATCCGAATTTTGCTAGTGCATCAAAAGGCGTGAGTAAGGCAGAGTTGAAAGATGTACTCACTAGCGAAAACT | 4399 |
| N risticii_25D | GGTTAAGGATCCGAATTTTGCTAGTGCATCAAAAGGCGTGAGTAAGGCAGAGTTGAAAGATGTACTCACTAGCGAAAACT | 4929 |
| N risticii_Michigan | GGTTAAGGATCCGAATTTTGCTAGTGCATCAAAAGGCGTGAGTAAGGCAGAGTTGAAAGATGTACTCACTAGCGAAAACT | 5072 |
| N risticii_Oregon | GGTTAAAGATCCGAATTTTGCCAGTGCATCAAAAGGCGTGAGTAAGGTAGAATTGAAAGATGTACTCACTAGCGAAAACT | 5406 |

FIG.7A-2

+ Majority

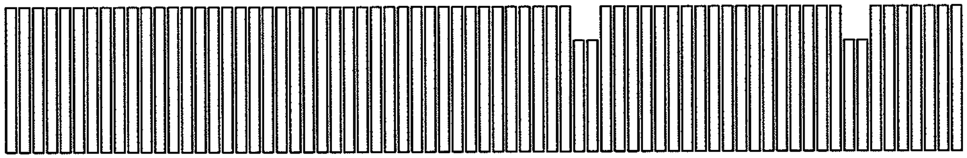

Majority TTAAGGGACTATTTGAAGATCAAGCTAAAGCACAAAATGTAGTCGCAGTACTGAAAGACTCAATAGCAAAG---------

170 180 190 200 210 220 230 240

N ristícii_ILLstrain-CP001431 TTAAGGGACTATTTGAAGATCAAGCTAAAGCACAAAATGTAGTCGCAGTACTGAAAGACTCAATAGCAAAG--------- 5815
N risticii_New York TTAAGGGACTATTTGAAGATCAAGCTAAAGCACAAAATGTAGTCGCAGTACTGAAAGACTCAATAGCAAAGACAGTACTG 5060
N risticii_90-12 TTAAGGGACTATTTGAAGATCAAGCTAAAGCACAAAATGTAGTCGCAGTACTGAAAGACTCAATAGCAAAGACAGTACTG 4479
N risticii_25D TTAAGGGACTATTTGAAGATCAAGCTAAAGCACAAAATGTAGTCGCAGTACTGAAAGACTCAATAGCAAAG--------- 5000
N risticii_Michigan TTAAGGGACTATTTGAAGATCAAGCTAAAGCACAAAATGTAGTCGCAGTACTGAAAGACTCAATAGCAAAG--------- 5143
N risticii_Oregon TTAAGGGACTATTTGAAGATCAAGCTAAAGCACAAAATGTAGCTGCAGTACTGAAAGACTCAGCAGCAAAG--------- 5335

FIG. 7A-3

+ Majority

| | | |
|---|---|---|
| Majority | ------------------------------------------------------------------------ | |
| | 250 260 270 280 290 300 310 320 | |
| N risticii_ILLstrain-CP001431 | ------------------------------------------------------------------------ | 5815 |
| N risticii_New York | GAAAGCGATAAATTCAAGGCGCTGCTTCAGACACAAGGTAAAGCTGAGTTGCAAGATTTACTAACCAATGACAATTTTAA | 5140 |
| N risticii_90-12 | GAAAGCGATAAATTCAAGGCGCTGCTTCAGACACAAGGTAAAGCTGAGTTGCAAGATTTACTAACCAATGACAATTTTAA | 4559 |
| N risticii_25D | ------------------------------------------------------------------------ | 5000 |
| N risticii_Michigan | ------------------------------------------------------------------------ | 5143 |
| N risticii_Oregon | ------------------------------------------------------------------------ | 5335 |

FIG. 7B-1

+ Majority

```
Majority                           XXXXXXXXXXXXXXXXXXXXXXXXXXXXXXXXXXXXXXXXXXXXXXXXXXXXXXXXXXXXXXXXXXXXXXXXXXXXXXXX
                                            410       420       430       440       450       460       470       480
N ristcii_ILLstrain-CP001431       -------------------------------------------------------------------------------- 5815
N risticii_New York                GCGATAAATTCAAGGCGCTGCTTCAGACACAAGGTAAAGCTGAGTTGCAAGATTTACTAACCAATGACAATTTTAAGGGA 5300
N risticii_90-12                   GCGATAAATTCAAGGCGCTGCTTCAGACACAAGGTAAAGCTGAGTTGCAAGATTTACTAACCAATGACAATTTTAAGGGA 4719
N risticii_25D                     -------------------------------------------------------------------------------- 5000
N risticii_Michigan                GCGATAAATTCAAGGCGCTGCTTCAGACACAAGGTAAAGCTGAGTTGCAAGATTTACTAACCAATGACAATTTTAAGGGA 5236
N risticii_Oregon                  -------------------------------------------------------------------------------- 5335
```

FIG. 7B-3

+ Majority

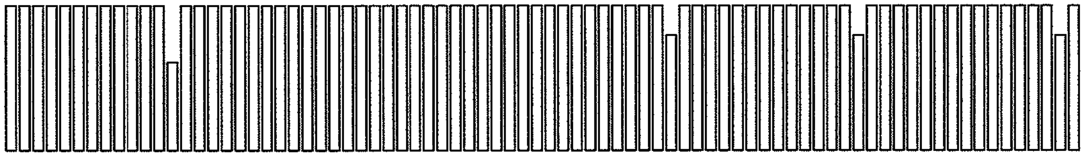

```
Majority                          TAAATTCAAGGCGTCTGCTTCAGACACAAGGTAAAGCTGAGTTGCAAGATTTACTAACCAATGACAATTTTAAGGGACTAT
                                          570       580       590       600       610       620       630       640

N ristieii_ILLstrain-CP001431     TAAATTCAAGGCGTCTGCTTCAGACACAAGGTAAAGCTGAGTTGCAAGATTTACTAACCAATGACAATTTTAAGGGACTAT 5912
N risticii_New York               TAAATTCAAGGCGTCTGCTTCAGACACAAGGTAAAGCTGAGTTGCAAGATTTACTAACCAATGACAATTTTAAGGGACTAT 5460
N risticii_90-12                  TAAATTCAAGGCGTCTGCTTCAGACACAAGGTAAAGCTGAGTTGCAAGATTTACTAACCAATGACAATTTTAAGGGACTAT 4879
N risticii_25D                    TAAATTCAAGGCGTCTGCTTCAGACACAAGGTAAAGCTGAGTTGCAAGATTTACTAACCAATGACAATTTTAAGGGACTAT 5097
N risticii_Michigan               TAAATTCAAGGCATCTGCTTCAGACACAAGGTAAAGCTGAGTTGCAAGATTTACTAACCAATGACAATTTTAAGGGACTAT 5396
N risticii_Oregon                 TAAATTCAAGGCATCTGCTTCAGACACAAGGTAAAGCTGAGTTGCAAGATCTACTAACCAATGAAAATTTTAAGGGACTGT 5238
```

FIG.7C-2

```
                      TTGAAGATCAAGCTAAAGCACAAAATGTAGTCGGCAGTACTGAAAGACTCAATAGCAAAGGCAGTACTGGAAAGCGATAAA
                      650       660       670       680       690       700       710       720
+ Majority

Majority              TTGAAGATCAAGCTAAAGCACAAAATGTAGTCGGCAGTACTGAAAGACTCAATAGCAAAGGCAGTACTGGAAAGCGATAAA

N risticii_ILLstrain-CP001431   TTGAAGATCAAGCTAAAGCACAAAATGTAGTCGGCAGTACTGAAAGACTCAATAGCAAAGGCAGTACTGGAAAGCGATAAA 5882
N risticii_New York             TTGAAGATCAAGCTAAAGCACAAAATGTAGTCGGCAGTACTGAAAGACTCAATAGCAAAGGCAGTACTGGAAAGCGATAAA 5540
N risticii_90-12                TTGAAGATCAAGCTAAAGCACAAAATGTAGTCGGCAGTACTGAAAGACTCAATAGCAAAGGCAGTACTGGAAAGCGATAAA 4959
N risticii_25D                  TTGAAGATCAAGCTAAAGCACAAAATGTAGTCGGCAGTACTGAAAGACTCAATAGCAAAGGCAGTACTGGAAAGCGATAAA 5177
N risticii_Michigan             TTGAAGATCAAGCTAAAGCACAAAATGTAGTCGGCAGTACTGAAAGACTCAATAGCAAAGGCAGTACTGGAAAGCGATAAA 5476
N risticii_Oregon               TTGAAGATCAAGCTAAAGCACAAAATGTACTGCAGTACTGAAAGACTCAGCACGAAAGGCAGTACTGGAAAGTGATAAA 5158
```

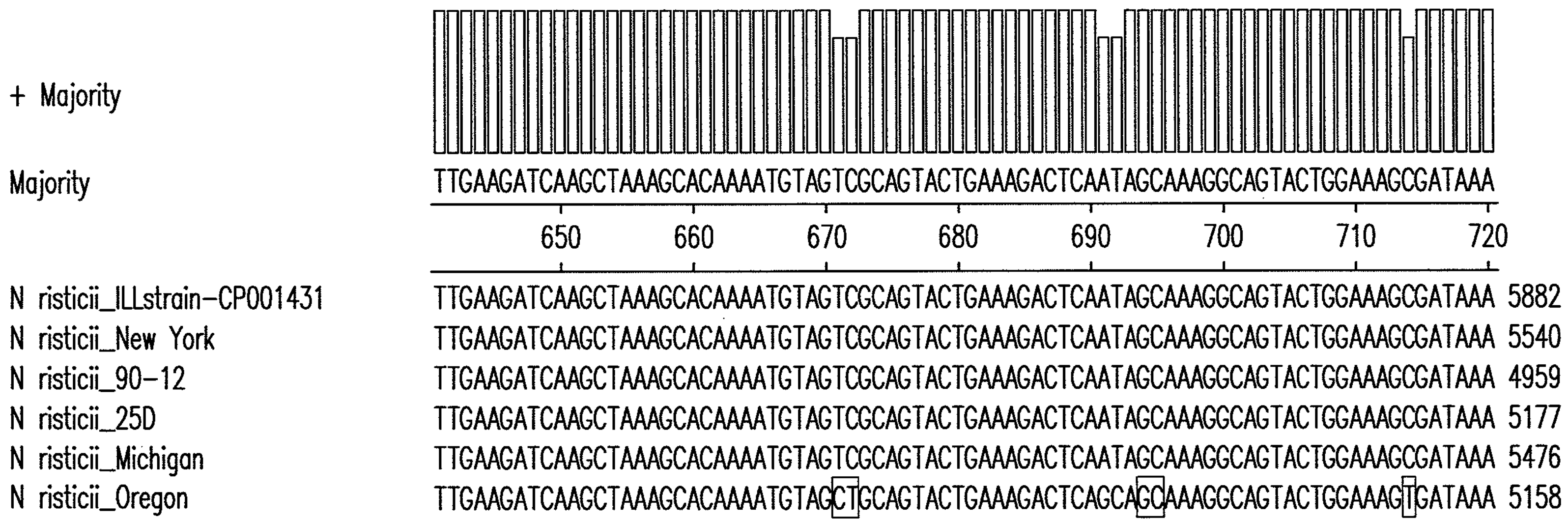

FIG.7C-3

+ Majority

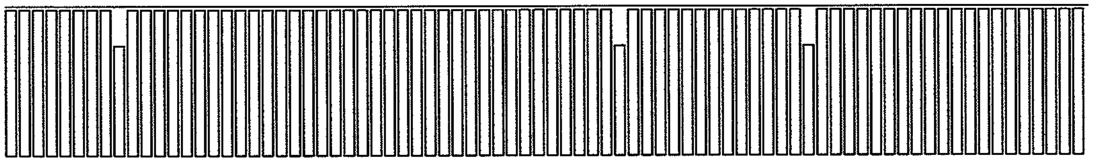

Majority TTCAAGGCGCTCGTTCAGACACAAGGTAAAGCTGAGTTGCAAGATTTACTAACCAATGACAATTTTAAGGGACTATTTGA 730 740 750 760 770 780 790 800

N ristícii_ILLstrain-CP001431 TTCAAGGCGCTCGTTCAGACACAAGGTAAAGCTGAGTTGCAAGATTTACTAACCAATGACAATTTTAAGGGACTATTTGA 6072
N risticii_New York TTCAAGGCGCTCGTTCAGACACAAGGTAAAGCTGAGTTGCAAGATTTACTAACCAATGACAATTTTAAGGGACTATTTGA 5820
N risticii_90-12 TTCAAGGCGCTCGTTCAGACACAAGGTAAAGCTGAGTTGCAAGATTTACTAACCAATGACAATTTTAAGGGACTATTTGA 5039
N risticii_25D TTCAAGGCGCTCGTTCAGACACAAGGTAAAGCTGAGTTGCAAGATTTACTAACCAATGACAATTTTAAGGGACTATTTGA 5257
N risticii_Michigan TTCAAGGCGCTCGTTCAGACACAAGGTAAAGCTGAGTTGCAAGATTTACTAACCAATGACAATTTTAAGGGACTATTTGA 5556
N risticii_Oregon TTCAAGGCACTCGTTCAGACACAAGGTAAAGCTGAGTTGCAAGATCTACTAACCAATGAAAATTTTAAGGGACTATTTGA 5078

FIG. 7D-1

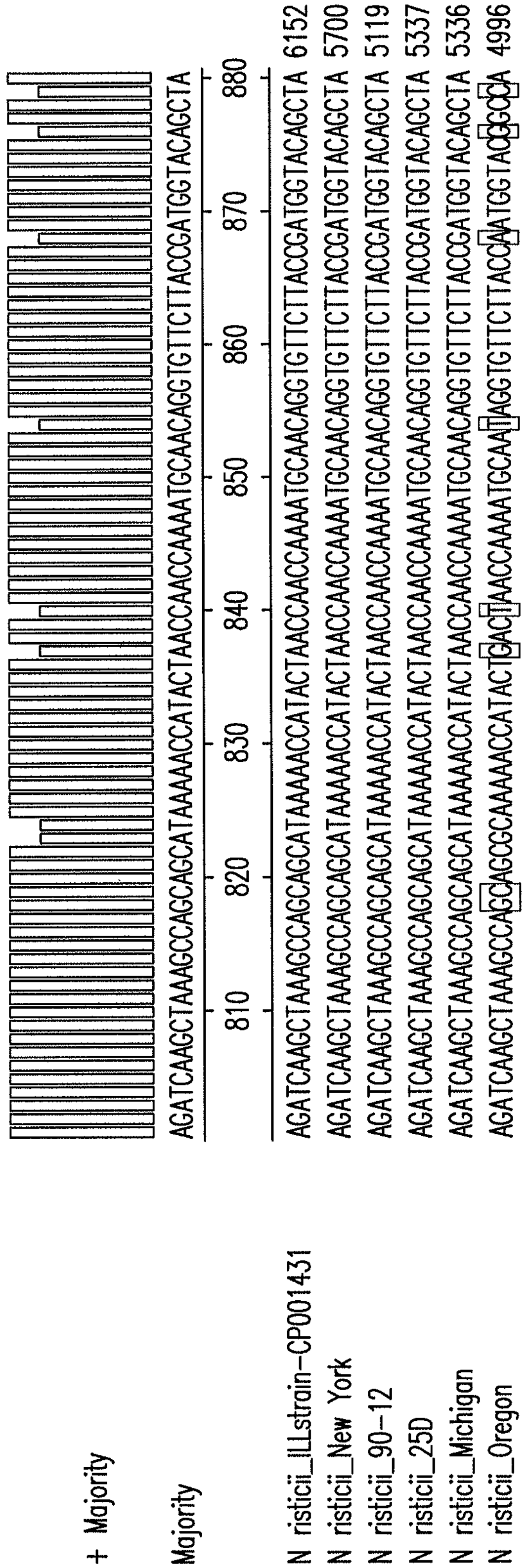

FIG.7D-2

```
                    AGATCAAGCTAAAGCCAGCAGCAGCATAAAAACCATACTAACCAACCAAAATGCAACAGGTGTTCTTACCGATGGTACAGCTA
                    810        820        830        840        850        860        870        880

N risticii_ILLstrain-CP001431   AGATCAAGCTAAAGCCAGCAGCAGCATAAAAACCATACTAACCAACCAAAATGCAACAGGTGTTCTTACCGATGGTACAGCTA 6152
N risticii_New York             AGATCAAGCTAAAGCCAGCAGCAGCATAAAAACCATACTAACCAACCAAAATGCAACAGGTGTTCTTACCGATGGTACAGCTA 5700
N risticii_90-12                AGATCAAGCTAAAGCCAGCAGCAGCATAAAAACCATACTAACCAACCAAAATGCAACAGGTGTTCTTACCGATGGTACAGCTA 5119
N risticii_25D                  AGATCAAGCTAAAGCCAGCAGCAGCATAAAAACCATACTAACCAACCAAAATGCAACAGGTGTTCTTACCGATGGTACAGCTA 5337
N risticii_Michigan             AGATCAAGCTAAAGCCAGCAGCAGCATAAAAACCATACTAACCAACCAAAATGCAACAGGTGTTCTTACCGATGGTACAGCTA 5336
N risticii_Oregon               AGATCAAGCTAAAGCCAGCGCAAAAACCATACTGACTAACCAAAATGCAAAGGTGTTCTTACCAATGGTACGGCCA        4996
```

+ Majority

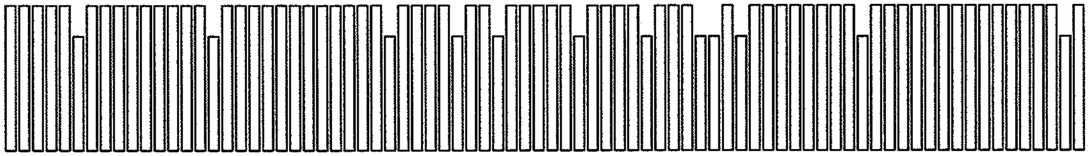

| | |
|---|---|
| Majority | AGACATAATAAAAAATATCCTCACAGATGGCACTGGTACTTTTAAAGGACTTCTCGAATGTGCAGGAAAAGATAAAGTAG |
| | 1050 1060 1070 1080 1090 1100 1110 1120 |
| N risticii_ILLstrain-CP001431 | AGACATAATAAAAAATATCCTCACAGATGGCACTGGTACTTTTAAAGGACTTCTCGAATGTGCAGGAAAAGATAAAGTAG 6392 |
| N risticii_New York | AGACATAATAAAAAATATCCTCACAGATGGCACTGGTACTTTTAAAGGACTTCTCGAATGTGCAGGAAAAGATAAAGTAG 5940 |
| N risticii_90-12 | AGACATAATAAAAAATATCCTCACAGATGGCACTGGTACTTTTAAAGGACTTCTCGAATGTGCAGGAAAAGATAAAGTAG 5359 |
| N risticii_25D | AGACATAATAAAAAATATCCTCACAGATGGCACTGGTACTTTTAAAGGACTTCTCGAATGTGCAGGAAAAGATAAAGTAG 5577 |
| N risticii_Michigan | AGACATAATAAAAAATATCCTCACAGATGGCACTGGTACTTTTAAAGGACTTCTCGAATGTGCAGGAAAAGATAAAGTAG 5876 |
| N risticii_Oregon | AGACACAATAAAAAACATCCTCACAGATAGCACCGGCACTTTCAAAGAACTCGTTGAATGTGCGGAAAAGATAAAGTGG 4758 |

FIG. 7E-2

+ Majority

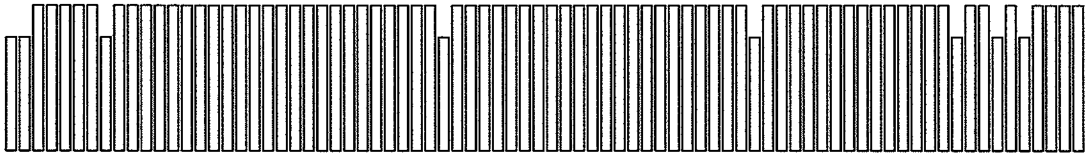

```
Majority                          GCAATGTTCTCACAAATCAGACTTTCAAAAAGCTGTTCGAAAGTCCAGGTAATGAGGAAATAAAAGATATCCTCATTAAC
                                          1130      1140      1150      1160      1170      1180      1190      1200
N ristícii_ILLstrain-CP001431     GCAATGTTCTCACAAATCAGACTTTCAAAAAGCTGTTCGAAAGTCCAGGTAATGAGGAAATAAAAGATATCCTCATTAAC 6472
N risticii_New York               GCAATGTTCTCACAAATCAGACTTTCAAAAAGCTGTTCGAAAGTCCAGGTAATGAGGAAATAAAAGATATCCTCATTAAC 6020
N risticii_90-12                  GCAATGTTCTCACAAATCAGACTTTCAAAAAGCTGTTCGAAAGTCCAGGTAATGAGGAAATAAAAGATATCCTCATTAAC 5439
N risticii_25D                    GCAATGTTCTCACAAATCAGACTTTCAAAAAGCTGTTCGAAAGTCCAGGTAATGAGGAAATAAAAGATATCCTCATTAAC 5657
N risticii_Michigan               GCAATGTTCTCACAAATCAGACTTTCAAAAAGCTGTTCGAAAGTCCAGGTAATGAGGAAATAAAAGATATCCTCATTAAC 5956
N risticii_Oregon                 AAAATGTGCTCACAAATCAGACTTTCAAAAAGTTGTTCGAAAGTCCAGGTAATGAAGAAATAAAAGATATACTTTACTAAC 4678
```

FIG. 7E-3

+ Majority

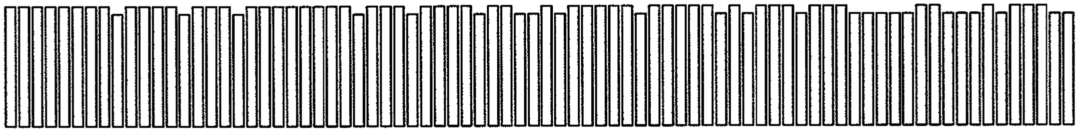

```
Majority                        GAAAATTTCGAGTCATCATTCGAGAACAAAGAAAGTGCTCAGAAATTAAAAGACAGTCTTACTGCCAAAACTGTCAAAAC
                                         1210      1220      1230      1240      1250      1260      1270      1280
N risticii_ILLstrain-CP001431   GAAAATTTCGAGTCATCATTCGAGAACAAAGAAAGTGCTCAGAAATTAAAAGACAGTCTTACTGCCAAAACTGTCAAAAC 6552
N risticii_New York             GAAAATTTCGAGTCATCATTCGAGAACAAAGAAAGTGCTCAGAAATTAAAAGACAGTCTTACTGCCAAAACTGTCAAAAC 6100
N risticii_90-12                GAAAATTTCGAGTCATCATTCGAGAACAAAGAAAGTGCTCAGAAATTAAAAGACAGTCTTACTGCCAAAACTGTCAAAAC 5519
N risticii_25D                  GAAAATTTCGAGTCATCATTCGAGAACAAAGAAAGTGCTCAGAAATTAAAAGACAGTCTTACTGCCAAAACTGTCAAAAC 5737
N risticii_Michigan             GAAAATTTCGAGTCATCATTCGAGAACAAAGAAAGTGCTCAGAAATTAAAAGACAGTCTTACTGCCAAAACTGTCAAAAC 6036
N risticii_Oregon               GAAAATTTTGAGTTATCGTTCGAGAATAAAAAAAGCGCCGAAAAATTGAAAGAGACTCTCACTAGGCGAATCATTAAAGA 4598
```

FIG. 7F-1

+ Majority

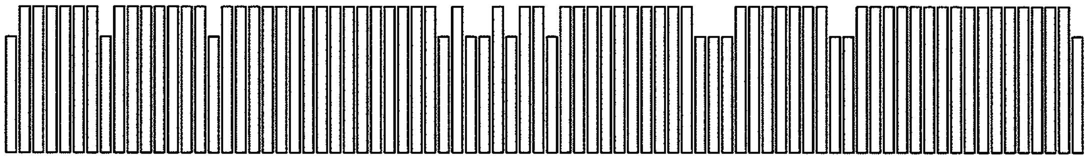

```
Majority                          CCTATTTGGCGATCCCGTAAAGGCTGAACGTGCGAAAAATTTGTTTACTAACACTAACTTTGCAGAACTTCTTCAACACA
                                          1290      1300      1310      1320      1330      1340      1350      1360

N risticii_ILLstrain-CP001431     CCTATTTGGCGATCCCGTAAAGGCTGAACGTGCGAAAAATTTGTTTACTAACACTAACTTTGCAGAACTTCTTCAACACA 6632
N risticii_New York               CCTATTTGGCGATCCCGTAAAGGCTGAACGTGCGAAAAATTTGTTTACTAACACTAACTTTGCAGAACTTCTTCAACACA 6180
N risticii_90-12                  CCTATTTGGCGATCCCGTAAAGGCTGAACGTGCGAAAAATTTGTTTACTAACACTAACTTTGCAGAACTTCTTCAACACA 5599
N risticii_25D                    CCTATTTGGCGATCCCGTAAAGGCTGAACGTGCGAAAAATTTGTTTACTAACACTAACTTTGCAGAACTTCTTCAACACA 5817
N risticii_Michigan               CCTATTTGGCGATCCCGTAAAGGCTGAACGTGCGAAAAATTTGTTTACTAACACTAACTTTGCAGAACTTCTTCAACACA 6116
N risticii_Oregon                 ACTATTTAGCGATCCAGTAAAGGCTGAACGTGTGGGAGATCTGTTTACTAATGATAACTTTATAGAACTTCTTCAACACG 4518
```

FIG. 7F-2

+ Majority

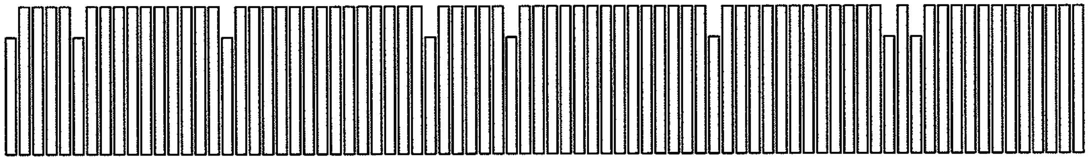

```
Majority                          ACAAACTAAATGACTTAGTAAACAATCAACACTTTACAAATCTGTTCAAAAATGAAACAACAGCCAGGCACGCAACCGAA
                                           1370      1380      1390      1400      1410      1420      1430      1440
N risticii_ILLstrain-CP001431     ACAAACTAAATGACTTAGTAAACAATCAACACTTTACAAATCTGTTCAAAAATGAAACAACAGCCAGGCACGCAACCGAA 6712
N risticii_New York               ACAAACTAAATGACTTAGTAAACAATCAACACTTTACAAATCTGTTCAAAAATGAAACAACAGCCAGGCACGCAACCGAA 6260
N risticii_90-12                  ACAAACTAAATGACTTAGTAAACAATCAACACTTTACAAATCTGTTCAAAAATGAAACAACAGCCAGGCACGCAACCGAA 5679
N risticii_25D                    ACAAACTAAATGACTTAGTAAACAATCAACACTTTACAAATCTGTTCAAAAATGAAACAACAGCCAGGCACGCAACCGAA 5897
N risticii_Michigan               ACAAACTAAATGACTTAGTAAACAATCAACACTTTACAAATCTGTTCAAAAATGAAACAACAGCCAGGCACGCAACCGAA 6196
N risticii_Oregon                 GCAAATTAAATGACTTGGTAAACAATCAACATTTTAGCAATCTGTTCAAAAACGAAACAACAGCCGGACACGCAACCGAA 4438
```

FIG. 7F-3

\+ Majority

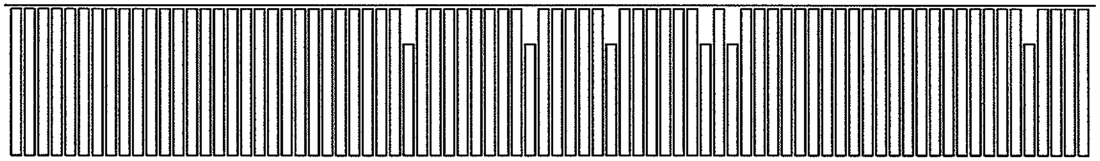

```
Majority                         ATCTTAACTTCTCCTCACTTCAAAGCATCGCTTGAAAACAATGAGGCAGTTACCAATTTGAAAAAATTACTCACTCATTC
                                       1450      1460      1470      1480      1490      1500      1510      1520

N risticii_ILLstrain-CP001431    ATCTTAACTTCTCCTCACTTCAAAGCATCGCTTGAAAACAATGAGGCAGTTACCAATTTGAAAAAATTACTCACTCATTC 6792
N risticii_New York              ATCTTAACTTCTCCTCACTTCAAAGCATCGCTTGAAAACAATGAGGCAGTTACCAATTTGAAAAAATTACTCACTCATTC 6340
N risticii_90-12                 ATCTTAACTTCTCCTCACTTCAAAGCATCGCTTGAAAACAATGAGGCAGTTACCAATTTGAAAAAATTACTCACTCATTC 5759
N risticii_25D                   ATCTTAACTTCTCCTCACTTCAAAGCATCGCTTGAAAACAATGAGGCAGTTACCAATTTGAAAAAATTACTCACTCATTC 5977
N risticii_Michigan              ATCTTAACTTCTCCTCACTTCAAAGCATCGCTTGAAAACAATGAGGCAGTTACCAATTTGAAAAAATTACTCACTCATTC 6276
N risticii_Oregon                ATCTTAACTTCTCCTCACTTCAAAGCATCTCTTGAAAATAATGAAGCAGTTGCTAATTTGAAAAAATTACTCACTAATTC 4358
```

FIG. 7G-1

+ Majority

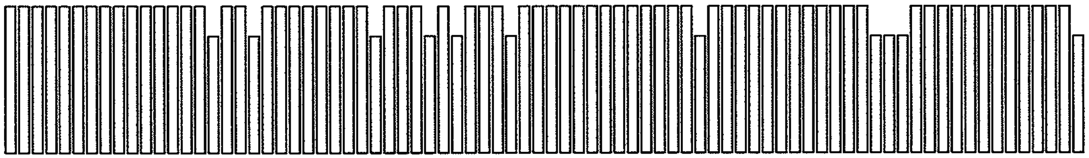

| | | |
|---|---|---|
| Majority | AGCACTAAGAGAGCTGTTCAGCAATGATAATTTAGAAAACGCAACTAGCTTTGCCAAGAAACTTAGAGAGCTAGGAATAG | |
| | 1610 1540 1550 1560 1570 1580 1590 1600 | |
| N risticii_ILLstrain-CP001431 | AGCACTAAGAGAGCTGTTCAGCAATGATAATTTAGAAAACGCAACTAGCTTTGCCAAGAAACTTAGAGAGCTAGGAATAG | 5872 |
| N risticii_New York | AGCACTAAGAGAGCTGTTCAGCAATGATAATTTAGAAAACGCAACTAGCTTTGCCAAGAAACTTAGAGAGCTAGGAATAG | 6420 |
| N risticii_90-12 | AGCACTAAGAGAGCTGTTCAGCAATGATAATTTAGAAAACGCAACTAGCTTTGCCAAGAAACTTAGAGAGCTAGGAATAG | 5839 |
| N risticii_25D | AGCACTAAGAGAGCTGTTCAGCAATGATAATTTAGAAAACGCAACTAGCTTTGCCAAGAAACTTAGAGAGCTAGGAATAG | 6057 |
| N risticii_Michigan | AGCACTAAGAGAGCTGTTCAGCAATGATAATTTAGAAAACGCAACTAGCTTTGCCAAGAAACTTAGAGAGCTAGGAATAG | 6356 |
| N risticii_Oregon | AGCACTAAGAGAGCTATTTAGCAATGACAATCTGGAAGACGCAACTAGCTTCGCCAAGAAACTTGTGGAGCTAGGAATAA | 4278 |

FIG. 7G-2

N. ristcii OR SSA#1 gene

ATGCCAGGCGATACACTTTTGAGCGTACTTTCCAATGACACATATTTTAGTAG
CTTAACTGATGAACTCCTCCTCAGCCTAATTAAGGACACAGTTTTCAATGGAA
TGATAAAAGGCGATGGAAAGATAGAATTAAAAGACATTCTTACAGATAACAC
CGGCAAATTTAGAGAGCTTGTAGAAAGTAGCAGTAAAGATATATTAAAAAGC
ATACTTACCGACAGCACAGGTAACTTTAAAGGGCTTATAGAAAGCGCAGGTA
AAGAGAAAGTAAAAGCACTTCTCACAGATGAGAACTTTAAAAAATTATTTGA
GGACGATACGAAAGCAAATCATGTAAAAGAGGTACTTACAGACACAAATGC
TAAGGAAATCCTTACGGATCAAACAGGCAAAGAAGTCCTAAAAAACAGCAC
AGCTAAAGATATATTAAAAAGCACAAATGCAGCCGAGGTACTAAAAGACGC
CAATGCTAAGGAAATCCTTACGGATCAAACGGGCAAAGAAGTCCTAAAAAA
CAGCACAGCTAAAGATATATTAAAAAGCACAAATGCAGCCGAGGTACTAAA
AGACGCCAATGCTAAGGAAATCCTTACGGATCAAACGGGCAAAGAAGTCCTA
AAAAACAGCACAGCTAAAGATATATTAAAAGACACAAATGCAGCCGAGGTA
CTAAAAGACGACACAGCTAAGGAAGTATTAAAAAACAGTAAATTTAAAGAA
GCAATAACAGGTGCAGGTAAAGACATACTAAAAGACATTCTTACAGACAGCA
CCGGTAAATTTAAAGAGCTTATAGAAAGCGCAGGTAAAGAGAAAGTAAAAG
CGCTTCTCACAGATGAGAACTTTAAAAAATTATTTGAGGACGATACGAAAGC
AAACCATGTAAAAGAGGTACTTACAGACATAAATGCTAAGGAAATCCTTACG
GATCAAACAGCTAAAGAAGTACTAAAAGACAGCACAGCCAAAGAAGTACTA
AAACACACTAAGTTTAAAGAAGCAATAACAGGTGCAGGTAAAGACATACTA
AAAGACATTCTTACAGACAGCACAGGTAAATTGAAAGGGCTTATAGAAAGTA
CAGGTAAAAACGAATTCAAAGATCTCCTTACTAATGACAGCTTTAAAAGCTT
ATTTGACAGCACAAATAGCGCCCAAGCTGTTAAAGCAATTTTTACCAAGAGT
GAGCTTAAACCCCTACTTGAAACATGTAAGCAAAACGCAAACAAAGTGCAAG
CACTCGAAGGAGCCTTGGAAAGCCTAAAAGATTTACTTACAGAGAGCGACAG
CAGCAAGTATGCTGAGAAATTACAAGCGTTTGGAAAGGAGCTTTGCACGAAA
AGAAAGGAGTGTGATGGTGCTAGCAATTTAAGCTGCAGTAACCTTACAGTAA
GTTGCTCTAGTACGTCTAGTAGTTGA [SEQ ID NO.: 25]

FIG.8

N. ristcii OR SSA#2 gene

ATGTTCAACCAAGTAATAAAAGGTGAGGGAAAAACAGAATTAAAAGACATA
CTTACGGATAGCACTGGTAAGTTTAAGGAGCTTATAGAAGGCACAGGTAAGG
ATATACTAAAAAGCATACTCACAGACGGCTCAGGCAACTTTAAAGGACTTGT
GGAAAGCAATGGTAGGACAGAGGCAAAAGAGGTACTCACCCATGGGAAATT
CAAGGAATTATTCAGTACTTCTGACAGAGCTGGTGTTACCAAAGAAGTCTTA
ACCGCAGAACAATTTGAAAAGCTACTTGAAGGCAGCGGTAAGACTCAAGCA
AAAGAGGTGCTCACAAACAAGAACTTTAAAAAATTATTTGATACTGCCGACA
GTGCTAAAATTGCTAAAGAAGTGCTTACGGCAGAACAATTTGAAAAGTTACT
TGAAGGTAGCGGTAAGACTCAAGCAAAAGAGGTACTCACAAACGAGAACTT
TAAAAAATTATTTGATACTGCCGACAGCGCTGGTATTGTTAAAGAAGTGCTTA
CCGCACAACAATTTAAACAATTGCTCAAAGGTAGCGGCAAGACTCAAGCAAA
AGAGGTGCTCATAAACGAGAACTTTAGTAAGTTATTTGATACTGCTGATAGA
GCTGGTATTGCTAAAGAAGTTCTCACTGCAGAACAATTTGAAAAGCTACTTG
AAGGCAGCGGTAAGACTCAAGTAAAAGAGGTTCTCATAAGCGAGAACTTTAA
AAATTTATTTGAAAACGGCGCTAAAGATAAGGTAAAAGACCTCCTTGTCGAC
AAGAAGTTTAAAGAGCTGTTTGCCGATGCAACAAAAGCTGACTATGTAAAAG
AAATACTCACAGACAGCACAGCTAAGGAGATACTTACAAACCAAACAGCAA
AAGAGGTACTGAAGAATGATACAGCTAAGGAAGTACTAAAATGCGATAAAT
TTAAAGAAGCAATAGCAGGTACAGGTAAAGACATACTAAAAGACATTCTTAC
AGACAGCACGGGTAACTTTAAAAGGCTTATAGAAGGCACTGGTAAGGAGAA
AGTAAAAGAACTTCTTACTGATGAGAAGTTTAAAAAACTTATGGAAAGTACA
GCCAAGGATGCGGTAAAAGAAGTTCTTACAAATGAGAATTTTCAAAAATTAT
TTAACCAAGTTATCAAAGCTGGACATGTTAAGAACGCACTAATAAACGAAAA
CTTCTGGAATTTATTTGTAAAGGGTGAAAAAGAATGGAGTAATGAATCATCA
TTTGTAAAAACCATAAGTGAACTGAAAGATCTAATCCACTGCGAAGATAGTC
AGCATGAAGAAAAACTAAAAGCCTTTGGAGATAAGCTGAAGAAGGCAAAAA
ATCCCAACCAAAAGAAAGAAAAGTAG [SEQ ID NO.: 26]

FIG.9

N. risticii NY SSA#1 gene

ATGTCAAATGAAACACTTCTGAGCGTACTTTCTGATGAAACGCACTTTGCTAA
TCTAGTTGATGAACTTCTTCTCAGCTTGGTTAAAGACAGTATTTTCACTCAAG
TAATAAAAGGCGAGGGAAAGACAGAATTAAAAGACATTCTTACAGATAGCA
CTGGCAAGTTTAAAGAGCTGATAGGAAGTAGCGGTAAGGATATACTAAAAA
GCATACTCACAGATGGCTCAGGCAACTTTAAAGGCCTTATAGAAAGCACAGG
TAAGGCAGAAGTAAAAGAGGTACTCACTAATGAAAAATTCAAAGAGCTTTTT
GGAAGCGATGGTAAGGATATATTAAAAGACATACTCACAGATAGCACTGGTA
AGTTTAAAGAGCTGATAGGAAGTAGCGGTAAGGACATACTAAAAAACATTCT
TACAGATAGCACCGGTAAGTTTAAAGAACTTATAGAAAGTGCAGGTAAGGGT
AAGCTGAAAGACCTTCTTATTGATGGAAACTTTAAAAAATTATTTGAGGATG
ACACGAAAGCTGCTCATGTAAAAGAAATACTTACAGACAGCAACGCTAAGG
AAATACTCACAAATGAAGTAGCAAAAGAGGTACTAAAATCCGATAAATTTAA
AGATGCAATAACTGGTGCTGGTAAGGACGCACTAAAAGAGATACTTACTTGC
GATAAATTTAAAGATGCAGTAACAGGCAATGGTAAGGACGCACTAAAAGAA
ATACTTACTTGCGATAAATTTAAAGAGGCAGTAACAGGCGATGGTAAAGACA
AGCTAAAAGAGATTCTTACTCACGAGAAGTTTAAAGCACTCATAGAGAGTGA
AGGCAAAGACATACTGAAAGAAATTCTTACAGATAGTACCGGTAAATTTAAA
GAGCTAATAGAAAGCACTGGTAAGGATAAGCTAAAAGAGATTCTTACAGATA
ACACCGGTAACTTTAAAGGGCTTGTAGAAGGCGCCGGTAAGGATGAAGCAA
AAGCAGTACTTACTGACGAGAAATTTAAAGGCTTGTTTGATGACAAAACAAT
AGCTGGCTATGTAAAAGAAATACTCACCAGCGAGAAGTTTAAAAAACTGTTT
GAAAGTGCAGGTAAGACTAAAGTAAAAGAACTCCTCATTGATGAGAAGTTTC
AAAAATTATTTGAGGATGACACGAAAGCCAGTCATGTAAAAGAAATACTCAC
GAACGATACAGCTAAGGAAATACTTACCAATGATAAATTTAAGGAAGCAATA
ACAGGCGATGGTAAAGACATACTAAAAGGTATACTTACAGATAGCACTGGTA
ACTTTAAAGGCGCAATAACAGGTGCCGGTAAAGATGAGCTAAAAGACATACT
CACTAATAGCGAGTTTAAAAGCTTATTTGATAGCAAAGATAGCGCTGAAGCT
GTTAAAGCAATTTTTACCGATACTAAATTTAAGACCTTACTTCAAACATGCAA
GAAGAACCCAAACAATACACAGGCACTTGCAGCTGCTTTAGATGAACTAAAA
GAGCTAATTACCTGTGGCAGCAATGATCATGCAACAAAACTACAAGCCTTTG
GAAATGCGCTATGCAACAGAAAGAAGGAAACGTGCAGTAATTTTAGCTCTGC
AAACTGCACTGGTACAGCAGCTACATAA [SEQ ID NO.: 27]

FIG.10

N. risticii NY SSA#2 gene

ATGACAGACGATACACTTTTGAGTGTGCTTTCCAATGAAACTCATTTTAATAA
CTTAATTGATGAATTTCTTCTCAGCTTGGTTAAGGACGCAATGTTCAATCAAG
TAATAAAAGGTGAGGGAAAAACAGAATTAAAAGACATACTTACGGACACTA
CGGGCAAATTCAAAGAGCTGATCGGAGGTAGTGGTAAAGCTATATTAAAAAG
CATACTCACAGACAACACCGGTAATTTTAAAGCACTTATCGAAGGCAATGGT
AAGACCCAAGCAAAAGAGGTCCTTACACATGAGAAATTTAAGGAATTATTCA
GTACTGCTGACAGAGCTGGTATTGCTAAAGAAGTGCTTACTGCTGAACAATTT
GAAAAATTACTCAAAGGTAGCGGTAAGACCCAAGCAAAAGAGGTGCTAACA
AACGAGAACTTTAATAAATTATTTGATACCACCAGTAGTGCAAAGATTGCTA
AAGAAGTGCTTACTGCAGAACAATTTGAAAAGTTACTTAAAGGCAGCGGTAA
AACCCAAGCAAAAGAGGTGCTAACAAACGAGAACTTTAATAAATTATTTGAT
ACCACCGGTAGTGCAGATATTGCTAAAGAAGTGCTCACTGCAGAACAATTTG
AAAAGTTACTTAAAGGCAGCGGTAAAACCCAAGCAAAAGAGGTGCTAACAA
ACGAGAACTTTAATAAATTATTTGATACTACCGGTAGTGCAGATATTGCTAAA
GAAGTGCTCACTGCAGAACAATTTGAAAAGTTACTTGAAGGCAGCGGTAAGA
ATGAAATAAAAGAGGTTCTTACGAACGAGAACTTTAAAAAGTTATTTGATAC
CGCTGACAGCGCTAGTATTGCTAAAGAAGTGCTCACTGCAGAACAATTTGAA
AAGTTACTTGAAGGCAGCGGTAAGACTCAAGCAAAAGAGGTGCTCACAAAC
GAGAACTTTAAAAAACTATTCGAAAACAGCGGCAGAGACATACTAAAAGAC
ATTCTTACAGATAGTACTGGTAAATTTAAAGAGCTCATAGAAAGTACTGGCA
AGGAGAAAGTAAAAGAACTTCTTATCGACGGGAAATTTAAGGACCTGTTCAC
CGATGCAACAAAAGCTGGCTATGTAAAAGAAATACTCACGAACGATACAGCT
AAAGACATACTCACTAATGATAAATTTAAAGATGCAGTAACAGGTAAAGGTA
AAGATGAGCTAAAAAGTATACTTACCAATGATAATTTTAAAAAACTTGTGGA
AAGTACAGCCAAAGACAAGGTAAAAGAAGTTCTTACAAATGAGAATTTTCAA
AAATTGTTTGACCAAACCACAAAAGCTGGGCATGTTAAGAGCGCACTAACGG
ATGAAAACTTCTGGAATITATTTGTAAAGAGCAAAACAGAATGGAGTAGTGA
CTCACCGTTTGTAAAAACCATAAGTGAATTGAAAGACCTAATCCACTGCGAA
GATGGTAAGCATGAAGAAAAACTAAAAGCCTTTGGAGATAAGCTTAAGGAG
GCAAAAACCCCAGATTCAAAGAAAAAGAATTAG [SEQ ID NO.: 28]

FIG.11

N. risticii MI SSA#1 gene

ATGTCAAATGAAACACTTTTGAGCGTACTTTCAGATGAGACGCATTTTAACAA
CTTAGTTGATGAACTCCTCCTCAGCTTGGTTAAAGACAGTATTTTCACTCAAG
TGATAAAAGGCGAGGGAAAGACAGAATTAAAAGACATACTTACAGACAACA
CTGGCAAGTTTAAAGAGCTGATAGGAAGTAGCGGTAAGGATATACTAAAAA
GCATACTCACAGATGGCTCAGGCAACTTTAAAGGACTCATAGAAAGCACAGG
TAAGACACAAGTAAAAGAGGTCCTCACTAATGAAAAATTCAAAGAGCTTTTT
GGAAGCGATGGTAAGGATATATTAAAAGACATACTCACAGATAACACCGGTA
ACTTTAAAGGCCTTATAGAAAGCACAGGTAAGGCGCAAGTAAAAGAGGTACT
CACTAATGAAAAATTCAAGGAGCTTTTTGGAAGCGAAGGTAAAGACATACTA
AAAGAGATACTTACAGACAATACCGGCAATTTTAAAGGGCTTATAGAAGGCA
AAGGTAAGGATGAAGCAAAGGGAGTACTTACTGACGAGAAATTTAAAGGCT
TGTTTGATGACAAAACAATAGCTGGCTATGTAAAAGAAATACTCACCAGCGA
GAAGTTTAAAAAACTGTTTGAAAATGGTGGAAAGGAAAAAGTAAAAGAACT
TCTTATTGATGAGAACTTTAAAAAATTATTTGAGGATGACACGAAAGCTGCTC
ATGTAAAAGAAATACTTACAGACAGCAACGCTAAGGAAATACTCACAAATG
AAGTAGCAAAAGAGGTACTAAAATCCGATAAATTTAAAGATGCAATAACTGG
TGCTGGTAAGGACGCACTAAAAGAGATACTTACTTGCGATAAATTTAAAGAT
GCAGTAACAGGCAATGGTAAGGACGCACTAAAAGAAATACTTACTTGCGATA
AATTTAAAGAGGCAGTAACAGGCGATGGTAAAGACAAGCTAAAAGAGATTC
TTACTCACGAGAAGTTTAAAGCACTCATAGAGAGTGAAGGCAAAGACATACT
GAAAGACATTCTTACAGATAGTACCGGTAAATTTAAAGAGCTAATAGAAAGC
ACGGGTAAGGATAAGCTGAAAGAAATACTTGTCGATGAGAAATTTAAGGCCC
TGTTTACTGATGCAACAAAAGCCGGTTATGTAAAAGAAATACTTACAGACAG
CAACGCTAAGGAAATACTCACAAATGAAGTAGCAAAAGAGGTACTAAAATC
CGATAAATTTAAAGATGCAATAACTGGTGCTGGTAAGGACGCACTAAAAGAG
ATACTTACCTGTGATAAATTTAAAGATGCAGTAACAGGCAATGGTAAGGACG
CACTAAAAGAAATACTTACTTGCGATAAATTTAAAGATGCAGTAACAGGCAA
TGGTAAAGACAAGCTAAAAGAGATTCTTACTCACGAGAAGTTTAAAGCACTC
ATAGAGAGTGAAGGCAAAGACATACTAAAAGGTATACTTACAGATAGCACT
GGTAACTTTAAAGGCGCAATAACAGGTGCCGGTAAAGATGAGCTAAAAGAC
ATACTCACTAATAGCGAGTTTAAAAGCTTATTTGAGAGCAAAGATAGCGCTG
AAGCTGTTAAAGCAATTTTTACCAATGCTAAGTTTAAAGGACTACTTGAAAC
ATGCAAGAACAACCCAAAAAATACACAGGCGCTCGAAGGAGCTTTAGACAG
CTTAAAGGAGCTACTTGAAGTTAACGACAACGTTAACTATGGTAGCAAACTA
AAAGACTTTGGACAGAGTCTTTGCACAAAAAGAAAGGAATTAGATGATGGTT
TTACCAACCCAAATTGCAATAGTATTGTAGTTACTGTTCCTAATTCGACTCAT
TAA [SEQ ID NO.: 29]

FIG.12

N. risticii MI SSA#2 gene

ATGACAGACGATACACTTTTGAGTGTGCTTTCCAATGAAACTCATTTTAATAA
CTTAATTGATGAATTTCTTCTCAGCTTGGTTAAGGACGCAATGTTCAATCAAG
TAATAAAAGGTGAGGGAAAAACAGAATTAAAAGACATACTTACGGACACTA
CGGGCAAATTCAAAGAGCTGATCGGAGGTAGTGGTAAAGCTATATTAAAAAG
CATACTCACAGACAACACCGGTAATTTTAAAGCACTTATCGAAGGCAATGGT
AAGACCCAAGCAAAAGAGGTCCTTACACATGAGAAATTtAAGGAATTATTCA
GTACTGCTGACAGAGCTGGTATTGCTAAAGAAGTGCTTACTGCTGAACAATTT
GAAAAATTACTCAAAGGTAGCGGTAAGACCCAAGCAAAAGAGGTGCTAACA
AACGAGAACTTTAATAAATTATTTGATACCACCAGTAGTGCAAAGATTGCTA
AAGAAGTGCTTACTGCCGAACAATTTGAAAAGTTACTTAAAGGTAGCGGTAA
GACCCAAGCAAAAGAGGTGCTAACAAACGAGAACTTTAATAAATTATTTGAT
ACTACCGGTAGTGCAGATATTGCTAAAGAAGTGCTCACTGCAGAACAATTTG
AAAAGTTACTTAAAGGCAGCGGTAAAACCCAAGCAAAAGAGGTGCTAACAA
ACGAGAACTTTAATAAATTATTTGATACTACCGGTAGTGCAGATATTGCTAAA
GAAGTGCTCACTGCAGAACAATTTGAAAAGTTACTTGAAGGCAGCGGTAAGA
CTCAAGCAAAAGAGGTGCTCACAAACGAGAACTTTAAAAAACTATTCGAAAA
CAGCGGCAGAGACATACTAAAAGACATTCTTACAGATAGTACTGGTAAATTT
AAAGAGCTCATAGAAAGTACTGGCAAGGAGAAAGTAAAAGAACTTCTTATC
GACGGGAAATTTAAGGACCTGTTCACCGATGCAACAAAAGCTGGCTATGTAA
AAGAAATACTCACGAACGATACAGCTAAAGACATACTCACTAATGATAAATT
TAAAGATGCAGTAACAGGTAAAGGTAAAGATGAGCTAAAAAGTATACTTACC
AATGATAATTTTAAAAAACTTGTGGAAAGTACAGCCAAAGACAAGGTGAAA
GAAGTTCTTACAAATGAGAATTTTCAAAAATTGTTTGACCAAACCACAAAAG
CTGGGCATGTTAAGAGCGCACTAACGGATGAAAACTTCTGGAATTTATTTAC
AAAGAGTGACACAGAATTCAGTAATTACTCACCATTTGTAAAAACCATAAGT
GAATTGAAAGACCTAATTCACTGCGAAGATGGTAAGCATGAAGAAAAACTA
AAAGCCTTTGGAGATAAGCTTAAGGAGGCAAAAACCCCAGATTCAAAGAAA
AAGAATTAG [SEQ ID NO.: 30]

FIG.13

N. ristcii 111 (CP001431) SSA#1 gene

ATGTCAAATGAAACACTTCTGAGCGTACTTTCTGATGAAACGCACTTTGCTAA
TCTAGTTGATGAACTTCTTCTCAGCTTGGTTAAAGACAGTATTTTCACTCAAG
TAATAAAAGGCGAGGGAAAGACAGAATTAAAAGACATTCTTACAGATAGCA
CTGGCAAGTTTAAAGAGCTGATAGGAAGTAGCGGTAAGGATATACTAAAAA
GCATACTCACAGATGGCTCAGGCAACTTTAAAGGCCTTATAGAAAGCACAGG
TAAGGCAGAAGTAAAAGAGGTACTCACTAATGAAAAATTCAAAGAGGTTTTT
GGAAGCGATGGTAAGGATATATTAAAAGACATACTCACAGATAGCACTGGTA
AGTTTAAAGAGCTGATAGGAAGTAGCGGTAAGGACATACTAAAAAACATTCT
TACAGATAGCACCGGTAAGTTTAAAGAACTTATAGAAAGTGCAGGTAAGGGT
AAGCTGAAAGACCTTCTTATTGATGGAAACTTTAAAAAATTATTTGAGGATG
ACACGAAAGCTGCTCATGTAAAAGAAATACTTACAGACAGCAACGCTAAGG
AAATACTCACAAATGAAGTAGCAAAAGAGGTACTAAAATCCGATAAATTTAA
AGATGCAATAACTGGTGCTGGTAAGGACGCACTAAAAGAAATACTTACTTGC
GATAAATTTAAAGAGGCAGTAACAGGCGATGGTAAGGACGCACTAAAAGAA
ATACTTACTTGCGATAAATTTAAAGATGCAGTAACAGGCAATGGTAAAGACA
AGCTAAAAGAGATTCTTACTCACGAGAAGTTTAAAGCACTCATAGAGAGTGA
AGGCAAAGACATACTGAAAGACATTCTTACAGATAGTACCGGTAAATTTAAA
GAGCTAATAGAAAGCACGGGTAAGGATGAAGCAAAAGCAGTACTTACTGAC
GAGAAATTTAAAGACTTGTTTAATGACAAAACAACAGCTGGCTACGTGAAAG
AAATACTCACCAGTGATAAGTTTAAAAAATTATTTGAGGACAATACCAAAGC
TGGCTACGTGAAAGAAATACTCACGAACGATACAGCTAAGGAAATACTTACC
AATGATAAATTTAAGGAAGCAATAACAGGCGATGGTAAAGACATACTGAAA
GAAATTCTTACAGATAGCACTGGTAACTTTAAAGGCGCAATAACAGGTGCCG
GTAAAGATGAGCTAAAATACATACTCACTAATAGCGAGTTTAAAAGCTTATT
TGATAGCAAAGATAGCGCTGAAGCTGTTAAAGAAATATTTACCCACAGTAAG
TITAAAGAACTACTTAAAACGTGCAAGGACAACCCAAAAAATACGGCGGCGC
TTGCAGCTGCTTTAGATGAACTAAAAGATCTAATTACCTGTGGCAGCGGTGAT
CATGCAACAAAACTACAAGCCTTTGGAAGTGCACTATGCACCAGAAAAAAAG
AGTCGTGCGATAATTTTAGCTCTGCAAACTGCAGTAGTACAACAACTGCATA
A [SEQIDNO.: 31]

FIG.14

N. risticii 111 (CP001431) SSA#2 gene

ATGACAGACGATACACTTTTGAGTGTGCTTTCCAATGAAACTCATTTTAATAA
CTTAATTGATGAATTTCTTCTCAGCTTGGTTAAGGACGCAATGTTCAATCAAG
TAATAAAAGGTGAGGGAAAAACAGAATTAAAAGACATACTTACGGACACTA
CGGGCAAATTCAAAGAGCTGATCGGAGGTAGTGGTAAAGCTATATTAAAAAG
CATACTCACAGACAACACCGGTAATTTTAAAGCACTTATCGAAGGCAATGGT
AAGACCCAAGCAAAAGAGGTCCTTACACATGAGAAATTTAAGGAATTATTCA
GTACTGCTGACAGAGCTGGTATTGCTAAAGAAGTGCTTACTGCTGAACAATTT
GAAAAATTACTCAAAGGTAGCGGTAAGACCCAAGCAAAAGAGGTGCTAACA
AACGAGAACTTTAATAAATTATTTGATACCACCAGTAGTGCAAAGATTGCTA
AAGAAGTGCTTACTGCCGAACAATTTGAAAAGTTACTTAAAGGCAGCGGTAA
AACCCAAGCAAAAGAGGTGCTAACAAACAAGAACTTTAATAAATTATTTGAT
ACCACCGGTAGTGCAGATATTGCTAAAGAAGTGCTCACTGCAGAACAATTTG
AAAAGTTACTTAAAGGCAGCGGTAAAACCCAAGCAAAAGAGGTGCTAACAA
ACGAGAACTTTAATAAATTATTTGATACTACCGGTAGTGCAGATATTGCTAAA
GAAGTGCTCACTGCAGAACAATTTGAAAAGTTACTTGAAGGCAGCGGTAAGA
ATGAAATAAAAGAGGTTCTTACGAACGAGAACTTTAAAAAGTTATTTGATAC
CGCTGACAGCGCTAGTATTGCTAAAGAAGTGCTCACTGCAGAACAATTTGAA
AAGTTACTTGAAGGCAGCGGTAAGACTCAAGCAAAAGAGGTGCTCACAAAC
GAGAACTTTAAAAAACTATTCGAAAACAGCGGCAGAGACATACTAAAAGAC
ATTCTTACAGATAGTACTGGTAAATTTAAAGAGCTCATAGAAAGTACTGGCA
AGGAGAAAGTAAAAGAACTTCTTATCGACGGGAAATTTAAGGACCTGTTCAC
CGATGCAACAAAAGCTGGCTATGTAAAAGAAATACTCACGAACGATACAGCT
AAAGACATACTCACTAATGATAAATTTAAAGATGCAGTAACAGGTAAAGGTA
AAGATGAGCTAAAAAGTATACTTACCAATGATAATTTTAAAAAACTTGTGGA
AAGTACAGCCAAAGACAAGGTAAAAGAAGTTCTTACAAATGAGAATTTTCAA
AAATTGTTTGACCAAACCACAAAAGCTGGGCATGTTAAGAGCGCACTAACGG
ATGAAAACTTCTGGAATTTATTTACAAAGAGTGACACAGAATTCAGTAATTA
CTCACCATTTGTAAAAACCATAAGTGAATTGAAAGACCTAATTCACTGCGAA
GATGGTAAGCATGAAGAAAAACTAAAAGCCTTTGGAGATAAGCTTAAGGAG
GCAAAAACCCCAGATTCAAAGAAAAAGAATTAG [SEQIDNO.: 32]

FIG. 15

SEQUENCE LISTING

<160> NUMBER OF SEQ ID NOS: 36

<210> SEQ ID NO 1
<211> LENGTH: 501
<212> TYPE: PRT
<213> ORGANISM: Ehrlichia risticii

<400> SEQUENCE: 1

Met Ser Asn Glu Thr Leu Leu Ser Val Leu Ser Asp Glu Thr His Phe
1 5 10 15

Ala Asn Leu Val Asp Glu Leu Leu Leu Ser Leu Val Lys Asp Ser Ile
20 25 30

Phe Thr Gln Val Ile Lys Gly Glu Gly Lys Thr Glu Leu Lys Asp Ile
35 40 45

Leu Thr Asp Ser Thr Gly Lys Phe Lys Glu Leu Ile Gly Ser Ser Gly
50 55 60

Lys Asp Ile Leu Lys Ser Ile Leu Thr Asp Gly Ser Gly Asn Phe Lys
65 70 75 80

Gly Leu Ile Glu Ser Thr Gly Lys Ala Glu Val Lys Glu Val Leu Thr
85 90 95

Asn Glu Lys Phe Lys Glu Leu Phe Gly Ser Asp Gly Lys Asp Ile Leu
100 105 110

Lys Asp Ile Leu Thr Asp Ser Thr Gly Lys Phe Lys Glu Leu Ile Gly
115 120 125

Ser Ser Gly Lys Asp Ile Leu Lys Asn Ile Leu Thr Asp Ser Thr Gly
130 135 140

Lys Phe Lys Glu Leu Ile Glu Ser Ala Gly Lys Gly Lys Leu Lys Asp
145 150 155 160

Leu Leu Ile Asp Gly Asn Phe Lys Lys Leu Phe Glu Asp Asp Thr Lys
165 170 175

Ala Ala His Val Lys Glu Ile Leu Thr Asp Ser Asn Ala Lys Glu Ile
180 185 190

Leu Thr Asn Glu Val Ala Lys Glu Val Leu Lys Ser Asp Lys Phe Lys
195 200 205

Asp Ala Ile Thr Gly Ala Gly Lys Asp Ala Leu Lys Glu Ile Leu Thr
210 215 220

Cys Asp Lys Phe Lys Glu Ala Val Thr Gly Asp Gly Lys Asp Ala Leu
225 230 235 240

Lys Glu Ile Leu Thr Cys Asp Lys Phe Lys Asp Ala Val Thr Gly Asn
245 250 255

Gly Lys Asp Lys Leu Lys Glu Ile Leu Thr His Glu Lys Phe Lys Ala
260 265 270

Leu Ile Glu Ser Glu Gly Lys Asp Ile Leu Lys Asp Ile Leu Thr Asp
275 280 285

Ser Thr Gly Lys Phe Lys Glu Leu Ile Glu Ser Thr Gly Lys Asp Glu
290 295 300

Ala Lys Ala Val Leu Thr Asp Glu Lys Phe Lys Asp Leu Phe Asn Asp
305 310 315 320

Lys Thr Thr Ala Gly Tyr Val Lys Glu Ile Leu Thr Ser Asp Lys Phe
325 330 335

Lys Lys Leu Phe Glu Asp Asn Thr Lys Ala Gly Tyr Val Lys Glu Ile
340 345 350

Leu Thr Asn Asp Thr Ala Lys Glu Ile Leu Thr Asn Asp Lys Phe Lys
355 360 365

```
Glu Ala Ile Thr Gly Asp Gly Lys Asp Ile Leu Lys Glu Ile Leu Thr
    370                 375                 380

Asp Ser Thr Gly Asn Phe Lys Gly Ala Ile Thr Gly Ala Gly Lys Asp
385                 390                 395                 400

Glu Leu Lys Tyr Ile Leu Thr Asn Ser Glu Phe Lys Ser Leu Phe Asp
                405                 410                 415

Ser Lys Asp Ser Ala Glu Ala Val Lys Glu Ile Phe Thr His Ser Lys
            420                 425                 430

Phe Lys Glu Leu Leu Lys Thr Cys Lys Asp Asn Pro Lys Asn Thr Ala
        435                 440                 445

Ala Leu Ala Ala Ala Leu Asp Glu Leu Lys Asp Leu Ile Thr Cys Gly
    450                 455                 460

Ser Gly Asp His Ala Thr Lys Leu Gln Ala Phe Gly Ser Ala Leu Cys
465                 470                 475                 480

Thr Arg Lys Lys Glu Ser Cys Asp Asn Phe Ser Ser Ala Asn Cys Ser
                485                 490                 495

Ser Thr Thr Thr Ala
            500
```

<210> SEQ ID NO 2
<211> LENGTH: 473
<212> TYPE: PRT
<213> ORGANISM: Ehrlichia risticii

<400> SEQUENCE: 2

```
Met Pro Gly Asp Thr Leu Leu Ser Val Leu Ser Asn Asp Thr Tyr Phe
1               5                   10                  15

Ser Ser Leu Thr Asp Glu Leu Leu Leu Ser Leu Ile Lys Asp Thr Val
            20                  25                  30

Phe Asn Gly Met Ile Lys Gly Asp Gly Lys Ile Glu Leu Lys Asp Ile
        35                  40                  45

Leu Thr Asp Asn Thr Gly Lys Phe Arg Glu Leu Val Glu Ser Ser Ser
    50                  55                  60

Lys Asp Ile Leu Lys Ser Ile Leu Thr Asp Ser Thr Gly Asn Phe Lys
65                  70                  75                  80

Gly Leu Ile Glu Ser Ala Gly Lys Glu Lys Val Lys Ala Leu Leu Thr
                85                  90                  95

Asp Glu Asn Phe Lys Lys Leu Phe Glu Asp Asp Thr Lys Ala Asn His
            100                 105                 110

Val Lys Glu Val Leu Thr Asp Thr Asn Ala Lys Glu Ile Leu Thr Asp
        115                 120                 125

Gln Thr Gly Lys Glu Val Leu Lys Asn Ser Thr Ala Lys Asp Ile Leu
    130                 135                 140

Lys Ser Thr Asn Ala Ala Glu Val Leu Lys Asp Ala Asn Ala Lys Glu
145                 150                 155                 160

Ile Leu Thr Asp Gln Thr Gly Lys Glu Val Leu Lys Asn Ser Thr Ala
                165                 170                 175

Lys Asp Ile Leu Lys Ser Thr Asn Ala Ala Glu Val Leu Lys Asp Ala
            180                 185                 190

Asn Ala Lys Glu Ile Leu Thr Asp Gln Thr Gly Lys Glu Val Leu Lys
        195                 200                 205

Asn Ser Thr Ala Lys Asp Ile Leu Lys Asp Thr Asn Ala Ala Glu Val
    210                 215                 220

Leu Lys Asp Asp Thr Ala Lys Glu Val Leu Lys Asn Ser Lys Phe Lys
225                 230                 235                 240
```

Glu Ala Ile Thr Gly Ala Gly Lys Asp Ile Leu Lys Asp Ile Leu Thr
245 250 255

Asp Ser Thr Gly Lys Phe Lys Glu Leu Ile Glu Ser Ala Gly Lys Glu
260 265 270

Lys Val Lys Ala Leu Leu Thr Asp Glu Asn Phe Lys Lys Leu Phe Glu
275 280 285

Asp Asp Thr Lys Ala Asn His Val Lys Glu Val Leu Thr Asp Ile Asn
290 295 300

Ala Lys Glu Ile Leu Thr Asp Gln Thr Ala Lys Glu Val Leu Lys Asp
305 310 315 320

Ser Thr Ala Lys Glu Val Leu Lys His Thr Lys Phe Lys Glu Ala Ile
325 330 335

Thr Gly Ala Gly Lys Asp Ile Leu Lys Asp Ile Leu Thr Asp Ser Thr
340 345 350

Gly Lys Leu Lys Gly Leu Ile Glu Ser Thr Gly Lys Asn Glu Phe Lys
355 360 365

Asp Leu Leu Thr Asn Asp Ser Phe Lys Ser Leu Phe Asp Ser Thr Asn
370 375 380

Ser Ala Gln Ala Val Lys Ala Ile Phe Thr Lys Ser Glu Leu Lys Pro
385 390 395 400

Leu Leu Glu Thr Cys Lys Gln Asn Ala Asn Lys Val Gln Ala Leu Glu
405 410 415

Gly Ala Leu Glu Ser Leu Lys Asp Leu Leu Thr Glu Ser Asp Ser Ser
420 425 430

Lys Tyr Ala Glu Lys Leu Gln Ala Phe Gly Lys Glu Leu Cys Thr Lys
435 440 445

Arg Lys Glu Cys Asp Gly Ala Ser Asn Leu Ser Cys Ser Asn Leu Thr
450 455 460

Val Ser Cys Ser Ser Thr Ser Ser Ser
465 470

<210> SEQ ID NO 3
<211> LENGTH: 539
<212> TYPE: PRT
<213> ORGANISM: Ehrlichia risticii

<400> SEQUENCE: 3

Met Ser Asn Glu Thr Leu Leu Ser Val Leu Ser Asp Glu Thr His Phe
1 5 10 15

Ala Asn Leu Val Asp Glu Leu Leu Leu Ser Leu Val Lys Asp Ser Ile
20 25 30

Phe Thr Gln Val Ile Lys Gly Glu Gly Lys Thr Glu Leu Lys Asp Ile
35 40 45

Leu Thr Asp Ser Thr Gly Lys Phe Lys Glu Leu Ile Gly Ser Ser Gly
50 55 60

Lys Asp Ile Leu Lys Ser Ile Leu Thr Asp Gly Ser Gly Asn Phe Lys
65 70 75 80

Gly Leu Ile Glu Ser Thr Gly Lys Ala Glu Val Lys Glu Val Leu Thr
85 90 95

Asn Glu Lys Phe Lys Glu Leu Phe Gly Ser Glu Gly Lys Asp Ile Leu
100 105 110

Lys Glu Ile Leu Thr Asp Asn Thr Gly Asn Phe Lys Gly Leu Ile Glu
115 120 125

Gly Lys Gly Lys Asp Glu Ala Lys Gly Val Leu Thr Asp Glu Lys Phe

-continued

```
    130                 135                 140

Lys Gly Leu Phe Asp Asp Lys Thr Ile Ala Gly Tyr Val Lys Glu Ile
145                 150                 155                 160

Leu Thr Ser Glu Lys Phe Lys Lys Leu Phe Glu Ser Ala Gly Lys Thr
                165                 170                 175

Lys Val Lys Glu Leu Leu Ile Asp Glu Lys Phe Gln Lys Leu Phe Glu
            180                 185                 190

Asp Asp Thr Lys Ala Ser His Val Lys Glu Ile Leu Thr Asp Ser Asn
        195                 200                 205

Ala Lys Glu Ile Leu Thr Asn Glu Val Ala Lys Glu Val Leu Lys Ser
    210                 215                 220

Asp Lys Phe Lys Asp Ala Ile Thr Gly Ala Gly Lys Asp Ala Leu Lys
225                 230                 235                 240

Glu Ile Leu Thr Cys Asp Lys Phe Lys Asp Ala Val Thr Gly Asn Gly
                245                 250                 255

Lys Asp Ala Leu Lys Glu Ile Leu Thr Cys Asp Lys Phe Lys Asp Ala
            260                 265                 270

Val Thr Gly Asn Gly Lys Asp Lys Leu Lys Glu Ile Leu Thr His Glu
        275                 280                 285

Lys Phe Lys Ala Leu Ile Glu Ser Glu Gly Lys Asp Ile Leu Lys Glu
    290                 295                 300

Ile Leu Thr Asp Ser Thr Gly Lys Phe Lys Glu Leu Ile Glu Ser Thr
305                 310                 315                 320

Gly Lys Asp Lys Leu Lys Glu Ile Leu Thr Asp Asn Thr Gly Asn Phe
                325                 330                 335

Lys Gly Leu Val Glu Gly Ala Gly Lys Asp Glu Ala Lys Ala Val Leu
            340                 345                 350

Thr His Glu Lys Phe Lys Asp Leu Phe Asn Asp Lys Thr Thr Ala Gly
        355                 360                 365

Tyr Val Lys Glu Ile Leu Thr Ser Asp Lys Phe Lys Lys Leu Phe Glu
    370                 375                 380

Asp Asn Thr Lys Ala Gly Tyr Val Lys Glu Ile Leu Thr Asn Asp Thr
385                 390                 395                 400

Ala Lys Glu Ile Leu Thr Asn Gln Thr Ala Lys Glu Val Leu Lys Asp
                405                 410                 415

Ser Thr Ala Lys Glu Ile Leu Lys Cys Asp Lys Phe Lys Asp Ala Ile
            420                 425                 430

Thr Gly Ala Gly Lys Asp Glu Leu Lys Tyr Ile Leu Thr Asn Asn Glu
        435                 440                 445

Phe Lys Ser Leu Phe Asp Ser Lys Asp Ser Ala Glu Ala Val Lys Ala
    450                 455                 460

Ile Phe Thr His Asn Lys Phe Lys Glu Leu Leu Lys Thr Cys Lys Asp
465                 470                 475                 480

Asn Pro Lys Asn Thr Ala Ala Leu Ala Ala Ala Leu Asp Glu Leu Lys
                485                 490                 495

Asp Leu Ile Thr Cys Asp Gly Asn Asn His Ala Thr Lys Leu Gln Ala
            500                 505                 510

Phe Gly Ser Ala Leu Cys Thr Arg Lys Lys Glu Ser Cys Asp Asn Phe
        515                 520                 525

Ser Pro Ala Ser Cys Ser Ser Thr Ala Ala Thr
    530                 535
```

<210> SEQ ID NO 4

<211> LENGTH: 628
<212> TYPE: PRT
<213> ORGANISM: Ehrlichia risticii

<400> SEQUENCE: 4

```
Met Ser Asn Glu Thr Leu Leu Ser Val Leu Ser Asp Glu Thr His Phe
1               5                   10                  15

Ala Asn Leu Val Asp Glu Leu Leu Leu Ser Leu Val Lys Asp Ser Ile
            20                  25                  30

Phe Thr Gln Val Ile Lys Gly Glu Gly Lys Thr Glu Leu Lys Asp Ile
        35                  40                  45

Leu Thr Asp Asn Thr Gly Lys Phe Lys Glu Leu Ile Glu Ser Ala Gly
    50                  55                  60

Lys Asp Ile Leu Lys Glu Ile Leu Thr Asp Asn Thr Gly Asn Phe Lys
65                  70                  75                  80

Gly Leu Ile Glu Gly Asn Gly Lys Thr Glu Ala Lys Glu Val Leu Thr
                85                  90                  95

Asn Glu Lys Phe Lys Glu Leu Phe Gly Ser Asn Gly Lys Asp Ile Leu
            100                 105                 110

Lys Asp Ile Leu Thr Asp Asn Thr Gly Asn Phe Lys Gly Leu Ile Glu
        115                 120                 125

Ser Ala Ala Lys Gly Lys Leu Lys Asp Leu Leu Ile Asp Glu Lys Phe
    130                 135                 140

Gln Lys Leu Phe Glu Asp Glu Thr Lys Ala Gly Arg Val Lys Glu Ile
145                 150                 155                 160

Leu Thr Asp Ser Asn Ala Lys Glu Ile Leu Thr Asn Glu Val Ala Lys
                165                 170                 175

Glu Val Leu Lys Ser Asp Lys Phe Lys Glu Ala Ile Thr Gly Asp Gly
            180                 185                 190

Lys Asp Ala Leu Lys Glu Ile Leu Thr Cys Asp Lys Phe Lys Glu Ala
        195                 200                 205

Val Thr Gly Asn Gly Lys Asp Ile Leu Lys Gly Ile Leu Thr Asp Ser
    210                 215                 220

Thr Gly Lys Phe Lys Glu Leu Ile Glu Ser Thr Ser Lys Asp Ile Leu
225                 230                 235                 240

Lys Glu Ile Leu Thr Asp Asn Thr Gly Asn Phe Lys Gly Leu Ile Glu
                245                 250                 255

Ser Thr Gly Lys Glu Lys Val Lys Glu Leu Leu Ile Asp Gly Lys Phe
            260                 265                 270

Lys Asp Leu Phe Thr Asp Ala Thr Lys Ala Gly Tyr Val Lys Glu Ile
        275                 280                 285

Leu Thr Asn Asp Thr Ala Lys Glu Val Leu Thr Asp Gln Thr Ala Lys
    290                 295                 300

Glu Val Leu Lys Asp Ser Thr Ala Lys Asp Ile Leu Lys Asp Thr Asn
305                 310                 315                 320

Ala Ala Ala Val Leu Lys Asn Ser Thr Ala Lys Glu Ile Leu Thr Asn
                325                 330                 335

Gln Thr Ala Lys Glu Val Leu Thr Asp Gly Thr Ala Lys Glu Val Leu
            340                 345                 350

Lys Glu Ile Leu Thr Cys Asp Lys Phe Lys Glu Ala Val Thr Gly Asn
        355                 360                 365

Gly Lys Asp Ile Leu Lys Gly Ile Leu Thr Asp Ser Thr Gly Lys Phe
    370                 375                 380

Lys Glu Leu Ile Glu Ser Thr Gly Lys Asp Lys Leu Lys Glu Ile Leu
```

```
385                 390                 395                 400

Thr Asp Asn Thr Gly Asn Phe Lys Gly Leu Val Glu Gly Ala Gly Lys
                405                 410                 415

Asp Glu Ala Lys Ala Val Leu Thr His Glu Lys Phe Lys Asp Leu Phe
            420                 425                 430

Asn Asp Lys Thr Thr Ala Gly Tyr Val Lys Glu Ile Leu Thr Ser Asp
        435                 440                 445

Lys Phe Lys Glu Leu Phe Thr Asp Ala Thr Lys Ala Gly Tyr Val Lys
    450                 455                 460

Glu Ile Leu Thr Asn Asp Thr Ala Lys Glu Ile Leu Thr Asp Gln Thr
465                 470                 475                 480

Ala Lys Glu Val Leu Lys Asp Gly Thr Ala Lys Asp Ile Leu Lys Asp
                485                 490                 495

Thr Asn Ala Ala Ala Leu Leu Lys Asp Ser Thr Ala Lys Glu Val Leu
            500                 505                 510

Lys Cys Asp Lys Phe Lys Glu Ala Ile Thr Gly Ala Gly Lys Asp Glu
        515                 520                 525

Leu Lys Tyr Ile Leu Thr Asn Ser Glu Phe Lys Ser Leu Phe Asp Ser
    530                 535                 540

Lys Asp Ser Ala Glu Ala Val Lys Ala Ile Phe Thr His Asn Lys Phe
545                 550                 555                 560

Lys Glu Leu Leu Glu Thr Cys Lys Asn Asn Pro Asn Asn Thr Gln Ala
                565                 570                 575

Leu Ala Asn Ala Leu Asp Glu Leu Lys Ala Leu Ile Thr Cys Gly Ser
            580                 585                 590

Gly Asp His Ala Thr Lys Leu Gln Ala Phe Gly Ser Ala Leu Cys Thr
        595                 600                 605

Lys Lys Lys Glu Leu Cys Ser Asn Phe Ser Ser Ala Asn Cys Ser Ser
    610                 615                 620

Thr Thr Thr Ala
625


<210> SEQ ID NO 5
<211> LENGTH: 622
<212> TYPE: PRT
<213> ORGANISM: Ehrlichia risticii

<400> SEQUENCE: 5

Met Ser Asn Glu Thr Leu Leu Ser Val Leu Ser Asp Glu Thr His Phe
1               5                   10                  15

Asn Asn Leu Val Asp Glu Leu Leu Leu Ser Leu Val Lys Asp Ser Ile
            20                  25                  30

Phe Thr Gln Val Ile Lys Gly Glu Gly Lys Thr Glu Leu Lys Asp Ile
        35                  40                  45

Leu Thr Asp Asn Thr Gly Lys Phe Lys Glu Leu Ile Gly Ser Ser Gly
    50                  55                  60

Lys Asp Ile Leu Lys Ser Ile Leu Thr Asp Gly Ser Gly Asn Phe Lys
65                  70                  75                  80

Gly Leu Ile Glu Ser Thr Gly Lys Thr Gln Val Lys Glu Val Leu Thr
                85                  90                  95

Asn Glu Lys Phe Lys Glu Leu Phe Gly Ser Asp Gly Lys Asp Ile Leu
            100                 105                 110

Lys Asp Ile Leu Thr Asp Asn Thr Gly Asn Phe Lys Gly Leu Ile Glu
        115                 120                 125
```

```
Ser Thr Gly Lys Ala Gln Val Lys Glu Val Leu Thr Asn Glu Lys Phe
    130                 135                 140

Lys Glu Leu Phe Gly Ser Glu Gly Lys Asp Ile Leu Lys Glu Ile Leu
145                 150                 155                 160

Thr Asp Asn Thr Gly Asn Phe Lys Gly Leu Ile Glu Gly Lys Gly Lys
                165                 170                 175

Asp Glu Ala Lys Gly Val Leu Thr Asp Glu Lys Phe Lys Gly Leu Phe
            180                 185                 190

Asp Asp Lys Thr Ile Ala Gly Tyr Val Lys Glu Ile Leu Thr Ser Glu
        195                 200                 205

Lys Phe Lys Lys Leu Phe Glu Asn Gly Gly Lys Glu Lys Val Lys Glu
    210                 215                 220

Leu Leu Ile Asp Glu Asn Phe Lys Lys Leu Phe Glu Asp Asp Thr Lys
225                 230                 235                 240

Ala Ala His Val Lys Glu Ile Leu Thr Asp Ser Asn Ala Lys Glu Ile
                245                 250                 255

Leu Thr Asn Glu Val Ala Lys Glu Val Leu Lys Ser Asp Lys Phe Lys
            260                 265                 270

Asp Ala Ile Thr Gly Ala Gly Lys Asp Ala Leu Lys Glu Ile Leu Thr
        275                 280                 285

Cys Asp Lys Phe Lys Asp Ala Val Thr Gly Asn Gly Lys Asp Ala Leu
    290                 295                 300

Lys Glu Ile Leu Thr Cys Asp Lys Phe Lys Glu Ala Val Thr Gly Asp
305                 310                 315                 320

Gly Lys Asp Lys Leu Lys Glu Ile Leu Thr His Glu Lys Phe Lys Ala
                325                 330                 335

Leu Ile Glu Ser Glu Gly Lys Asp Ile Leu Lys Asp Ile Leu Thr Asp
            340                 345                 350

Ser Thr Gly Lys Phe Lys Glu Leu Ile Glu Ser Thr Gly Lys Asp Lys
        355                 360                 365

Leu Lys Glu Ile Leu Val Asp Glu Lys Phe Lys Ala Leu Phe Thr Asp
    370                 375                 380

Ala Thr Lys Ala Gly Tyr Val Lys Glu Ile Leu Thr Asp Ser Asn Ala
385                 390                 395                 400

Lys Glu Ile Leu Thr Asn Glu Val Ala Lys Glu Val Leu Lys Ser Asp
                405                 410                 415

Lys Phe Lys Asp Ala Ile Thr Gly Ala Gly Lys Asp Ala Leu Lys Glu
            420                 425                 430

Ile Leu Thr Cys Asp Lys Phe Lys Asp Ala Val Thr Gly Asn Gly Lys
        435                 440                 445

Asp Ala Leu Lys Glu Ile Leu Thr Cys Asp Lys Phe Lys Asp Ala Val
    450                 455                 460

Thr Gly Asn Gly Lys Asp Lys Leu Lys Glu Ile Leu Thr His Glu Lys
465                 470                 475                 480

Phe Lys Ala Leu Ile Glu Ser Glu Gly Lys Asp Ile Leu Lys Gly Ile
                485                 490                 495

Leu Thr Asp Ser Thr Gly Asn Phe Lys Gly Ala Ile Thr Gly Ala Gly
            500                 505                 510

Lys Asp Glu Leu Lys Asp Ile Leu Thr Asn Ser Glu Phe Lys Ser Leu
        515                 520                 525

Phe Glu Ser Lys Asp Ser Ala Glu Ala Val Lys Ala Ile Phe Thr Asn
    530                 535                 540

Ala Lys Phe Lys Gly Leu Leu Glu Thr Cys Lys Asn Asn Pro Lys Asn
```

-continued

```
545                 550                 555                 560

Thr Gln Ala Leu Glu Gly Ala Leu Asp Ser Leu Lys Glu Leu Leu Glu
                565                 570                 575

Val Asn Asp Asn Val Asn Tyr Gly Ser Lys Leu Lys Asp Phe Gly Gln
            580                 585                 590

Ser Leu Cys Thr Lys Arg Lys Glu Leu Asp Asp Gly Phe Thr Asn Pro
        595                 600                 605

Asn Cys Asn Ser Ile Val Val Thr Val Pro Asn Ser Thr His
    610                 615                 620


<210> SEQ ID NO 6
<211> LENGTH: 545
<212> TYPE: PRT
<213> ORGANISM: Ehrlichia risticii

<400> SEQUENCE: 6

Met Ser Asn Glu Thr Leu Leu Ser Val Leu Ser Asp Glu Thr His Phe
1               5                   10                  15

Ala Asn Leu Val Asp Glu Leu Leu Leu Ser Leu Val Lys Asp Ser Ile
            20                  25                  30

Phe Thr Gln Val Ile Lys Gly Glu Gly Lys Thr Glu Leu Lys Asp Ile
        35                  40                  45

Leu Thr Asp Ser Thr Gly Lys Phe Lys Glu Leu Ile Gly Ser Ser Gly
    50                  55                  60

Lys Asp Ile Leu Lys Ser Ile Leu Thr Asp Gly Ser Gly Asn Phe Lys
65                  70                  75                  80

Gly Leu Ile Glu Ser Thr Gly Lys Ala Glu Val Lys Glu Val Leu Thr
                85                  90                  95

Asn Glu Lys Phe Lys Glu Leu Phe Gly Ser Asp Gly Lys Asp Ile Leu
            100                 105                 110

Lys Asp Ile Leu Thr Asp Ser Thr Gly Lys Phe Lys Glu Leu Ile Gly
        115                 120                 125

Ser Ser Gly Lys Asp Ile Leu Lys Asn Ile Leu Thr Asp Ser Thr Gly
    130                 135                 140

Lys Phe Lys Glu Leu Ile Glu Ser Ala Gly Lys Gly Lys Leu Lys Asp
145                 150                 155                 160

Leu Leu Ile Asp Gly Asn Phe Lys Lys Leu Phe Glu Asp Asp Thr Lys
                165                 170                 175

Ala Ala His Val Lys Glu Ile Leu Thr Asp Ser Asn Ala Lys Glu Ile
            180                 185                 190

Leu Thr Asn Glu Val Ala Lys Glu Val Leu Lys Ser Asp Lys Phe Lys
        195                 200                 205

Asp Ala Ile Thr Gly Ala Gly Lys Asp Ala Leu Lys Glu Ile Leu Thr
    210                 215                 220

Cys Asp Lys Phe Lys Asp Ala Val Thr Gly Asn Gly Lys Asp Ala Leu
225                 230                 235                 240

Lys Glu Ile Leu Thr Cys Asp Lys Phe Lys Glu Ala Val Thr Gly Asp
                245                 250                 255

Gly Lys Asp Lys Leu Lys Glu Ile Leu Thr His Glu Lys Phe Lys Ala
            260                 265                 270

Leu Ile Glu Ser Glu Gly Lys Asp Ile Leu Lys Glu Ile Leu Thr Asp
        275                 280                 285

Ser Thr Gly Lys Phe Lys Glu Leu Ile Glu Ser Thr Gly Lys Asp Lys
    290                 295                 300
```

-continued

Leu Lys Glu Ile Leu Thr Asp Asn Thr Gly Asn Phe Lys Gly Leu Val
305 310 315 320

Glu Gly Ala Gly Lys Asp Glu Ala Lys Ala Val Leu Thr Asp Glu Lys
325 330 335

Phe Lys Gly Leu Phe Asp Asp Lys Thr Ile Ala Gly Tyr Val Lys Glu
340 345 350

Ile Leu Thr Ser Glu Lys Phe Lys Lys Leu Phe Glu Ser Ala Gly Lys
355 360 365

Thr Lys Val Lys Glu Leu Leu Ile Asp Glu Lys Phe Gln Lys Leu Phe
370 375 380

Glu Asp Asp Thr Lys Ala Ser His Val Lys Glu Ile Leu Thr Asn Asp
385 390 395 400

Thr Ala Lys Glu Ile Leu Thr Asn Asp Lys Phe Lys Glu Ala Ile Thr
405 410 415

Gly Asp Gly Lys Asp Ile Leu Lys Gly Ile Leu Thr Asp Ser Thr Gly
420 425 430

Asn Phe Lys Gly Ala Ile Thr Gly Ala Gly Lys Asp Glu Leu Lys Asp
435 440 445

Ile Leu Thr Asn Ser Glu Phe Lys Ser Leu Phe Asp Ser Lys Asp Ser
450 455 460

Ala Glu Ala Val Lys Ala Ile Phe Thr Asp Thr Lys Phe Lys Thr Leu
465 470 475 480

Leu Gln Thr Cys Lys Lys Asn Pro Asn Asn Thr Gln Ala Leu Ala Ala
485 490 495

Ala Leu Asp Glu Leu Lys Glu Leu Ile Thr Cys Gly Ser Asn Asp His
500 505 510

Ala Thr Lys Leu Gln Ala Phe Gly Asn Ala Leu Cys Asn Arg Lys Lys
515 520 525

Glu Thr Cys Ser Asn Phe Ser Ser Ala Asn Cys Thr Gly Thr Ala Ala
530 535 540

Thr
545

<210> SEQ ID NO 7
<211> LENGTH: 512
<212> TYPE: PRT
<213> ORGANISM: Ehrlichia risticii

<400> SEQUENCE: 7

Met Thr Asp Asp Thr Leu Leu Ser Val Leu Ser Asn Glu Thr His Phe
1 5 10 15

Asn Asn Leu Ile Asp Glu Phe Leu Leu Ser Leu Val Lys Asp Ala Met
20 25 30

Phe Asn Gln Val Ile Lys Gly Glu Gly Lys Thr Glu Leu Lys Asp Ile
35 40 45

Leu Thr Asp Thr Thr Gly Lys Phe Lys Glu Leu Ile Gly Gly Ser Gly
50 55 60

Lys Ala Ile Leu Lys Ser Ile Leu Thr Asp Asn Thr Gly Asn Phe Lys
65 70 75 80

Ala Leu Ile Glu Gly Asn Gly Lys Thr Gln Ala Lys Glu Val Leu Thr
85 90 95

His Glu Lys Phe Lys Glu Leu Phe Ser Thr Ala Asp Arg Ala Gly Ile
100 105 110

Ala Lys Glu Val Leu Thr Ala Glu Gln Phe Glu Lys Leu Leu Lys Gly
115 120 125

```
Ser Gly Lys Thr Gln Ala Lys Glu Val Leu Thr Asn Glu Asn Phe Asn
    130                 135                 140

Lys Leu Phe Asp Thr Thr Ser Ser Ala Lys Ile Ala Lys Glu Val Leu
145                 150                 155                 160

Thr Ala Glu Gln Phe Glu Lys Leu Leu Lys Gly Ser Gly Lys Thr Gln
                165                 170                 175

Ala Lys Glu Val Leu Thr Asn Lys Asn Phe Asn Lys Leu Phe Asp Thr
            180                 185                 190

Thr Gly Ser Ala Asp Ile Ala Lys Glu Val Leu Thr Ala Glu Gln Phe
        195                 200                 205

Glu Lys Leu Leu Lys Gly Ser Gly Lys Thr Gln Ala Lys Glu Val Leu
    210                 215                 220

Thr Asn Glu Asn Phe Asn Lys Leu Phe Asp Thr Thr Gly Ser Ala Asp
225                 230                 235                 240

Ile Ala Lys Glu Val Leu Thr Ala Glu Gln Phe Glu Lys Leu Leu Glu
                245                 250                 255

Gly Ser Gly Lys Asn Glu Ile Lys Glu Val Leu Thr Asn Glu Asn Phe
            260                 265                 270

Lys Lys Leu Phe Asp Thr Ala Asp Ser Ala Ser Ile Ala Lys Glu Val
        275                 280                 285

Leu Thr Ala Glu Gln Phe Glu Lys Leu Leu Glu Gly Ser Gly Lys Thr
    290                 295                 300

Gln Ala Lys Glu Val Leu Thr Asn Glu Asn Phe Lys Lys Leu Phe Glu
305                 310                 315                 320

Asn Ser Gly Arg Asp Ile Leu Lys Asp Ile Leu Thr Asp Ser Thr Gly
                325                 330                 335

Lys Phe Lys Glu Leu Ile Glu Ser Thr Gly Lys Glu Lys Val Lys Glu
            340                 345                 350

Leu Leu Ile Asp Gly Lys Phe Lys Asp Leu Phe Thr Asp Ala Thr Lys
        355                 360                 365

Ala Gly Tyr Val Lys Glu Ile Leu Thr Asn Asp Thr Ala Lys Asp Ile
    370                 375                 380

Leu Thr Asn Asp Lys Phe Lys Asp Ala Val Thr Gly Lys Gly Lys Asp
385                 390                 395                 400

Glu Leu Lys Ser Ile Leu Thr Asn Asp Asn Phe Lys Lys Leu Val Glu
                405                 410                 415

Ser Thr Ala Lys Asp Lys Val Lys Glu Val Leu Thr Asn Glu Asn Phe
            420                 425                 430

Gln Lys Leu Phe Asp Gln Thr Thr Lys Ala Gly His Val Lys Ser Ala
        435                 440                 445

Leu Thr Asp Glu Asn Phe Trp Asn Leu Phe Thr Lys Ser Asp Thr Glu
    450                 455                 460

Phe Ser Asn Tyr Ser Pro Phe Val Lys Thr Ile Ser Glu Leu Lys Asp
465                 470                 475                 480

Leu Ile His Cys Glu Asp Gly Lys His Glu Glu Lys Leu Lys Ala Phe
                485                 490                 495

Gly Asp Lys Leu Lys Glu Ala Lys Thr Pro Asp Ser Lys Lys Lys Asn
            500                 505                 510
```

<210> SEQ ID NO 8
<211> LENGTH: 512
<212> TYPE: PRT
<213> ORGANISM: Ehrlichia risticii -continued

<400> SEQUENCE: 8

```
Met Thr Asp Asp Thr Leu Leu Ser Val Leu Ser Asn Glu Thr His Phe
1               5                   10                  15

Asn Asn Leu Ile Asp Glu Phe Leu Leu Ser Leu Val Lys Asp Ala Met
            20                  25                  30

Phe Asn Gln Val Ile Lys Gly Glu Gly Lys Thr Glu Leu Lys Asp Ile
        35                  40                  45

Leu Thr Asp Thr Thr Gly Lys Phe Lys Glu Leu Ile Gly Gly Ser Gly
    50                  55                  60

Lys Ala Ile Leu Lys Ser Ile Leu Thr Asp Asn Thr Gly Asn Phe Lys
65                  70                  75                  80

Ala Leu Ile Glu Gly Asn Gly Lys Thr Gln Ala Lys Glu Val Leu Thr
                85                  90                  95

His Glu Lys Phe Lys Glu Leu Phe Ser Thr Ala Asp Arg Ala Gly Ile
            100                 105                 110

Ala Lys Glu Val Leu Thr Ala Glu Gln Phe Glu Lys Leu Leu Lys Gly
        115                 120                 125

Ser Gly Lys Thr Gln Ala Lys Glu Val Leu Thr Asn Glu Asn Phe Asn
    130                 135                 140

Lys Leu Phe Asp Thr Thr Ser Ser Ala Lys Ile Ala Lys Glu Val Leu
145                 150                 155                 160

Thr Ala Glu Gln Phe Glu Lys Leu Leu Lys Gly Ser Gly Lys Thr Gln
                165                 170                 175

Ala Lys Glu Val Leu Thr Asn Glu Asn Phe Asn Lys Leu Phe Asp Thr
            180                 185                 190

Thr Gly Ser Ala Asp Ile Ala Lys Glu Val Leu Thr Ala Glu Gln Phe
        195                 200                 205

Glu Lys Leu Leu Lys Gly Ser Gly Lys Thr Gln Ala Lys Glu Val Leu
    210                 215                 220

Thr Asn Glu Asn Phe Asn Lys Leu Phe Asp Thr Thr Gly Ser Ala Asp
225                 230                 235                 240

Ile Ala Lys Glu Val Leu Thr Ala Glu Gln Phe Glu Lys Leu Leu Glu
                245                 250                 255

Gly Ser Gly Lys Asn Glu Ile Lys Glu Val Leu Thr Asn Glu Asn Phe
            260                 265                 270

Lys Lys Leu Phe Asp Thr Ala Asp Ser Ala Ser Ile Ala Lys Glu Val
        275                 280                 285

Leu Thr Ala Glu Gln Phe Glu Lys Leu Leu Glu Gly Ser Gly Lys Thr
    290                 295                 300

Gln Ala Lys Glu Val Leu Thr Asn Glu Asn Phe Lys Lys Leu Phe Glu
305                 310                 315                 320

Asn Ser Gly Arg Asp Ile Leu Lys Asp Ile Leu Thr Asp Ser Thr Gly
                325                 330                 335

Lys Phe Lys Glu Leu Ile Glu Ser Thr Gly Lys Glu Lys Val Lys Glu
            340                 345                 350

Leu Leu Ile Asp Gly Lys Phe Lys Asp Leu Phe Thr Asp Ala Thr Lys
        355                 360                 365

Ala Gly Tyr Val Lys Glu Ile Leu Thr Asn Asp Thr Ala Lys Asp Ile
    370                 375                 380

Leu Thr Asn Asp Lys Phe Lys Asp Ala Val Thr Gly Lys Gly Lys Asp
385                 390                 395                 400

Glu Leu Lys Ser Ile Leu Thr Asn Asp Asn Phe Lys Lys Leu Val Glu
                405                 410                 415
```

-continued

```
Ser Thr Ala Lys Asp Lys Val Lys Glu Val Leu Thr Asn Glu Asn Phe
            420                 425                 430

Gln Lys Leu Phe Asp Gln Thr Thr Lys Ala Gly His Val Lys Ser Ala
        435                 440                 445

Leu Thr Asp Glu Asn Phe Trp Asn Leu Phe Val Lys Ser Lys Thr Glu
    450                 455                 460

Trp Ser Ser Asp Ser Pro Phe Val Lys Thr Ile Ser Glu Leu Lys Asp
465                 470                 475                 480

Leu Ile His Cys Glu Asp Gly Lys His Glu Glu Lys Leu Lys Ala Phe
                485                 490                 495

Gly Asp Lys Leu Lys Glu Ala Lys Thr Pro Asp Ser Lys Lys Lys Asn
            500                 505                 510


<210> SEQ ID NO 9
<211> LENGTH: 512
<212> TYPE: PRT
<213> ORGANISM: Ehrlichia risticii

<400> SEQUENCE: 9

Met Thr Asp Asp Thr Leu Leu Ser Val Leu Ser Asn Glu Thr His Phe
1               5                   10                  15

Asn Asn Leu Ile Asp Glu Phe Leu Leu Ser Leu Val Lys Asp Ala Met
            20                  25                  30

Phe Asn Gln Val Ile Lys Gly Glu Gly Lys Thr Glu Leu Lys Asp Ile
        35                  40                  45

Leu Thr Asp Thr Thr Gly Lys Phe Lys Glu Leu Ile Gly Gly Ser Gly
    50                  55                  60

Lys Ala Ile Leu Lys Ser Ile Leu Thr Asp Asn Thr Gly Asn Phe Lys
65                  70                  75                  80

Ala Leu Ile Glu Gly Asn Gly Lys Thr Gln Ala Lys Glu Val Leu Thr
                85                  90                  95

His Glu Lys Phe Lys Glu Leu Phe Ser Thr Ala Asp Arg Ala Gly Ile
            100                 105                 110

Ala Lys Glu Val Leu Thr Ala Glu Gln Phe Glu Lys Leu Leu Lys Gly
        115                 120                 125

Ser Gly Lys Thr Gln Ala Lys Glu Val Leu Thr Asn Glu Asn Phe Asn
    130                 135                 140

Lys Leu Phe Asp Thr Thr Ser Ser Ala Lys Ile Ala Lys Glu Val Leu
145                 150                 155                 160

Thr Ala Glu Gln Phe Glu Lys Leu Leu Lys Gly Ser Gly Lys Thr Gln
                165                 170                 175

Ala Lys Glu Val Leu Thr Asn Lys Asn Phe Asn Lys Leu Phe Asp Thr
            180                 185                 190

Thr Gly Ser Ala Asp Ile Ala Lys Glu Val Leu Thr Ala Glu Gln Phe
        195                 200                 205

Glu Lys Leu Leu Lys Gly Ser Gly Lys Thr Gln Ala Lys Glu Val Leu
    210                 215                 220

Thr Asn Glu Asn Phe Asn Lys Leu Phe Asp Thr Thr Gly Ser Ala Asp
225                 230                 235                 240

Ile Ala Lys Glu Val Leu Thr Ala Glu Gln Phe Glu Lys Leu Leu Glu
                245                 250                 255

Gly Ser Gly Lys Asn Glu Ile Lys Glu Val Leu Thr Asn Glu Asn Phe
            260                 265                 270

Lys Lys Leu Phe Asp Thr Ala Asp Ser Ala Ser Ile Ala Lys Glu Val
```

-continued

```
        275                 280                 285

Leu Thr Ala Glu Gln Phe Glu Lys Leu Leu Glu Gly Ser Gly Lys Thr
    290                 295                 300

Gln Ala Lys Glu Val Leu Thr Asn Glu Asn Phe Lys Lys Leu Phe Glu
305                 310                 315                 320

Asn Ser Gly Arg Asp Ile Leu Lys Asp Ile Leu Thr Asp Ser Thr Gly
                325                 330                 335

Lys Phe Lys Glu Leu Ile Glu Ser Thr Gly Lys Glu Lys Val Lys Glu
            340                 345                 350

Leu Leu Ile Asp Gly Lys Phe Lys Asp Leu Phe Thr Asp Ala Thr Lys
        355                 360                 365

Ala Gly Tyr Val Lys Glu Ile Leu Thr Asn Asp Thr Ala Lys Asp Ile
    370                 375                 380

Leu Thr Asn Asp Lys Phe Lys Asp Ala Val Thr Gly Lys Gly Lys Asp
385                 390                 395                 400

Glu Leu Lys Ser Ile Leu Thr Asn Asp Asn Phe Lys Lys Leu Val Glu
                405                 410                 415

Ser Thr Ala Lys Asp Lys Val Lys Glu Val Leu Thr Asn Glu Asn Phe
            420                 425                 430

Gln Lys Leu Phe Asp Gln Thr Thr Lys Ala Gly His Val Lys Ser Ala
        435                 440                 445

Leu Thr Asp Glu Asn Phe Trp Asn Leu Phe Val Lys Ser Lys Thr Glu
    450                 455                 460

Trp Ser Ser Asp Ser Pro Phe Val Lys Thr Ile Ser Glu Leu Lys Asp
465                 470                 475                 480

Leu Ile His Cys Glu Asp Gly Lys His Glu Glu Lys Leu Lys Ala Phe
                485                 490                 495

Gly Asp Lys Leu Lys Glu Ala Lys Thr Pro Asp Ser Lys Lys Lys Asn
            500                 505                 510


<210> SEQ ID NO 10
<211> LENGTH: 512
<212> TYPE: PRT
<213> ORGANISM: Ehrlichia risticii

<400> SEQUENCE: 10

Met Thr Asp Asp Thr Leu Leu Ser Val Leu Ser Asn Glu Thr His Phe
1               5                   10                  15

Asn Asn Leu Ile Asp Glu Phe Leu Leu Ser Leu Val Lys Asp Ala Met
            20                  25                  30

Phe Asn Gln Val Ile Lys Gly Glu Gly Lys Thr Glu Leu Lys Asp Ile
        35                  40                  45

Leu Thr Asp Thr Thr Gly Lys Phe Lys Glu Leu Ile Gly Gly Ser Gly
    50                  55                  60

Lys Ala Ile Leu Lys Ser Ile Leu Thr Asp Asn Thr Gly Asn Phe Lys
65                  70                  75                  80

Ala Leu Ile Glu Gly Asn Gly Lys Thr Gln Ala Lys Glu Val Leu Thr
                85                  90                  95

His Glu Lys Phe Lys Glu Leu Phe Ser Thr Ala Asp Arg Ala Gly Ile
            100                 105                 110

Ala Lys Glu Val Leu Thr Ala Glu Gln Phe Glu Lys Leu Leu Lys Gly
        115                 120                 125

Ser Gly Lys Thr Gln Ala Lys Glu Val Leu Thr Asn Glu Asn Phe Asn
    130                 135                 140
```

-continued

```
Lys Leu Phe Asp Thr Thr Ser Ser Ala Lys Ile Ala Lys Glu Val Leu
145                 150                 155                 160

Thr Ala Glu Gln Phe Glu Lys Leu Leu Lys Gly Ser Gly Lys Thr Gln
                165                 170                 175

Ala Lys Glu Val Leu Thr Asn Glu Asn Phe Asn Lys Leu Phe Asp Thr
            180                 185                 190

Thr Gly Ser Ala Asp Ile Ala Lys Glu Val Leu Thr Ala Glu Gln Phe
        195                 200                 205

Glu Lys Leu Leu Lys Gly Ser Gly Lys Thr Gln Ala Lys Glu Val Leu
    210                 215                 220

Thr Asn Glu Asn Phe Asn Lys Leu Phe Asp Thr Thr Gly Ser Ala Asp
225                 230                 235                 240

Ile Ala Lys Glu Val Leu Thr Ala Glu Gln Phe Glu Lys Leu Leu Glu
                245                 250                 255

Gly Ser Gly Lys Asn Glu Ile Lys Glu Val Leu Thr Asn Glu Asn Phe
            260                 265                 270

Lys Lys Leu Phe Asp Thr Ala Asp Ser Ala Ser Ile Ala Lys Glu Val
        275                 280                 285

Leu Thr Ala Glu Gln Phe Glu Lys Leu Leu Glu Gly Ser Gly Lys Thr
    290                 295                 300

Gln Ala Lys Glu Val Leu Thr Asn Glu Asn Phe Lys Lys Leu Phe Glu
305                 310                 315                 320

Asn Ser Gly Arg Asp Ile Leu Lys Asp Ile Leu Thr Asp Ser Thr Gly
                325                 330                 335

Lys Phe Lys Glu Leu Ile Glu Ser Thr Gly Lys Glu Lys Val Lys Glu
            340                 345                 350

Leu Leu Ile Asp Gly Lys Phe Lys Asp Leu Phe Thr Asp Ala Thr Lys
        355                 360                 365

Ala Gly Tyr Val Lys Glu Ile Leu Thr Asn Asp Thr Ala Lys Asp Ile
    370                 375                 380

Leu Thr Asn Asp Lys Phe Lys Asp Ala Val Thr Gly Lys Gly Lys Asp
385                 390                 395                 400

Glu Leu Lys Ser Ile Leu Thr Asn Asp Asn Phe Lys Lys Leu Val Glu
                405                 410                 415

Ser Thr Ala Lys Asp Lys Val Lys Glu Val Leu Thr Asn Glu Asn Phe
            420                 425                 430

Gln Lys Leu Phe Asp Gln Thr Thr Lys Ala Gly His Val Lys Ser Ala
        435                 440                 445

Leu Thr Asp Glu Asn Phe Trp Asn Leu Phe Thr Lys Ser Asp Thr Glu
    450                 455                 460

Phe Ser Asn Tyr Ser Pro Phe Val Lys Thr Ile Ser Glu Leu Lys Asp
465                 470                 475                 480

Leu Ile His Cys Glu Asp Gly Lys His Glu Glu Lys Leu Lys Ala Phe
                485                 490                 495

Gly Asp Lys Leu Lys Glu Ala Lys Thr Pro Asp Ser Lys Lys Lys Asn
            500                 505                 510
```

<210> SEQ ID NO 11
<211> LENGTH: 487
<212> TYPE: PRT
<213> ORGANISM: Ehrlichia risticii

<400> SEQUENCE: 11

```
Met Thr Asp Asp Thr Leu Leu Ser Val Leu Ser Asn Glu Thr His Phe
1               5                   10                  15
```

-continued

```
Ser Asn Leu Ile Asp Glu Ser Leu Leu Ser Leu Val Lys Asp Ala Met
            20                  25                  30

Phe Asn Gln Val Ile Lys Gly Glu Gly Lys Thr Glu Leu Lys Asp Ile
        35                  40                  45

Leu Thr Asp Ser Thr Gly Lys Phe Lys Glu Leu Ile Glu Gly Thr Gly
    50                  55                  60

Lys Asp Ile Leu Lys Ser Ile Leu Thr Asp Gly Ser Gly Asn Phe Lys
65                  70                  75                  80

Gly Leu Val Glu Ser Asn Gly Arg Thr Glu Ala Lys Glu Val Leu Thr
                85                  90                  95

His Gly Lys Phe Lys Glu Leu Phe Ser Thr Ser Asp Arg Ala Gly Val
            100                 105                 110

Thr Lys Glu Val Leu Thr Ala Glu Gln Phe Glu Lys Leu Leu Glu Gly
        115                 120                 125

Ser Gly Lys Thr Gln Ala Lys Glu Val Leu Thr Asn Lys Asn Phe Lys
    130                 135                 140

Lys Leu Phe Asp Thr Ala Asp Ser Ala Lys Ile Ala Lys Glu Val Leu
145                 150                 155                 160

Thr Ala Glu Gln Phe Glu Lys Leu Leu Glu Gly Ser Gly Lys Thr Gln
                165                 170                 175

Ala Lys Glu Val Leu Thr Asn Glu Asn Phe Lys Lys Leu Phe Asp Thr
            180                 185                 190

Ala Asp Ser Ala Gly Ile Val Lys Glu Val Leu Thr Ala Gln Gln Phe
        195                 200                 205

Lys Gln Leu Leu Lys Gly Ser Gly Lys Thr Gln Ala Lys Glu Val Leu
    210                 215                 220

Ile Asn Glu Asn Phe Ser Lys Leu Phe Asp Thr Ala Asp Arg Ala Gly
225                 230                 235                 240

Ile Ala Lys Glu Val Leu Thr Ala Glu Gln Phe Glu Lys Leu Leu Glu
                245                 250                 255

Gly Ser Gly Lys Thr Gln Val Lys Glu Val Leu Ile Ser Glu Asn Phe
            260                 265                 270

Lys Asn Leu Phe Glu Asn Gly Ala Lys Asp Lys Val Lys Asp Leu Leu
        275                 280                 285

Val Asp Lys Lys Phe Lys Glu Leu Phe Ala Asp Ala Thr Lys Ala Asp
    290                 295                 300

Tyr Val Lys Glu Ile Leu Thr Asp Ser Thr Ala Lys Glu Ile Leu Thr
305                 310                 315                 320

Asn Gln Thr Ala Lys Glu Val Leu Lys Asn Asp Thr Ala Lys Glu Val
                325                 330                 335

Leu Lys Cys Asp Lys Phe Lys Glu Ala Ile Ala Gly Thr Gly Lys Asp
            340                 345                 350

Ile Leu Lys Asp Ile Leu Thr Asp Ser Thr Gly Asn Phe Lys Arg Leu
        355                 360                 365

Ile Glu Gly Thr Gly Lys Glu Lys Val Lys Glu Leu Leu Thr Asp Glu
    370                 375                 380

Lys Phe Lys Lys Leu Met Glu Ser Thr Ala Lys Asp Ala Val Lys Glu
385                 390                 395                 400

Val Leu Thr Asn Glu Asn Phe Gln Lys Leu Phe Asn Gln Val Ile Lys
                405                 410                 415

Ala Gly His Val Lys Asn Ala Leu Ile Asn Glu Asn Phe Trp Asn Leu
            420                 425                 430
```

```
Phe Val Lys Gly Glu Lys Glu Trp Ser Asn Glu Ser Ser Phe Val Lys
        435                 440                 445

Thr Ile Ser Glu Leu Lys Asp Leu Ile His Cys Glu Asp Ser Gln His
    450                 455                 460

Glu Glu Lys Leu Lys Ala Phe Gly Asp Lys Leu Lys Lys Ala Lys Asn
465                 470                 475                 480

Pro Asn Gln Lys Lys Glu Lys
                485


<210> SEQ ID NO 12
<211> LENGTH: 469
<212> TYPE: PRT
<213> ORGANISM: Ehrlichia risticii

<400> SEQUENCE: 12

Met Thr Asp Asp Thr Leu Leu Ser Val Leu Ser Asn Glu Thr His Phe
1               5                   10                  15

Asn Asn Leu Ile Asp Glu Phe Leu Leu Ser Leu Val Lys Asp Ala Met
            20                  25                  30

Phe Asn Gln Val Ile Lys Gly Glu Gly Lys Thr Glu Leu Lys Asp Ile
        35                  40                  45

Leu Thr Asp Thr Thr Gly Lys Phe Lys Glu Leu Ile Gly Gly Ser Gly
    50                  55                  60

Lys Ala Ile Leu Lys Ser Ile Leu Thr Asp Asn Thr Gly Asn Phe Lys
65                  70                  75                  80

Ala Leu Ile Glu Gly Asn Gly Lys Thr Gln Ala Lys Glu Val Leu Thr
                85                  90                  95

His Glu Lys Phe Lys Glu Leu Phe Ser Thr Ala Asp Arg Ala Gly Ile
            100                 105                 110

Ala Lys Glu Val Leu Thr Ala Glu Gln Phe Glu Lys Leu Leu Lys Gly
        115                 120                 125

Ser Gly Lys Thr Gln Ala Lys Glu Val Leu Thr Asn Glu Asn Phe Asn
    130                 135                 140

Lys Leu Phe Asp Thr Thr Ser Ser Ala Lys Ile Ala Lys Glu Val Leu
145                 150                 155                 160

Thr Ala Glu Gln Phe Glu Lys Leu Leu Lys Gly Ser Gly Lys Thr Gln
                165                 170                 175

Ala Lys Glu Val Leu Thr Asn Glu Asn Phe Asn Lys Leu Phe Asp Thr
            180                 185                 190

Thr Gly Ser Ala Asp Ile Ala Lys Glu Val Leu Thr Ala Glu Gln Phe
        195                 200                 205

Glu Lys Leu Leu Lys Gly Ser Gly Lys Thr Gln Ala Lys Glu Val Leu
    210                 215                 220

Thr Asn Glu Asn Phe Asn Lys Leu Phe Asp Thr Thr Gly Ser Ala Asp
225                 230                 235                 240

Ile Ala Lys Glu Val Leu Thr Ala Glu Gln Phe Glu Lys Leu Leu Glu
                245                 250                 255

Gly Ser Gly Lys Thr Gln Ala Lys Glu Val Leu Thr Asn Glu Asn Phe
            260                 265                 270

Lys Lys Leu Phe Glu Asn Ser Gly Arg Asp Ile Leu Lys Asp Ile Leu
        275                 280                 285

Thr Asp Ser Thr Gly Lys Phe Lys Glu Leu Ile Glu Ser Thr Gly Lys
    290                 295                 300

Glu Lys Val Lys Glu Leu Leu Ile Asp Gly Lys Phe Lys Asp Leu Phe
305                 310                 315                 320
```

Thr Asp Ala Thr Lys Ala Gly Tyr Val Lys Glu Ile Leu Thr Asn Asp
325 330 335

Thr Ala Lys Asp Ile Leu Thr Asn Asp Lys Phe Lys Asp Ala Val Thr
340 345 350

Gly Lys Gly Lys Asp Glu Leu Lys Ser Ile Leu Thr Asn Asp Asn Phe
355 360 365

Lys Lys Leu Val Glu Ser Thr Ala Lys Asp Lys Val Lys Glu Val Leu
370 375 380

Thr Asn Glu Asn Phe Gln Lys Leu Phe Asp Gln Thr Thr Lys Ala Gly
385 390 395 400

His Val Lys Ser Ala Leu Thr Asp Glu Asn Phe Trp Asn Leu Phe Thr
405 410 415

Lys Ser Asp Thr Glu Phe Ser Asn Tyr Ser Pro Phe Val Lys Thr Ile
420 425 430

Ser Glu Leu Lys Asp Leu Ile His Cys Glu Asp Gly Lys His Glu Glu
435 440 445

Lys Leu Lys Ala Phe Gly Asp Lys Leu Lys Glu Ala Lys Thr Pro Asp
450 455 460

Ser Lys Lys Lys Asn
465

<210> SEQ ID NO 13
<211> LENGTH: 433
<212> TYPE: PRT
<213> ORGANISM: Ehrlichia risticii

<400> SEQUENCE: 13

Met Ala Gly Asp Thr Leu Leu Ser Val Leu Ser Asp Glu Thr His Phe
1 5 10 15

Glu Asn Leu Thr Asp Gly Ile Phe Leu Ser Leu Val Lys Asp Pro Asn
20 25 30

Phe Ala Ser Ala Ser Lys Gly Val Ser Lys Ala Glu Leu Lys Asp Val
35 40 45

Leu Thr Ser Glu Asn Phe Lys Gly Leu Phe Glu Asp Gln Ala Lys Ala
50 55 60

Gln Asn Val Val Ala Val Leu Lys Asp Ser Ile Ala Lys Ala Val Leu
65 70 75 80

Glu Ser Asp Lys Phe Lys Ala Leu Leu Gln Thr Gln Gly Lys Ala Glu
85 90 95

Leu Gln Asp Leu Leu Thr Asn Asp Asn Phe Lys Gly Leu Phe Glu Asp
100 105 110

Gln Ala Lys Ala Gln Asn Val Val Ala Val Leu Lys Asp Ser Ile Ala
115 120 125

Lys Ala Val Leu Glu Ser Asp Lys Phe Lys Ala Leu Leu Gln Thr Gln
130 135 140

Gly Lys Ala Glu Leu Gln Asp Leu Leu Thr Asn Asp Asn Phe Lys Gly
145 150 155 160

Leu Phe Glu Asp Gln Ala Lys Ala Ser Ser Ile Lys Thr Ile Leu Thr
165 170 175

Asn Gln Asn Ala Thr Gly Val Leu Thr Asp Gly Thr Ala Ser Asn Val
180 185 190

Ile Thr Asn Asp Thr Ala Lys Glu Val Leu Lys Asn Ala Asn Ala Ala
195 200 205

Glu Leu Leu Lys Asp Asn Asn Ala Ala Glu Val Leu Lys Asp Glu Thr

```
    210                 215                 220

Ala Lys Glu Ile Leu Lys Asn Ile Lys Phe Lys Glu Ile Leu Lys Gly
225                 230                 235                 240

Ala Gly Lys Asp Ile Ile Lys Asn Ile Leu Thr Asp Gly Thr Gly Thr
                245                 250                 255

Phe Lys Gly Leu Leu Glu Cys Ala Gly Lys Asp Lys Val Gly Asn Val
            260                 265                 270

Leu Thr Asn Gln Thr Phe Lys Lys Leu Phe Glu Ser Pro Gly Asn Glu
        275                 280                 285

Glu Ile Lys Asp Ile Leu Ile Asn Glu Asn Phe Glu Ser Ser Phe Glu
    290                 295                 300

Asn Lys Glu Ser Ala Gln Lys Leu Lys Asp Ser Leu Thr Ala Lys Thr
305                 310                 315                 320

Val Lys Thr Leu Phe Gly Asp Pro Val Lys Ala Glu Arg Ala Lys Asn
                325                 330                 335

Leu Phe Thr Asn Thr Asn Phe Ala Glu Leu Leu Gln His Asn Lys Leu
            340                 345                 350

Asn Asp Leu Val Asn Asn Gln His Phe Thr Asn Leu Phe Lys Asn Glu
        355                 360                 365

Thr Thr Ala Arg His Ala Thr Glu Ile Leu Thr Ser Pro His Phe Lys
    370                 375                 380

Ala Ser Leu Glu Asn Asn Glu Ala Val Thr Asn Leu Lys Lys Leu Leu
385                 390                 395                 400

Thr His Ser Ala Leu Arg Glu Leu Phe Ser Asn Asp Asn Leu Glu Asn
                405                 410                 415

Ala Thr Ser Phe Ala Lys Lys Leu Arg Glu Leu Gly Ile Val Arg Thr
            420                 425                 430

Arg


<210> SEQ ID NO 14
<211> LENGTH: 537
<212> TYPE: PRT
<213> ORGANISM: Ehrlichia risticii

<400> SEQUENCE: 14

Met Ala Gly Asp Thr Leu Leu Ser Val Leu Ser Asp Glu Thr His Phe
1               5                   10                  15

Glu Asn Leu Thr Asp Gly Ile Phe Leu Ser Leu Val Lys Asp Pro Asn
            20                  25                  30

Phe Ala Ser Ala Ser Lys Gly Val Ser Lys Ala Glu Leu Lys Asp Val
        35                  40                  45

Leu Thr Ser Glu Asn Phe Lys Gly Leu Phe Glu Asp Gln Ala Lys Ala
    50                  55                  60

Gln Asn Val Val Ala Val Leu Lys Asp Ser Ile Ala Lys Thr Val Leu
65                  70                  75                  80

Glu Ser Asp Lys Phe Lys Ala Leu Leu Gln Thr Gln Gly Lys Ala Glu
                85                  90                  95

Leu Gln Asp Leu Leu Thr Asn Asp Asn Phe Lys Gly Leu Phe Glu Asp
            100                 105                 110

Gln Ala Lys Ala Gln Asn Val Val Ala Val Leu Lys Asp Ser Ile Ala
        115                 120                 125

Lys Ala Val Leu Glu Ser Asp Lys Phe Lys Ala Leu Leu Gln Thr Gln
    130                 135                 140

Gly Lys Ala Glu Leu Gln Asp Leu Leu Thr Asn Asp Asn Phe Lys Gly
```

-continued

```
145                 150                 155                 160

Leu Phe Glu Asp Gln Ala Lys Ala Gln Asn Val Val Ala Val Leu Lys
                165                 170                 175

Asp Ser Ile Ala Lys Ala Val Leu Glu Ser Asp Lys Phe Lys Ala Leu
            180                 185                 190

Leu Gln Thr Gln Gly Lys Ala Glu Leu Gln Asp Leu Leu Thr Asn Asp
        195                 200                 205

Asn Phe Lys Gly Leu Phe Glu Asp Gln Ala Lys Ala Gln Asn Val Val
    210                 215                 220

Ala Val Leu Lys Asp Ser Ile Ala Lys Ala Val Leu Glu Ser Asp Lys
225                 230                 235                 240

Phe Lys Ala Leu Leu Gln Thr Gln Gly Lys Ala Glu Leu Gln Asp Leu
                245                 250                 255

Leu Thr Asn Asp Asn Phe Lys Gly Leu Phe Glu Asp Gln Ala Lys Ala
            260                 265                 270

Ser Ser Ile Lys Thr Ile Leu Thr Asn Gln Asn Ala Thr Gly Val Leu
        275                 280                 285

Thr Asp Gly Thr Ala Ser Asn Val Ile Thr Asn Asn Thr Ala Lys Glu
    290                 295                 300

Val Leu Lys Asn Ala Asn Ala Ala Glu Leu Leu Lys Asp Asn Asn Ala
305                 310                 315                 320

Ala Glu Val Leu Lys Asp Glu Thr Ala Lys Glu Ile Leu Lys Asn Ile
                325                 330                 335

Lys Phe Lys Glu Ile Leu Lys Gly Ala Gly Lys Asp Ile Ile Lys Asn
            340                 345                 350

Ile Leu Thr Asp Gly Thr Gly Thr Phe Lys Gly Leu Leu Glu Cys Ala
        355                 360                 365

Gly Lys Asp Lys Val Gly Asn Val Leu Thr Asn Gln Thr Phe Lys Lys
    370                 375                 380

Leu Phe Glu Ser Pro Gly Asn Glu Glu Ile Lys Asp Ile Leu Ile Asn
385                 390                 395                 400

Glu Asn Phe Glu Ser Ser Phe Glu Asn Lys Glu Ser Ala Gln Lys Leu
                405                 410                 415

Lys Asp Ser Leu Thr Ala Lys Thr Val Lys Thr Leu Phe Gly Asp Pro
            420                 425                 430

Val Lys Ala Glu Arg Ala Lys Asn Leu Phe Thr Asn Thr Asn Phe Ala
        435                 440                 445

Glu Leu Leu Gln His Asn Lys Leu Asn Asp Leu Val Asn Asn Gln His
    450                 455                 460

Phe Thr Asn Leu Phe Lys Asn Glu Thr Thr Ala Arg His Ala Thr Glu
465                 470                 475                 480

Ile Leu Thr Ser Pro His Phe Lys Ala Ser Leu Glu Asn Asn Glu Ala
                485                 490                 495

Val Thr Asn Leu Lys Lys Leu Leu Thr His Ser Ala Leu Arg Glu Leu
            500                 505                 510

Phe Ser Asn Asp Asn Leu Glu Asn Ala Thr Ser Phe Ala Lys Lys Leu
        515                 520                 525

Arg Glu Leu Gly Ile Val Arg Thr Arg
    530                 535
```

<210> SEQ ID NO 15
<211> LENGTH: 537
<212> TYPE: PRT
<213> ORGANISM: Ehrlichia risticii -continued

<400> SEQUENCE: 15

```
Met Ala Gly Asp Thr Leu Leu Ser Val Leu Ser Asp Glu Thr His Phe
1               5                   10                  15

Glu Asn Leu Thr Asp Gly Ile Phe Leu Ser Leu Val Lys Asp Pro Asn
            20                  25                  30

Phe Ala Ser Ala Ser Lys Gly Val Ser Lys Ala Glu Leu Lys Asp Val
        35                  40                  45

Leu Thr Ser Glu Asn Phe Lys Gly Leu Phe Glu Asp Gln Ala Lys Ala
    50                  55                  60

Gln Asn Val Val Ala Val Leu Lys Asp Ser Ile Ala Lys Thr Val Leu
65                  70                  75                  80

Glu Ser Asp Lys Phe Lys Ala Leu Leu Gln Thr Gln Gly Lys Ala Glu
                85                  90                  95

Leu Gln Asp Leu Leu Thr Asn Asp Asn Phe Lys Gly Leu Phe Glu Asp
            100                 105                 110

Gln Ala Lys Ala Gln Asn Val Val Ala Val Leu Lys Asp Ser Ile Ala
        115                 120                 125

Lys Ala Val Leu Glu Ser Asp Lys Phe Lys Ala Leu Leu Gln Thr Gln
    130                 135                 140

Gly Lys Ala Glu Leu Gln Asp Leu Leu Thr Asn Asp Asn Phe Lys Gly
145                 150                 155                 160

Leu Phe Glu Asp Gln Ala Lys Ala Gln Asn Val Val Ala Val Leu Lys
                165                 170                 175

Asp Ser Ile Ala Lys Ala Val Leu Glu Ser Asp Lys Phe Lys Ala Leu
            180                 185                 190

Leu Gln Thr Gln Gly Lys Ala Glu Leu Gln Asp Leu Leu Thr Asn Asp
        195                 200                 205

Asn Phe Lys Gly Leu Phe Glu Asp Gln Ala Lys Ala Gln Asn Val Val
    210                 215                 220

Ala Val Leu Lys Asp Ser Ile Ala Lys Ala Val Leu Glu Ser Asp Lys
225                 230                 235                 240

Phe Lys Ala Leu Leu Gln Thr Gln Gly Lys Ala Glu Leu Gln Asp Leu
                245                 250                 255

Leu Thr Asn Asp Asn Phe Lys Gly Leu Phe Glu Asp Gln Ala Lys Ala
            260                 265                 270

Ser Ser Ile Lys Thr Ile Leu Thr Asn Gln Asn Ala Thr Gly Val Leu
        275                 280                 285

Thr Asp Gly Thr Ala Ser Asn Val Ile Thr Asn Asn Thr Ala Lys Glu
    290                 295                 300

Val Leu Lys Asn Ala Asn Ala Ala Glu Leu Leu Lys Asp Asn Asn Ala
305                 310                 315                 320

Ala Glu Val Leu Lys Asp Glu Thr Ala Lys Glu Ile Leu Lys Asn Ile
                325                 330                 335

Lys Phe Lys Glu Ile Leu Lys Gly Ala Gly Lys Asp Ile Ile Lys Asn
            340                 345                 350

Ile Leu Thr Asp Gly Thr Gly Thr Phe Lys Gly Leu Leu Glu Cys Ala
        355                 360                 365

Gly Lys Asp Lys Val Gly Asn Val Leu Thr Asn Gln Thr Phe Lys Lys
    370                 375                 380

Leu Phe Glu Ser Pro Gly Asn Glu Glu Ile Lys Asp Ile Leu Ile Asn
385                 390                 395                 400

Glu Asn Phe Glu Ser Ser Phe Glu Asn Lys Glu Ser Ala Gln Lys Leu
```

```
                405                 410                 415

Lys Asp Ser Leu Thr Ala Lys Thr Val Lys Thr Leu Phe Gly Asp Pro
            420                 425                 430

Val Lys Ala Glu Arg Ala Lys Asn Leu Phe Thr Asn Thr Asn Phe Ala
        435                 440                 445

Glu Leu Leu Gln His Asn Lys Leu Asn Asp Leu Val Asn Asn Gln His
    450                 455                 460

Phe Thr Asn Leu Phe Lys Asn Glu Thr Thr Ala Arg His Ala Thr Glu
465                 470                 475                 480

Ile Leu Thr Ser Pro His Phe Lys Ala Ser Leu Glu Asn Asn Glu Ala
                485                 490                 495

Val Thr Asn Leu Lys Lys Leu Leu Thr His Ser Ala Leu Arg Glu Leu
            500                 505                 510

Phe Ser Asn Asp Asn Leu Glu Asn Ala Thr Ser Phe Ala Lys Lys Leu
        515                 520                 525

Arg Glu Leu Gly Ile Val Arg Thr Arg
    530                 535


<210> SEQ ID NO 16
<211> LENGTH: 433
<212> TYPE: PRT
<213> ORGANISM: Ehrlichia risticii

<400> SEQUENCE: 16

Met Ala Gly Asp Thr Leu Leu Ser Val Leu Ser Asp Glu Thr His Phe
1               5                   10                  15

Glu Asn Leu Thr Asp Gly Ile Phe Leu Ser Leu Val Lys Asp Pro Asn
            20                  25                  30

Phe Ala Ser Ala Ser Lys Gly Val Ser Lys Ala Glu Leu Lys Asp Val
        35                  40                  45

Leu Thr Ser Glu Asn Phe Lys Gly Leu Phe Glu Asp Gln Ala Lys Ala
    50                  55                  60

Gln Asn Val Val Ala Val Leu Lys Asp Ser Ile Ala Lys Thr Val Leu
65                  70                  75                  80

Glu Ser Asp Lys Phe Lys Ala Leu Leu Gln Thr Gln Gly Lys Ala Glu
                85                  90                  95

Leu Gln Asp Leu Leu Thr Asn Asp Asn Phe Lys Gly Leu Phe Glu Asp
            100                 105                 110

Gln Ala Lys Ala Gln Asn Val Val Ala Val Leu Lys Asp Ser Ile Ala
        115                 120                 125

Lys Ala Val Leu Glu Ser Asp Lys Phe Lys Ala Leu Leu Gln Thr Gln
    130                 135                 140

Gly Lys Ala Glu Leu Gln Asp Leu Leu Thr Asn Asp Asn Phe Lys Gly
145                 150                 155                 160

Leu Phe Glu Asp Gln Ala Lys Ala Ser Ser Ile Lys Thr Ile Leu Thr
                165                 170                 175

Asn Gln Asn Ala Thr Gly Val Leu Thr Asp Gly Thr Ala Ser Asn Val
            180                 185                 190

Ile Thr Asn Asp Thr Ala Lys Glu Val Leu Lys Asn Ala Asn Ala Ala
        195                 200                 205

Glu Leu Leu Lys Asp Asn Asn Ala Ala Glu Val Leu Lys Asp Glu Thr
    210                 215                 220

Ala Lys Glu Ile Leu Lys Asn Ile Lys Phe Lys Glu Ile Leu Lys Gly
225                 230                 235                 240
```

-continued

```
Ala Gly Lys Asp Ile Ile Lys Asn Ile Leu Thr Asp Gly Thr Gly Thr
                245                 250                 255

Phe Lys Gly Leu Leu Glu Cys Ala Gly Lys Asp Lys Val Gly Asn Val
            260                 265                 270

Leu Thr Asn Gln Thr Phe Lys Lys Leu Phe Glu Ser Pro Gly Asn Glu
        275                 280                 285

Glu Ile Lys Asp Ile Leu Ile Asn Glu Asn Phe Glu Ser Ser Phe Glu
    290                 295                 300

Asn Lys Glu Ser Ala Gln Lys Leu Lys Asp Ser Leu Thr Ala Lys Thr
305                 310                 315                 320

Val Lys Thr Leu Phe Gly Asp Pro Val Lys Ala Glu Arg Ala Lys Asn
                325                 330                 335

Leu Phe Thr Asn Thr Asn Phe Ala Glu Leu Leu Gln His Asn Lys Leu
            340                 345                 350

Asn Asp Leu Val Asn Asn Gln His Phe Thr Asn Leu Phe Lys Asn Glu
        355                 360                 365

Thr Thr Ala Arg His Ala Thr Glu Ile Leu Thr Ser Pro His Phe Lys
    370                 375                 380

Ala Ser Leu Glu Asn Asn Glu Ala Val Thr Asn Leu Lys Lys Leu Leu
385                 390                 395                 400

Thr His Ser Ala Leu Arg Glu Leu Phe Ser Asn Asp Asn Leu Glu Asn
                405                 410                 415

Ala Thr Ser Phe Ala Lys Lys Leu Arg Glu Leu Gly Ile Val Arg Thr
            420                 425                 430

Arg


<210> SEQ ID NO 17
<211> LENGTH: 485
<212> TYPE: PRT
<213> ORGANISM: Ehrlichia risticii

<400> SEQUENCE: 17

Met Ala Gly Asp Thr Leu Leu Ser Val Leu Ser Asp Glu Thr His Phe
1               5                   10                  15

Glu Asn Leu Thr Asp Gly Ile Phe Leu Ser Leu Val Lys Asp Pro Asn
            20                  25                  30

Phe Ala Ser Ala Ser Lys Gly Val Ser Lys Ala Glu Leu Lys Asp Val
        35                  40                  45

Leu Thr Ser Glu Asn Phe Lys Gly Leu Phe Glu Asp Gln Ala Lys Ala
    50                  55                  60

Gln Asn Val Val Ala Val Leu Lys Asp Ser Ile Ala Lys Ala Val Leu
65                  70                  75                  80

Glu Ser Asp Lys Phe Lys Ala Leu Leu Gln Thr Gln Gly Lys Ala Glu
                85                  90                  95

Leu Gln Asp Leu Leu Thr Asn Asp Asn Phe Lys Gly Leu Phe Glu Asp
            100                 105                 110

Gln Ala Lys Ala Gln Asn Val Val Ala Val Leu Lys Asp Ser Ile Ala
        115                 120                 125

Lys Ala Val Leu Glu Ser Asp Lys Phe Lys Ala Leu Leu Gln Thr Gln
    130                 135                 140

Gly Lys Ala Glu Leu Gln Asp Leu Leu Thr Asn Asp Asn Phe Lys Gly
145                 150                 155                 160

Leu Phe Glu Asp Gln Ala Lys Ala Gln Asn Val Val Ala Val Leu Lys
                165                 170                 175
```

```
Asp Ser Ile Ala Lys Ala Val Leu Glu Ser Asp Lys Phe Lys Ala Leu
            180                 185                 190

Leu Gln Thr Gln Gly Lys Ala Glu Leu Gln Asp Leu Leu Thr Asn Asp
        195                 200                 205

Asn Phe Lys Gly Leu Phe Glu Asp Gln Ala Lys Ala Ser Ser Ile Lys
    210                 215                 220

Thr Ile Leu Thr Asn Gln Asn Ala Thr Gly Val Leu Thr Asp Gly Thr
225                 230                 235                 240

Ala Ser Asn Val Ile Thr Asn Asn Thr Ala Lys Glu Val Leu Lys Asn
                245                 250                 255

Ala Asn Ala Ala Glu Leu Leu Lys Asp Asn Asn Ala Ala Glu Val Leu
            260                 265                 270

Lys Asp Glu Thr Ala Lys Glu Ile Leu Lys Asn Ile Lys Phe Lys Glu
        275                 280                 285

Ile Leu Lys Gly Ala Gly Lys Asp Ile Ile Lys Asn Ile Leu Thr Asp
    290                 295                 300

Gly Thr Gly Thr Phe Lys Gly Leu Leu Glu Cys Ala Gly Lys Asp Lys
305                 310                 315                 320

Val Gly Asn Val Leu Thr Asn Gln Thr Phe Lys Lys Leu Phe Glu Ser
                325                 330                 335

Pro Gly Asn Glu Glu Ile Lys Asp Ile Leu Ile Asn Glu Asn Phe Glu
            340                 345                 350

Ser Ser Phe Glu Asn Lys Glu Ser Ala Gln Lys Leu Lys Asp Ser Leu
        355                 360                 365

Thr Ala Lys Thr Val Lys Thr Leu Phe Gly Asp Pro Val Lys Ala Glu
    370                 375                 380

Arg Ala Lys Asn Leu Phe Thr Asn Thr Asn Phe Ala Glu Leu Leu Gln
385                 390                 395                 400

His Asn Lys Leu Asn Asp Leu Val Asn Asn Gln His Phe Thr Asn Leu
                405                 410                 415

Phe Lys Asn Glu Thr Thr Ala Arg His Ala Thr Glu Ile Leu Thr Ser
            420                 425                 430

Pro His Phe Lys Ala Ser Leu Glu Asn Asn Glu Ala Val Thr Asn Leu
        435                 440                 445

Lys Lys Leu Leu Thr His Ser Ala Leu Arg Glu Leu Phe Ser Asn Asp
    450                 455                 460

Asn Leu Glu Asn Ala Thr Ser Phe Ala Lys Lys Leu Arg Glu Leu Gly
465                 470                 475                 480

Ile Val Arg Thr Arg
                485


<210> SEQ ID NO 18
<211> LENGTH: 434
<212> TYPE: PRT
<213> ORGANISM: Ehrlichia risticii

<400> SEQUENCE: 18

Met Val Gly Asp Thr Leu Leu Ser Val Leu Ser Asp Glu Thr His Phe
1               5                   10                  15

Glu Asn Leu Ile Asp Gly Ile Phe Leu Ser Leu Val Lys Asp Pro Asn
            20                  25                  30

Phe Ala Ser Ala Ser Lys Gly Val Ser Lys Val Glu Leu Lys Asp Val
        35                  40                  45

Leu Thr Ser Glu Asn Phe Lys Gly Leu Phe Glu Asp Gln Ala Lys Ala
    50                  55                  60
```

-continued

Gln Asn Val Ala Ala Val Leu Lys Asp Ser Ala Ala Lys Ala Val Leu
65 70 75 80

Glu Ser Asp Lys Phe Lys Ala Leu Leu Gln Thr Gln Gly Lys Ala Glu
85 90 95

Leu Gln Asp Leu Leu Thr Asn Glu Asn Phe Lys Gly Leu Phe Glu Asp
100 105 110

Gln Ala Lys Ala Gln Asn Val Ala Ala Val Leu Lys Asp Ser Ala Ala
115 120 125

Lys Ala Val Leu Glu Ser Asp Lys Phe Lys Ala Leu Leu Gln Thr Gln
130 135 140

Gly Lys Ala Glu Leu Gln Asp Leu Leu Thr Asn Glu Asn Phe Lys Gly
145 150 155 160

Leu Phe Glu Asp Gln Ala Lys Ala Ser Ser Ala Lys Thr Ile Leu Thr
165 170 175

Asn Gln Asn Ala Ile Gly Val Leu Thr Asn Gly Thr Ala Ser Ala Val
180 185 190

Ile Met Asn Asp Thr Ala Lys Glu Val Leu Lys Asn Ala Asn Ser Ala
195 200 205

Glu Leu Leu Lys Asp Ser Thr Ala Ala Glu Ile Leu Lys Asp Glu Thr
210 215 220

Thr Lys Glu Val Leu Lys Ser Ser Lys Phe Lys Glu Ile Leu Lys Gly
225 230 235 240

Ala Gly Lys Asp Thr Ile Lys Asn Ile Leu Thr Asp Ser Thr Gly Thr
245 250 255

Phe Lys Glu Leu Val Glu Cys Ala Gly Lys Asp Lys Val Glu Asn Val
260 265 270

Leu Thr Asn Gln Thr Phe Lys Lys Leu Phe Glu Ser Pro Gly Asn Glu
275 280 285

Glu Ile Lys Asp Ile Leu Thr Asn Glu Asn Phe Glu Leu Ser Phe Glu
290 295 300

Asn Lys Lys Ser Ala Glu Lys Leu Lys Glu Thr Leu Thr Arg Pro Ile
305 310 315 320

Ile Lys Glu Leu Phe Ser Asp Pro Val Lys Ala Glu Arg Val Gly Asp
325 330 335

Leu Phe Thr Asn Asp Asn Phe Ile Glu Leu Leu Gln His Gly Lys Leu
340 345 350

Asn Asp Leu Val Asn Asn Gln His Phe Thr Asn Leu Phe Lys Asn Glu
355 360 365

Thr Thr Ala Gly His Ala Thr Glu Ile Leu Thr Ser Pro His Phe Lys
370 375 380

Ala Ser Leu Glu Asn Asn Glu Ala Val Ala Asn Leu Lys Lys Leu Leu
385 390 395 400

Thr Asn Ser Ala Leu Arg Glu Leu Phe Ser Asn Asp Asn Leu Glu Asp
405 410 415

Ala Thr Ser Phe Ala Lys Lys Leu Val Glu Leu Gly Ile Ile Ala Arg
420 425 430

Ile Lys

<210> SEQ ID NO 19
<211> LENGTH: 1302
<212> TYPE: DNA
<213> ORGANISM: Ehrlichia risticii

<400> SEQUENCE: 19
atggcaggtg atacactttt gagcgtactt tccgatgaaa cgcactttga aaatctaaca 60
gatggaatct tcctcagctt ggttaaggat ccgaattttg ctagtgcatc aaaaggcgtg 120
agtaaggcag agttgaaaga tgtactcact agcgaaaact ttaagggact atttgaagat 180
caagctaaag cacaaaatgt agtcgcagta ctgaaagact caatagcaaa ggcagtactg 240
gaaagcgata aattcaaggc gctgcttcag acacaaggta aagctgagtt gcaagattta 300
ctaaccaatg acaattttaa gggactattt gaagatcaag ctaaagcaca aaatgtagtc 360
gcagtactga aagactcaat agcaaaggca gtactggaaa gcgataaatt caaggcgctg 420
cttcagacac aaggtaaagc tgagttgcaa gatttactaa ccaatgacaa ttttaaggga 480
ctatttgaag atcaagctaa agccagcagc ataaaaacca tactaaccaa ccaaaatgca 540
acaggtgttc ttaccgatgg tacagctagt aatgttataa cgaatgacac tgccaaagaa 600
gtactaaaga atgcaaatgc agctgaattg cttaaggaca acaacgcagc tgaagtacta 660
aaagatgaga cagcaaagga aatattgaaa aacatcaagt ttaaggaaat tttaaaaggt 720
gcgggcaaag acataataaa aaatatcctc acagatggca ctggtacttt taaaggactt 780
ctcgaatgtg caggaaaaga taaagtaggc aatgttctca caaatcagac tttcaaaaag 840
ctgttcgaaa gtccaggtaa tgaggaaata aaagatatcc tcattaacga aaatttcgag 900
tcatcattcg agaacaaaga aagtgctcag aaattaaaag acagtcttac tgccaaaact 960
gtcaaaaccc tatttggcga tcccgtaaag gctgaacgtg cgaaaaattt gtttactaac 1020
actaactttg cagaacttct tcaacacaac aaactaaatg acttagtaaa caatcaacac 1080
tttacaaatc tgttcaaaaa tgaaacaaca gccaggcacg caaccgaaat cttaacttct 1140
cctcacttca aagcatcgct tgaaaacaat gaggcagtta ccaatttgaa aaaattactc 1200
actcattcag cactaagaga gctgttcagc aatgataatt tagaaaacgc aactagcttt 1260
gccaagaaac ttagagagct aggaatagta cgaacaaggt ga 1302

<210> SEQ ID NO 20
<211> LENGTH: 1614
<212> TYPE: DNA
<213> ORGANISM: Ehrlichia risticii

<400> SEQUENCE: 20
atggcaggtg atacactttt gagcgtactt tccgatgaaa cgcactttga aaatctaaca 60
gatggaatct tcctcagctt ggttaaggat ccgaattttg ctagtgcatc aaaaggcgtg 120
agtaaggcag agttgaaaga tgtactcact agcgaaaact ttaagggact atttgaagat 180
caagctaaag cacaaaatgt agtcgcagta ctgaaagact caatagcaaa gacagtactg 240
gaaagcgata aattcaaggc gctgcttcag acacaaggta aagctgagtt gcaagattta 300
ctaaccaatg acaattttaa gggactattt gaagatcaag ctaaagcaca aaatgtagtc 360
gcagtactga aagactcaat agcaaaggca gtactggaaa gcgataaatt caaggcgctg 420
cttcagacac aaggtaaagc tgagttgcaa gatttactaa ccaatgacaa ttttaaggga 480
ctatttgaag atcaagctaa agcacaaaat gtagtcgcag tactgaaaga ctcaatagca 540
aaggcagtac tggaaagcga taaattcaag gcgctgcttc agacacaagg taaagctgag 600
ttgcaagatt tactaaccaa tgacaatttt aagggactat ttgaagatca agctaaagca 660
caaaatgtag tcgcagtact gaaagactca atagcaaagg cagtactgga aagcgataaa 720
ttcaaggcgc tgcttcagac acaaggtaaa gctgagttgc aagatttact aaccaatgac 780

-continued

```
aattttaagg gactatttga agatcaagct aaagccagca gcataaaaac catactaacc    840

aaccaaaatg caacaggtgt tcttaccgat ggtacagcta gtaatgttat aacgaataac    900

actgccaaag aagtactaaa gaatgcaaat gcagctgaat tgcttaagga caacaacgca    960

gctgaagtac taaaagatga gacagcaaag gaaatattga aaaacatcaa gtttaaggaa   1020

attttaaaag gtgcgggcaa agacataata aaaaatatcc tcacagatgg cactggtact   1080

tttaaaggac ttctcgaatg tgcaggaaaa gataaagtag gcaatgttct cacaaatcag   1140

actttcaaaa agctgttcga aagtccaggt aatgaggaaa taaaagatat cctcattaac   1200

gaaaatttcg agtcatcatt cgagaacaaa gaaagtgctc agaaattaaa agacagtctt   1260

actgccaaaa ctgtcaaaac cctatttggc gatcccgtaa aggctgaacg tgcgaaaaat   1320

ttgtttacta acactaactt tgcagaactt cttcaacaca acaaactaaa tgacttagta   1380

aacaatcaac actttacaaa tctgttcaaa aatgaaacaa cagccaggca cgcaaccgaa   1440

atcttaactt ctcctcactt caaagcatcg cttgaaaaca atgaggcagt taccaatttg   1500

aaaaaattac tcactcattc agcactaaga gagctgttca gcaatgataa tttagaaaac   1560

gcaactagct ttgccaagaa acttagagag ctaggaatag tacgaacaag gtga         1614
```

<210> SEQ ID NO 21
<211> LENGTH: 1614
<212> TYPE: DNA
<213> ORGANISM: Ehrlichia risticii

<400> SEQUENCE: 21

```
atggcaggtg atacactttt gagcgtactt tccgatgaaa cgcactttga aaatctaaca     60

gatggaatct tcctcagctt ggttaaggat ccgaattttg ctagtgcatc aaaaggcgtg    120

agtaaggcag agttgaaaga tgtactcact agcgaaaact ttaagggact atttgaagat    180

caagctaaag cacaaaatgt agtcgcagta ctgaaagact caatagcaaa gacagtactg    240

gaaagcgata aattcaaggc gctgcttcag acacaaggta aagctgagtt gcaagattta    300

ctaaccaatg acaattttaa gggactattt gaagatcaag ctaaagcaca aaatgtagtc    360

gcagtactga aagactcaat agcaaaggca gtactggaaa gcgataaatt caaggcgctg    420

cttcagacac aaggtaaagc tgagttgcaa gatttactaa ccaatgacaa ttttaaggga    480

ctatttgaag atcaagctaa agcacaaaat gtagtcgcag tactgaaaga ctcaatagca    540

aaggcagtac tggaaagcga taaattcaag gcgctgcttc agacacaagg taaagctgag    600

ttgcaagatt tactaaccaa tgacaatttt aagggactat ttgaagatca agctaaagca    660

caaaatgtag tcgcagtact gaaagactca atagcaaagg cagtactgga aagcgataaa    720

ttcaaggcgc tgcttcagac acaaggtaaa gctgagttgc aagatttact aaccaatgac    780

aattttaagg gactatttga agatcaagct aaagccagca gcataaaaac catactaacc    840

aaccaaaatg caacaggtgt tcttaccgat ggtacagcta gtaatgttat aacgaataac    900

actgccaaag aagtactaaa gaatgcaaat gcagctgaat tgcttaagga caacaacgca    960

gctgaagtac taaaagatga gacagcaaag gaaatattga aaaacatcaa gtttaaggaa   1020

attttaaaag gtgcgggcaa agacataata aaaaatatcc tcacagatgg cactggtact   1080

tttaaaggac ttctcgaatg tgcaggaaaa gataaagtag gcaatgttct cacaaatcag   1140

actttcaaaa agctgttcga aagtccaggt aatgaggaaa taaaagatat cctcattaac   1200

gaaaatttcg agtcatcatt cgagaacaaa gaaagtgctc agaaattaaa agacagtctt   1260

actgccaaaa ctgtcaaaac cctatttggc gatcccgtaa aggctgaacg tgcgaaaaat   1320
```

ttgtttacta acactaactt tgcagaactt cttcaacaca acaaactaaa tgacttagta 1380
aacaatcaac actttacaaa tctgttcaaa aatgaaacaa cagccaggca cgcaaccgaa 1440
atcttaactt ctcctcactt caaagcatcg cttgaaaaca atgaggcagt taccaatttg 1500
aaaaaattac tcactcattc agcactaaga gagctgttca gcaatgataa tttagaaaac 1560
gcaactagct ttgccaagaa acttagagag ctaggaatag tacgaacaag gtga 1614

<210> SEQ ID NO 22
<211> LENGTH: 1302
<212> TYPE: DNA
<213> ORGANISM: Ehrlichia risticii

<400> SEQUENCE: 22
atggcaggtg atacactttt gagcgtactt tccgatgaaa cgcactttga aaatctaaca 60
gatggaatct tcctcagctt ggttaaggat ccgaattttg ctagtgcatc aaaaggcgtg 120
agtaaggcag agttgaaaga tgtactcact agcgaaaact ttaagggact atttgaagat 180
caagctaaag cacaaaatgt agtcgcagta ctgaaagact caatagcaaa gacagtactg 240
gaaagcgata aattcaaggc gctgcttcag acacaaggta aagctgagtt gcaagattta 300
ctaaccaatg acaattttaa gggactattt gaagatcaag ctaaagcaca aaatgtagtc 360
gcagtactga aagactcaat agcaaaggca gtactggaaa gcgataaatt caaggcgctg 420
cttcagacac aaggtaaagc tgagttgcaa gatttactaa ccaatgacaa ttttaaggga 480
ctatttgaag atcaagctaa agccagcagc ataaaaacca tactaaccaa ccaaaatgca 540
acaggtgttc ttaccgatgg tacagctagt aatgttataa cgaatgacac tgccaaagaa 600
gtactaaaga atgcaaatgc agctgaattg cttaaggaca acaacgcagc tgaagtacta 660
aaagatgaga cagcaaagga aatattgaaa aacatcaagt ttaaggaaat tttaaaaggt 720
gcgggcaaag acataataaa aaatatcctc acagatggca ctggtacttt taaaggactt 780
ctcgaatgtg caggaaaaga taaagtaggc aatgttctca caaatcagac tttcaaaaag 840
ctgttcgaaa gtccaggtaa tgaggaaata aaagatatcc tcattaacga aaatttcgag 900
tcatcattcg agaacaaaga aagtgctcag aaattaaaag acagtcttac tgccaaaact 960
gtcaaaaccc tatttggcga tcccgtaaag gctgaacgtg cgaaaaattt gtttactaac 1020
actaactttg cagaacttct tcaacacaac aaactaaatg acttagtaaa caatcaacac 1080
tttacaaatc tgttcaaaaa tgaaacaaca gccaggcacg caaccgaaat cttaacttct 1140
cctcacttca aagcatcgct tgaaaacaat gaggcagtta ccaatttgaa aaaattactc 1200
actcattcag cactaagaga gctgttcagc aatgataatt tagaaaacgc aactagcttt 1260
gccaagaaac ttagagagct aggaatagta cgaacaaggt ga 1302

<210> SEQ ID NO 23
<211> LENGTH: 1458
<212> TYPE: DNA
<213> ORGANISM: Ehrlichia risticii

<400> SEQUENCE: 23
atggcaggtg atacactttt gagcgtactt tccgatgaaa cgcactttga aaatctaaca 60
gatggaatct tcctcagctt ggttaaggat ccgaattttg ctagtgcatc aaaaggcgtg 120
agtaaggcag agttgaaaga tgtactcact agcgaaaact ttaagggact atttgaagat 180
caagctaaag cacaaaatgt agtcgcagta ctgaaagact caatagcaaa ggcagtactg 240

-continued

```
gaaagcgata aattcaaggc gctgcttcag acacaaggta aagctgagtt gcaagattta    300

ctaaccaatg acaattttaa gggactattt gaagatcaag ctaaagcaca aaatgtagtc    360

gcagtactga aagactcaat agcaaaggca gtactggaaa gcgataaatt caaggcactg    420

cttcagacac aaggtaaagc tgagttgcaa gatttactaa ccaatgacaa ttttaaggga    480

ctatttgaag atcaagctaa agcacaaaat gtagtcgcag tactgaaaga ctcaatagca    540

aaggcagtac tggaaagcga taaattcaag gcgctgcttc agacacaagg taaagctgag    600

ttgcaagatt tactaaccaa tgacaatttt aagggactat ttgaagatca agctaaagcc    660

agcagcataa aaaccatact aaccaaccaa aatgcaacag gtgttcttac cgatggtaca    720

gctagtaatg ttataacgaa taacactgcc aaagaagtac taaagaatgc aaatgcagct    780

gaattgctta aggacaacaa cgcagctgaa gtactaaaag atgagacagc aaaggaaata    840

ttgaaaaaca tcaagtttaa ggaaatttta aaaggtgcgg gcaaagacat aataaaaaat    900

atcctcacag atggcactgg tacttttaaa ggacttctcg aatgtgcagg aaaagataaa    960

gtaggcaatg ttctcacaaa tcagactttc aaaaagctgt tcgaaagtcc aggtaatgag   1020

gaaataaaag atatcctcat taacgaaaat ttcgagtcat cattcgagaa caaagaaagt   1080

gctcagaaat taaaagacag tcttactgcc aaaactgtca aaaccctatt tggcgatccc   1140

gtaaaggctg aacgtgcgaa aaatttgttt actaacacta actttgcaga acttcttcaa   1200

cacaacaaac taaatgactt agtaaacaat caacacttta caaatctgtt caaaaatgaa   1260

acaacagcca ggcacgcaac cgaaatctta acttctcctc acttcaaagc atcgcttgaa   1320

aacaatgagg cagttaccaa tttgaaaaaa ttactcactc attcagcact aagagagctg   1380

ttcagcaatg ataatttaga aaacgcaact agctttgcca agaaacttag agagctagga   1440

atagtacgaa caaggtga                                                 1458
```

<210> SEQ ID NO 24
<211> LENGTH: 1305
<212> TYPE: DNA
<213> ORGANISM: Ehrlichia risticii

<400> SEQUENCE: 24

```
atggtaggtg atacactttt aagcgtactt tccgatgaaa cacactttga aaatctaata     60

gatggaatct tcctcagctt ggttaaagat ccgaattttg ccagtgcatc aaaaggcgtg    120

agtaaggtag aattgaaaga tgtactcact agcgaaaact ttaagggact atttgaagat    180

caagctaaag cacaaaatgt agctgcagta ctgaaagact cagcagcaaa ggcagtactg    240

gaaagtgata aattcaaggc actgcttcag acacaaggta aagctgagtt gcaagatcta    300

ctaaccaatg aaaattttaa gggactgttt gaagatcaag ctaaagcaca aaatgtagct    360

gcagtactga aagactcagc agcaaaggca gtactggaaa gtgataaatt caaggcactg    420

cttcagacac aaggtaaagc tgagttgcaa gatctactaa ccaatgaaaa ttttaaggga    480

ctatttgaag atcaagctaa agccagcagc gcaaaaacca tactgactaa ccaaaatgca    540

ataggtgttc ttaccaatgg tacggccagt gctgttataa tgaatgatac cgctaaagaa    600

gttctaaaga acgcgaattc agctgagtta ctcaaggaca gcactgcggc tgaaatacta    660

aaagatgaga cgacaaagga agtactaaaa agcagcaagt ttaaagaaat tctaaaaggt    720

gcaggcaaag acacaataaa aaacatcctc acagatagca ccggcacttt caaagaactc    780

gttgaatgtg cgggaaaaga taaagtggaa aatgtgctca caaatcagac tttcaaaaag    840

ttgttcgaaa gtccaggtaa tgaagaaata aaagatatac ttactaacga aaattttgag    900
```

-continued

```
ttatcgttcg agaataaaaa aagcgccgaa aaattgaaag agactctcac taggccaatc    960

attaaagaac tatttagcga tccagtaaag gctgaacgtg tgggagatct gtttactaat   1020

gataacttta tagaacttct tcaacacggc aaattaaatg acttggtaaa caatcaacat   1080

tttaccaatc tgttcaaaaa cgaaacaaca gccggacacg caaccgaaat cttaacttct   1140

cctcacttca aagcatctct tgaaaataat gaagcagttg ctaatttgaa aaaattactc   1200

actaattcag cactaagaga gctatttagc aatgacaatc tggaagacgc aactagcttc   1260

gccaagaaac ttgtggagct aggaataata gcacgaataa aataa                   1305
```

<210> SEQ ID NO 25
<211> LENGTH: 1422
<212> TYPE: DNA
<213> ORGANISM: Ehrlichia risticii

<400> SEQUENCE: 25

```
atgccaggcg atacactttt gagcgtactt tccaatgaca catattttag tagcttaact     60

gatgaactcc tcctcagcct aattaaggac acagttttca atggaatgat aaaaggcgat    120

ggaaagatag aattaaaaga cattcttaca gataacaccg gcaaatttag agagcttgta    180

gaaagtagca gtaaagatat attaaaaagc atacttaccg acagcacagg taactttaaa    240

gggcttatag aaagcgcagg taaagagaaa gtaaaagcac ttctcacaga tgagaacttt    300

aaaaaattat ttgaggacga tacgaaagca aatcatgtaa aagaggtact tacagacaca    360

aatgctaagg aaatccttac ggatcaaaca ggcaaagaag tcctaaaaaa cagcacagct    420

aaagatatat taaaaagcac aaatgcagcc gaggtactaa aagacgccaa tgctaaggaa    480

atccttacgg atcaaacggg caaagaagtc ctaaaaaaca gcacagctaa agatatatta    540

aaaagcacaa atgcagccga ggtactaaaa gacgccaatg ctaaggaaat ccttacggat    600

caaacgggca aagaagtcct aaaaaacagc acagctaaag atatattaaa agacacaaat    660

gcagccgagg tactaaaaga cgacacagct aaggaagtat taaaaaacag taaatttaaa    720

gaagcaataa caggtgcagg taaagacata ctaaaagaca ttcttacaga cagcaccggt    780

aaatttaaag agcttataga aagcgcaggt aaagagaaag taaaagcgct tctcacagat    840

gagaacttta aaaaattatt tgaggacgat acgaaagcaa accatgtaaa agaggtactt    900

acagacataa atgctaagga aatccttacg gatcaaacag ctaaagaagt actaaaagac    960

agcacagcca aagaagtact aaaacacact aagtttaaag aagcaataac aggtgcaggt   1020

aaagacatac taaaagacat tcttacagac agcacaggta aattgaaagg gcttatagaa   1080

agtacaggta aaaacgaatt caaagatctc cttactaatg acagctttaa aagcttattt   1140

gacagcacaa atagcgccca agctgttaaa gcaatttttta ccaagagtga gcttaaaccc   1200

ctacttgaaa catgtaagca aaacgcaaac aaagtgcaag cactcgaagg agccttggaa   1260

agcctaaaag atttacttac agagagcgac agcagcaagt atgctgagaa attacaagcg   1320

tttggaaagg agctttgcac gaaaagaaag gagtgtgatg gtgctagcaa tttaagctgc   1380

agtaacctta cagtaagttg ctctagtacg tctagtagtt ga                      1422
```

<210> SEQ ID NO 26
<211> LENGTH: 1371
<212> TYPE: DNA
<213> ORGANISM: Ehrlichia risticii

<400> SEQUENCE: 26

```
atgttcaacc aagtaataaa aggtgaggga aaaacagaat taaaagacat acttacggat     60
agcactggta agtttaagga gcttatagaa ggcacaggta aggatatact aaaaagcata    120
ctcacagacg gctcaggcaa ctttaaagga cttgtggaaa gcaatggtag gacagaggca    180
aaagaggtac tcacccatgg gaaattcaag gaattattca gtacttctga cagagctggt    240
gttaccaaag aagtcttaac cgcagaacaa tttgaaaagc tacttgaagg cagcggtaag    300
actcaagcaa aagaggtgct cacaaacaag aactttaaaa aattatttga tactgccgac    360
agtgctaaaa ttgctaaaga agtgcttacg gcagaacaat ttgaaaagtt acttgaaggt    420
agcggtaaga ctcaagcaaa agaggtactc acaaacgaga actttaaaaa attatttgat    480
actgccgaca gcgctggtat tgttaaagaa gtgcttaccg cacaacaatt taaacaattg    540
ctcaaaggta gcggcaagac tcaagcaaaa gaggtgctca taaacgagaa ctttagtaag    600
ttatttgata ctgctgatag agctggtatt gctaaagaag ttctcactgc agaacaattt    660
gaaaagctac ttgaaggcag cggtaagact caagtaaaag aggttctcat aagcgagaac    720
tttaaaaatt tatttgaaaa cggcgctaaa gataaggtaa aagacctcct tgtcgacaag    780
aagtttaaag agctgtttgc cgatgcaaca aaagctgact atgtaaaaga aatactcaca    840
gacagcacag ctaaggagat acttacaaac caaacagcaa aagaggtact gaagaatgat    900
acagctaagg aagtactaaa atgcgataaa tttaaagaag caatagcagg tacaggtaaa    960
gacatactaa aagacattct tacagacagc acgggtaact ttaaaaggct tatagaaggc   1020
actggtaagg agaaagtaaa agaacttctt actgatgaga agtttaaaaa acttatggaa   1080
agtacagcca aggatgcggt aaaagaagtt cttacaaatg agaattttca aaaattattt   1140
aaccaagtta tcaaagctgg acatgttaag aacgcactaa taaacgaaaa cttctggaat   1200
ttatttgtaa agggtgaaaa agaatggagt aatgaatcat catttgtaaa aaccataagt   1260
gaactgaaag atctaatcca ctgcgaagat agtcagcatg aagaaaaact aaaagccttt   1320
ggagataagc tgaagaaggc aaaaaatccc aaccaaaaga aagaaaagta g             1371
```

<210> SEQ ID NO 27
<211> LENGTH: 1638
<212> TYPE: DNA
<213> ORGANISM: Ehrlichia risticii

<400> SEQUENCE: 27

```
atgtcaaatg aaacacttct gagcgtactt tctgatgaaa cgcactttgc taatctagtt     60
gatgaacttc ttctcagctt ggttaaagac agtattttca ctcaagtaat aaaaggcgag    120
ggaaagacag aattaaaaga cattcttaca gatagcactg gcaagtttaa agagctgata    180
ggaagtagcg gtaaggatat actaaaaagc atactcacag atggctcagg caactttaaa    240
ggccttatag aaagcacagg taaggcagaa gtaaaagagg tactcactaa tgaaaaattc    300
aaagagcttt ttggaagcga tggtaaggat atattaaaag acatactcac agatagcact    360
ggtaagttta aagagctgat aggaagtagc ggtaaggaca tactaaaaaa cattcttaca    420
gatagcaccg gtaagtttaa agaacttata gaaagtgcag gtaagggtaa gctgaaagac    480
cttcttattg atggaaactt taaaaaatta tttgaggatg acacgaaagc tgctcatgta    540
aaagaaatac ttacagacag caacgctaag gaaatactca caaatgaagt agcaaaagag    600
gtactaaaat ccgataaatt taaagatgca ataactggtg ctggtaagga cgcactaaaa    660
gagatactta cttgcgataa atttaaagat gcagtaacag gcaatggtaa ggacgcacta    720
aaagaaatac ttacttgcga taaatttaaa gaggcagtaa caggcgatgg taaagacaag    780
```

```
ctaaaagaga ttcttactca cgagaagttt aaagcactca tagagagtga aggcaaagac    840

atactgaaag aaattcttac agatagtacc ggtaaattta aagagctaat agaaagcact    900

ggtaaggata agctaaaaga gattcttaca gataacaccg gtaactttaa agggcttgta    960

gaaggcgccg gtaaggatga agcaaaagca gtacttactg acgagaaatt taaaggcttg   1020

tttgatgaca aaacaatagc tggctatgta aaagaaatac tcaccagcga gaagtttaaa   1080

aaactgtttg aaagtgcagg taagactaaa gtaaaagaac tcctcattga tgagaagttt   1140

caaaaattat ttgaggatga cacgaaagcc agtcatgtaa aagaaatact cacgaacgat   1200

acagctaagg aaatacttac caatgataaa tttaaggaag caataacagg cgatggtaaa   1260

gacatactaa aaggtatact tacagatagc actggtaact ttaaaggcgc aataacaggt   1320

gccggtaaag atgagctaaa agacatactc actaatagcg agtttaaaag cttatttgat   1380

agcaaagata gcgctgaagc tgttaaagca atttttaccg atactaaatt taagacctta   1440

cttcaaacat gcaagaagaa cccaaacaat acacaggcac ttgcagctgc tttagatgaa   1500

ctaaaagagc taattacctg tggcagcaat gatcatgcaa caaaactaca agcctttgga   1560

aatgcgctat gcaacagaaa gaaggaaacg tgcagtaatt ttagctctgc aaactgcact   1620

ggtacagcag ctacataa                                                 1638
```

<210> SEQ ID NO 28
<211> LENGTH: 1539
<212> TYPE: DNA
<213> ORGANISM: Ehrlichia risticii

<400> SEQUENCE: 28

```
atgacagacg atacactttt gagtgtgctt tccaatgaaa ctcattttaa taacttaatt     60

gatgaatttc ttctcagctt ggttaaggac gcaatgttca atcaagtaat aaaaggtgag    120

ggaaaaacag aattaaaaga catacttacg gacactacgg gcaaattcaa agagctgatc    180

ggaggtagtg gtaaagctat attaaaaagc atactcacag acaacaccgg taattttaaa    240

gcacttatcg aaggcaatgg taagacccaa gcaaaagagg tccttacaca tgagaaattt    300

aaggaattat tcagtactgc tgacagagct ggtattgcta aagaagtgct tactgctgaa    360

caatttgaaa aattactcaa aggtagcggt aagacccaag caaaagaggt gctaacaaac    420

gagaacttta ataaattatt tgataccacc agtagtgcaa agattgctaa agaagtgctt    480

actgcagaac aatttgaaaa gttacttaaa ggcagcggta aacccaagc aaaagaggtg    540

ctaacaaacg agaactttaa taaattattt gataccaccg gtagtgcaga tattgctaaa    600

gaagtgctca ctgcagaaca atttgaaaag ttacttaaag gcagcggtaa aacccaagca    660

aaagaggtgc taacaaacga gaactttaat aaattatttg atactaccgg tagtgcagat    720

attgctaaag aagtgctcac tgcagaacaa tttgaaaagt tacttgaagg cagcggtaag    780

aatgaaataa aagaggttct tacgaacgag aactttaaaa agttatttga taccgctgac    840

agcgctagta ttgctaaaga agtgctcact gcagaacaat ttgaaaagtt acttgaaggc    900

agcggtaaga ctcaagcaaa agaggtgctc acaaacgaga actttaaaaa actattcgaa    960

aacagcggca gagacatact aaaagacatt cttacagata gtactggtaa atttaaagag   1020

ctcatagaaa gtactggcaa ggagaaagta aaagaacttc ttatcgacgg gaaatttaag   1080

gacctgttca ccgatgcaac aaaagctggc tatgtaaaag aaatactcac gaacgataca   1140

gctaaagaca tactcactaa tgataaattt aaagatgcag taacaggtaa aggtaaagat   1200
```

-continued

```
gagctaaaaa gtatacttac caatgataat tttaaaaaac ttgtggaaag tacagccaaa   1260

gacaaggtaa aagaagttct tacaaatgag aattttcaaa aattgtttga ccaaaccaca   1320

aaagctgggc atgttaagag cgcactaacg gatgaaaact tctggaattt atttgtaaag   1380

agcaaaacag aatggagtag tgactcaccg tttgtaaaaa ccataagtga attgaaagac   1440

ctaatccact gcgaagatgg taagcatgaa gaaaaactaa aagcctttgg agataagctt   1500

aaggaggcaa aaaccccaga ttcaaagaaa aagaattag                          1539


<210> SEQ ID NO 29
<211> LENGTH: 1869
<212> TYPE: DNA
<213> ORGANISM: Ehrlichia risticii

<400> SEQUENCE: 29

atgtcaaatg aaacactttt gagcgtactt tcagatgaga cgcattttaa caacttagtt     60

gatgaactcc tcctcagctt ggttaaagac agtattttca ctcaagtgat aaaaggcgag    120

ggaaagacag aattaaaaga catacttaca gacaacactg gcaagtttaa agagctgata    180

ggaagtagcg gtaaggatat actaaaaagc atactcacag atggctcagg caactttaaa    240

ggactcatag aaagcacagg taagacacaa gtaaaagagg tcctcactaa tgaaaaattc    300

aaagagcttt ttggaagcga tggtaaggat atattaaaag acatactcac agataacacc    360

ggtaacttta aaggccttat agaaagcaca ggtaaggcgc aagtaaaaga ggtactcact    420

aatgaaaaat tcaaggagct ttttggaagc gaaggtaaag acatactaaa agagatactt    480

acagacaata ccggcaattt taaagggctt atagaaggca aaggtaagga tgaagcaaag    540

ggagtactta ctgacgagaa atttaaaggc ttgtttgatg acaaaacaat agctggctat    600

gtaaaagaaa tactcaccag cgagaagttt aaaaaactgt ttgaaaatgg tggaaaggaa    660

aaagtaaaag aacttcttat tgatgagaac tttaaaaaat tatttgagga tgacacgaaa    720

gctgctcatg taaaagaaat acttacagac agcaacgcta aggaaatact cacaaatgaa    780

gtagcaaaag aggtactaaa atccgataaa tttaaagatg caataactgg tgctggtaag    840

gacgcactaa aagagatact tacttgcgat aaatttaaag atgcagtaac aggcaatggt    900

aaggacgcac taaaagaaat acttacttgc gataaattta aagaggcagt aacaggcgat    960

ggtaaagaca agctaaaaga gattcttact cacgagaagt ttaaagcact catagagagt   1020

gaaggcaaag acatactgaa agacattctt acagatagta ccggtaaatt taaagagcta   1080

atagaaagca cgggtaagga taagctgaaa gaaatacttg tcgatgagaa atttaaggcc   1140

ctgtttactg atgcaacaaa agccggttat gtaaaagaaa tacttacaga cagcaacgct   1200

aaggaaatac tcacaaatga agtagcaaaa gaggtactaa aatccgataa atttaaagat   1260

gcaataactg gtgctggtaa ggacgcacta aaagagatac ttacctgtga taaatttaaa   1320

gatgcagtaa caggcaatgg taaggacgca ctaaaagaaa tacttacttg cgataaattt   1380

aaagatgcag taacaggcaa tggtaaagac aagctaaaag agattcttac tcacgagaag   1440

tttaaagcac tcatagagag tgaaggcaaa gacatactaa aaggtatact tacagatagc   1500

actggtaact ttaaaggcgc aataacaggt gccggtaaag atgagctaaa agacatactc   1560

actaatagcg agtttaaaag cttatttgag agcaaagata gcgctgaagc tgttaaagca   1620

atttttacca atgctaagtt taaaggacta cttgaaacat gcaagaacaa cccaaaaaat   1680

acacaggcgc tcgaaggagc tttagacagc ttaaaggagc tacttgaagt taacgacaac   1740

gttaactatg gtagcaaact aaaagacttt ggacagagtc tttgcacaaa aagaaaggaa   1800
```

```
ttagatgatg gttttaccaa cccaaattgc aatagtattg tagttactgt tcctaattcg   1860

actcattaa                                                           1869
```

<210> SEQ ID NO 30
<211> LENGTH: 1410
<212> TYPE: DNA
<213> ORGANISM: Ehrlichia risticii

<400> SEQUENCE: 30

```
atgacagacg atacactttt gagtgtgctt tccaatgaaa ctcattttaa taacttaatt     60

gatgaatttc ttctcagctt ggttaaggac gcaatgttca atcaagtaat aaaaggtgag    120

ggaaaaacag aattaaaaga catacttacg gacactacgg gcaaattcaa agagctgatc    180

ggaggtagtg gtaaagctat attaaaaagc atactcacag acaacaccgg taattttaaa    240

gcacttatcg aaggcaatgg taagacccaa gcaaaagagg tccttacaca tgagaaattt    300

aaggaattat tcagtactgc tgacagagct ggtattgcta aagaagtgct tactgctgaa    360

caatttgaaa aattactcaa aggtagcggt aagacccaag caaaagaggt gctaacaaac    420

gagaacttta ataaattatt tgataccacc agtagtgcaa agattgctaa agaagtgctt    480

actgccgaac aatttgaaaa gttacttaaa ggtagcggta agacccaagc aaaagaggtg    540

ctaacaaacg agaactttaa taaattattt gatactaccg gtagtgcaga tattgctaaa    600

gaagtgctca ctgcagaaca atttgaaaag ttacttaaag gcagcggtaa aacccaagca    660

aaagaggtgc taacaaacga gaactttaat aaattatttg atactaccgg tagtgcagat    720

attgctaaag aagtgctcac tgcagaacaa tttgaaaagt tacttgaagg cagcggtaag    780

actcaagcaa aagaggtgct cacaaacgag aactttaaaa aactattcga aaacagcggc    840

agagacatac taaaagacat tcttacagat agtactggta aatttaaaga gctcatagaa    900

agtactggca aggagaaagt aaaagaactt cttatcgacg ggaaatttaa ggacctgttc    960

accgatgcaa caaaagctgg ctatgtaaaa gaaatactca cgaacgatac agctaaagac   1020

atactcacta atgataaatt taaagatgca gtaacaggta aaggtaaaga tgagctaaaa   1080

agtatactta ccaatgataa ttttaaaaaa cttgtggaaa gtacagccaa agacaaggtg   1140

aaagaagttc ttacaaatga gaattttcaa aaattgtttg accaaaccac aaaagctggg   1200

catgttaaga gcgcactaac ggatgaaaac ttctggaatt tatttacaaa gagtgacaca   1260

gaattcagta attactcacc atttgtaaaa accataagtg aattgaaaga cctaattcac   1320

tgcgaagatg gtaagcatga agaaaaacta aaagcctttg gagataagct taaggaggca   1380

aaaaccccag attcaaagaa aaagaattag                                    1410
```

<210> SEQ ID NO 31
<211> LENGTH: 1506
<212> TYPE: DNA
<213> ORGANISM: Ehrlichia risticii

<400> SEQUENCE: 31

```
atgtcaaatg aaacacttct gagcgtactt tctgatgaaa cgcactttgc taatctagtt     60

gatgaacttc ttctcagctt ggttaaagac agtattttca ctcaagtaat aaaaggcgag    120

ggaaagacag aattaaaaga cattcttaca gatagcactg gcaagtttaa agagctgata    180

ggaagtagcg gtaaggatat actaaaaagc atactcacag atggctcagg caactttaaa    240

ggccttatag aaagcacagg taaggcagaa gtaaaagagg tactcactaa tgaaaaattc    300
```

-continued

```
aaagagcttt ttggaagcga tggtaaggat atattaaaag acatactcac agatagcact    360

ggtaagttta aagagctgat aggaagtagc ggtaaggaca tactaaaaaa cattcttaca    420

gatagcaccg gtaagtttaa agaacttata gaaagtgcag gtaagggtaa gctgaaagac    480

cttcttattg atggaaactt taaaaaatta tttgaggatg acacgaaagc tgctcatgta    540

aaagaaatac ttacagacag caacgctaag gaaatactca caaatgaagt agcaaaagag    600

gtactaaaat ccgataaatt taaagatgca ataactggtg ctggtaagga cgcactaaaa    660

gaaatactta cttgcgataa atttaaagag gcagtaacag gcgatggtaa ggacgcacta    720

aaagaaatac ttacttgcga taaatttaaa gatgcagtaa caggcaatgg taaagacaag    780

ctaaaagaga ttcttactca cgagaagttt aaagcactca tagagagtga aggcaaagac    840

atactgaaag acattcttac agatagtacc ggtaaattta aagagctaat agaaagcacg    900

ggtaaggatg aagcaaaagc agtacttact gacgagaaat ttaaagactt gtttaatgac    960

aaaacaacag ctggctacgt gaaagaaata ctcaccagtg ataagtttaa aaaattattt   1020

gaggacaata ccaaagctgg ctacgtgaaa gaaatactca cgaacgatac agctaaggaa   1080

atacttacca atgataaatt taaggaagca ataacaggcg atggtaaaga catactgaaa   1140

gaaattctta cagatagcac tggtaacttt aaaggcgcaa taacaggtgc cggtaaagat   1200

gagctaaaat acatactcac taatagcgag tttaaaagct tatttgatag caaagatagc   1260

gctgaagctg ttaaagaaat atttacccac agtaagttta aagaactact taaaacgtgc   1320

aaggacaacc caaaaaatac ggcggcgctt gcagctgctt tagatgaact aaaagatcta   1380

attacctgtg gcagcggtga tcatgcaaca aaactacaag cctttggaag tgcactatgc   1440

accagaaaaa aagagtcgtg cgataatttt agctctgcaa actgcagtag tacaacaact   1500

gcataa                                                              1506
```

<210> SEQ ID NO 32
<211> LENGTH: 1539
<212> TYPE: DNA
<213> ORGANISM: Ehrlichia risticii

<400> SEQUENCE: 32

```
atgacagacg atacactttt gagtgtgctt tccaatgaaa ctcattttaa taacttaatt     60

gatgaatttc ttctcagctt ggttaaggac gcaatgttca atcaagtaat aaaaggtgag    120

ggaaaaacag aattaaaaga catacttacg gacactacgg gcaaattcaa agagctgatc    180

ggaggtagtg gtaaagctat attaaaaagc atactcacag acaacaccgg taattttaaa    240

gcacttatcg aaggcaatgg taagacccaa gcaaaagagg tccttacaca tgagaaattt    300

aaggaattat tcagtactgc tgacagagct ggtattgcta aagaagtgct tactgctgaa    360

caatttgaaa aattactcaa aggtagcggt aagacccaag caaaagaggt gctaacaaac    420

gagaacttta ataaattatt tgataccacc agtagtgcaa agattgctaa agaagtgctt    480

actgccgaac aatttgaaaa gttacttaaa ggcagcggta aacccaagc aaaagaggtg     540

ctaacaaaca agaactttaa taaattattt gataccaccg gtagtgcaga tattgctaaa    600

gaagtgctca ctgcagaaca atttgaaaag ttacttaaag gcagcggtaa aacccaagca    660

aaagaggtgc taacaaacga gaactttaat aaattatttg atactaccgg tagtgcagat    720

attgctaaag aagtgctcac tgcagaacaa tttgaaaagt tacttgaagg cagcggtaag    780

aatgaaataa aagaggttct tacgaacgag aactttaaaa agttatttga taccgctgac    840

agcgctagta ttgctaaaga agtgctcact gcagaacaat ttgaaaagtt acttgaaggc    900
```

```
agcggtaaga ctcaagcaaa agaggtgctc acaaacgaga actttaaaaa actattcgaa    960
aacagcggca gagacatact aaaagacatt cttacagata gtactggtaa atttaaagag   1020
ctcatagaaa gtactggcaa ggagaaagta aaagaacttc ttatcgacgg gaaatttaag   1080
gacctgttca ccgatgcaac aaaagctggc tatgtaaaag aaatactcac gaacgataca   1140
gctaaagaca tactcactaa tgataaattt aaagatgcag taacaggtaa aggtaaagat   1200
gagctaaaaa gtatacttac caatgataat tttaaaaaac ttgtggaaag tacagccaaa   1260
gacaaggtaa aagaagttct tacaaatgag aattttcaaa aattgtttga ccaaaccaca   1320
aaagctgggc atgttaagag cgcactaacg gatgaaaact tctggaattt atttacaaag   1380
agtgacacag aattcagtaa ttactcacca tttgtaaaaa ccataagtga attgaaagac   1440
ctaattcact gcgaagatgg taagcatgaa gaaaaactaa aagcctttgg agataagctt   1500
aaggaggcaa aaaccccaga ttcaaagaaa aagaattag                          1539
```

<210> SEQ ID NO 33
<211> LENGTH: 1620
<212> TYPE: DNA
<213> ORGANISM: Ehrlichia risticii

<400> SEQUENCE: 33

```
atgtcaaatg aaacacttct gagcgtactt tctgatgaaa cgcactttgc taatctagtt     60
gatgaacttc ttctcagctt ggttaaagac agtattttca ctcaagtaat aaaaggcgag    120
ggaaagacag aattaaaaga cattcttaca gatagcactg gcaagtttaa agagctgata    180
ggaagtagcg gtaaggatat actaaaaagc atactcacag atggctcagg caactttaaa    240
ggccttatag aaagcacagg taaggcagaa gtaaaagagg tactcactaa tgaaaaattc    300
aaagagcttt ttggaagcga aggtaaagac atactaaaag agatacttac agacaatacc    360
ggcaatttta aagggcttat agaaggcaaa ggtaaggatg aagcaaaggg agtacttact    420
gacgagaaat ttaaaggctt gtttgatgac aaaacaatag ctggctatgt aaaagaaata    480
ctcaccagcg agaagtttaa aaaactgttt gaaagtgcag gtaagactaa agtaaaagaa    540
ctcctcattg atgagaagtt tcaaaaatta tttgaggatg acacgaaagc cagtcatgta    600
aaagaaatac ttacagacag caacgctaag gaaatactca caaatgaagt agcaaaagag    660
gtactaaaat ccgataaatt taaagatgca ataactggtg ctggtaagga cgcactaaaa    720
gagatactta cttgcgataa atttaaagat gcagtaacag gcaatggtaa ggacgcacta    780
aaagaaatac ttacttgcga taaatttaaa gatgcagtaa caggcaatgg taaagacaag    840
ctaaaagaga ttcttactca cgagaagttt aaagcactca tagagagtga aggcaaagac    900
atactgaaag aaattcttac agatagtacc ggtaaattta aagagctaat agaaagcact    960
ggtaaagaca agctaaaaga gattcttaca gataacaccg gtaactttaa agggcttgta   1020
gaaggcgccg gtaaggatga agcaaaagca gtacttactc acgagaaatt taaagacttg   1080
tttaatgaca aaacaacagc tggctacgtg aaagaaatac tcaccagtga taagtttaaa   1140
aaattatttg aggacaatac caaagctggc tacgtgaaag aaatactcac gaacgataca   1200
gctaaggaaa tactcacaaa tcaaacagct aaagaagtcc taaaagacag cacagccaaa   1260
gaaatactaa aatgcgataa atttaaggac gcaataacag gcgctggtaa agatgagcta   1320
aaatacatac tcactaataa cgagtttaaa agcttatttg atagcaaaga tagcgctgaa   1380
gctgttaaag caatatttac ccacaataag tttaaagaac tacttaaaac gtgcaaggac   1440
```

aacccaaaaa atacggcggc gcttgcagct gctttagatg aactaaaaga tctaattacg 1500
tgtgacggca ataatcatgc aacaaaacta caagcctttg gaagtgcact atgcaccaga 1560
aaaaaagagt cgtgcgataa ttttagccct gcaagctgca gtagtacagc agctacataa 1620

<210> SEQ ID NO 34
<211> LENGTH: 1539
<212> TYPE: DNA
<213> ORGANISM: Ehrlichia risticii

<400> SEQUENCE: 34
atgacagacg atacactttt gagtgtgctt tccaatgaaa ctcattttaa taacttaatt 60
gatgaatttc ttctcagctt ggttaaggac gcaatgttca atcaagtaat aaaaggtgag 120
ggaaaaacag aattaaaaga catacttacg gacactacgg gcaaattcaa agagctgatc 180
ggaggtagtg gtaaagctat attaaaaagc atactcacag acaacaccgg taattttaaa 240
gcacttatcg aaggcaatgg taagacccaa gcaaaagagg tccttacaca tgagaaattt 300
aaggaattat tcagtactgc tgacagagct ggtattgcta aagaagtgct tactgctgaa 360
caatttgaaa aattactcaa aggtagcggt aagacccaag caaaagaggt gctaacaaac 420
gagaacttta ataaattatt tgataccacc agtagtgcaa agattgctaa agaagtgctt 480
actgccgaac aatttgaaaa gttacttaaa ggcagcggta aaacccaagc aaaagaggtg 540
ctaacaaacg agaactttaa taaattattt gataccaccg gtagtgcaga tattgctaaa 600
gaagtgctca ctgcagaaca atttgaaaag ttacttaaag gcagcggtaa aacccaagca 660
aaagaggtgc taacaaacga gaactttaat aaattatttg atactaccgg tagtgcagat 720
attgctaaag aagtgctcac tgcagaacaa tttgaaaagt tacttgaagg cagcggtaag 780
aatgaaataa aagaggttct tacgaacgag aactttaaaa agttatttga taccgctgac 840
agcgctagta ttgctaaaga agtgctcact gcagaacaat ttgaaaagtt acttgaaggc 900
agcggtaaga ctcaagcaaa agaggtgctc acaaacgaga actttaaaaa actattcgaa 960
aacagcggca gagacatact aaaagacatt cttacagata gtactggtaa atttaaagag 1020
ctcatagaaa gtactggcaa ggagaaagta aaagaacttc ttatcgacgg gaaatttaag 1080
gacctgttca ccgatgcaac aaaagctggc tatgtaaaag aaatactcac gaacgataca 1140
gctaaagaca tactcactaa tgataaattt aaagatgcag taacaggtaa aggtaaagat 1200
gagctaaaaa gtatacttac caatgataat tttaaaaaac ttgtggaaag tacagccaaa 1260
gacaaggtaa aagaagttct tacaaatgag aattttcaaa aattgtttga ccaaaccaca 1320
aaagctggac atgttaagag cgcactaaca gatgaaaact tctggaattt atttacaaag 1380
agtgacacag aattcagtaa ttactcacca tttgtaaaaa ccataagtga actgaaagac 1440
ctaatccact gcgaagatgg taagcatgaa gaaaaactaa aagcctttgg agataagctt 1500
aaggaggcaa aaaccccaga ttcaaagaaa aagaattag 1539

<210> SEQ ID NO 35
<211> LENGTH: 1887
<212> TYPE: DNA
<213> ORGANISM: Ehrlichia risticii

<400> SEQUENCE: 35
atgtcaaatg aaacactttt gagcgtactt tctgatgaaa cgcactttgc taatctagtt 60
gatgaacttc ttctcagctt ggttaaagac agtattttca ctcaagtaat aaaaggcgag 120
ggaaagacag aattaaaaga catacttaca gacaacactg gtaagtttaa agaacttata 180

```
gaaagtgcag gtaaagacat actaaaagag atacttacag acaataccgg caattttaaa    240

ggacttatag aaggtaatgg taagacggag gcaaaagagg tactcactaa tgaaaaattc    300

aaggagcttt ttggaagcaa tggtaaggac atactgaaag acattcttac agataacacc    360

ggtaacttta aaggccttat agaaagtgca gctaagggta agctgaaaga tcttcttatt    420

gatgaaaaat ttcaaaaatt attcgaggat gaaacgaaag ctggtcgtgt aaaagaaata    480

cttacagaca gcaacgctaa ggaaatactc acaaatgaag tagcaaaaga ggtactaaaa    540

tccgataaat tcaaggaggc aataactggc gatggtaagg acgcactaaa agagatactt    600

acttgtgata aatttaaaga ggcagtaaca ggcaatggta aagacatact aaaaggtata    660

cttacagata gcactggtaa atttaaagaa cttatagaaa gtactagtaa agacatacta    720

aaagagatac ttacagataa taccggtaac tttaaaggcc ttatagaaag cactggcaag    780

gagaaagtaa aagaacttct tatcgatggg aagtttaagg acctgtttac tgatgcaaca    840

aaagccggtt atgtaaaaga aatactcacg aacgatacag ctaaggaagt acttacagat    900

caaacagcaa aggaggtcct aaaagatagt acagctaaag acatattaaa ggacacaaac    960

gcagctgcgg tactaaaaaa cagcacagct aaagaaatac ttacaaacca aaccgctaaa   1020

gaagtgctta cagatggtac agccaaagaa gtactaaaag agatacttac ttgtgataaa   1080

tttaaagagg cagtaacagg caatggtaaa gacatactaa aaggtatact tacagatagc   1140

actggtaaat ttaaagagct aatagaaagc actggtaagg ataagctaaa agagattctt   1200

acagataaca ccggtaactt taaagggctt gtagaaggcg ccggtaagga tgaagcaaaa   1260

gcagtactta ctcacgagaa atttaaagac ttgtttaatg acaaaaacaac agctggctac   1320

gtgaaagaaa tacttaccag cgacaagttt aaagaactgt ttactgatgc aacaaaagct   1380

ggctacgtga aagaaatact cacgaacgat acagctaagg aaatacttac agatcaaaca   1440

gctaaagaag tcctaaagga tggtacagct aaagacatat taaaggacac aaacgcagct   1500

gcgctactaa aagacagcac agccaaagaa gtactaaaat gcgataaatt taaggaagca   1560

ataacaggtg ccggtaaaga tgagctaaaa tacatactca ctaatagcga gtttaaaagc   1620

ttatttgata gcaaagatag cgctgaagct gttaaagcaa tatttaccca caataagttt   1680

aaagaactac ttgaaacatg caagaacaac ccaaacaata cgcaggcgct tgcaaatgct   1740

ttagatgaac taaaagcgct aattacctgt ggcagcggtg atcatgcaac aaaactacaa   1800

gcctttggaa gtgcactatg caccaaaaag aaggagttgt gcagtaattt tagctctgca   1860

aactgcagta gtacaacaac tgcataa                                       1887
```

<210> SEQ ID NO 36
<211> LENGTH: 1539
<212> TYPE: DNA
<213> ORGANISM: Ehrlichia risticii

<400> SEQUENCE: 36

```
atgacagacg atacactttt gagtgtgctt tccaatgaaa ctcattttaa taacttaatt     60

gatgaatttc ttctcagctt ggttaaggac gcaatgttca atcaagtaat aaaaggtgag    120

ggaaaaacag aattaaaaga catacttacg gacactacgg gcaaattcaa agagctgatc    180

ggaggtagtg gtaaagctat attaaaaagc atactcacag acaacaccgg taattttaaa    240

gcacttatcg aaggcaatgg taagacccaa gcaaaagagg tccttacaca tgagaaattt    300

aaggaattat tcagtactgc tgacagagct ggtattgcta aagaagtgct tactgctgaa    360
```

-continued

```
caatttgaaa aattactcaa aggtagcggt aagacccaag caaaagaggt gctaacaaac    420
gagaacttta ataaattatt tgataccacc agtagtgcaa agattgctaa agaagtgctt    480
actgccgaac aatttgaaaa gttacttaaa ggcagcggta aaacccaagc aaaagaggtg    540
ctaacaaaca agaactttaa taaattattt gataccaccg gtagtgcaga tattgctaaa    600
gaagtgctca ctgcagaaca atttgaaaag ttacttaaag gcagcggtaa aacccaagca    660
aaagaggtgc taacaaacga gaactttaat aaattatttg atactaccgg tagtgcagat    720
attgctaaag aagtgctcac tgcagaacaa tttgaaaagt tacttgaagg cagcggtaag    780
aatgaaataa aagaggttct tacgaacgag aactttaaaa agttatttga taccgctgac    840
agcgctagta ttgctaaaga agtgctcact gcagaacaat ttgaaaagtt acttgaaggc    900
agcggtaaga ctcaagcaaa agaggtgctc acaaacgaga actttaaaaa actattcgaa    960
aacagcggca gagacatact aaaagacatt cttacagata gtactggtaa atttaaagag   1020
ctcatagaaa gtactggcaa ggagaaagta aaagaacttc ttatcgacgg gaaatttaag   1080
gacctgttca ccgatgcaac aaaagctggc tatgtaaaag aaatactcac gaacgataca   1140
gctaaagaca tactcactaa tgataaattt aaagatgcag taacaggtaa aggtaaagat   1200
gagctaaaaa gtatacttac caatgataat tttaaaaaac ttgtggaaag tacagccaaa   1260
gacaaggtaa aagaagttct tacaaatgag aattttcaaa aattgtttga ccaaaccaca   1320
aaagctgggc atgttaagag cgcactaacg gatgaaaact tctggaattt atttgtaaag   1380
agcaaaacag aatggagtag tgactcaccg tttgtaaaaa ccataagtga attgaaagac   1440
ctaatccact gcgaagatgg taagcatgaa gaaaaactaa aagcctttgg agataagctt   1500
aaggaggcaa aaaccccaga ttcaaagaaa aagaattag                          1539
```

POTOMAC HORSE FEVER ISOLATES

RELATED APPLICATIONS

This application depends for priority on U.S. Provisional Application No. 61/378,261 filed Aug. 30, 2010 and U.S. Provisional Application No. 61/381,326 filed Sep. 9, 2010, both of which are hereby incorporated by reference in their entireties.

FIELD OF INVENTION

The present invention relates to novel isolates of *Neorickettsia risticii* and compositions comprising such isolates, and methods of using such compositions in vaccines against Potomac Horse Fever.

BACKGROUND

Potomac Horse Fever (PHF), an acute infectious disease of horses, was reportedly first recognized in 1979 in the region of the Potomac River in Maryland and Virginia. The disease is also identified as Equine Monocytic Ehrlichiosis and Equine Intestinal Ehrlichiosis. The causative agent is a gram-negative, obligate intracellular bacterium which was first identified in 1984 as *Ehrlichia risticii* (*E. risticii*), but has been renamed *Neorickettsia risticii* (*N. risticii*). The disease is characterized by a wide variety of intestinal symptoms, along with elevated temperature and inflamed mucus membranes. In many cases it results in severe pain, and sometimes death.

The bacteria infect the enterocytes of the small and large intestine, resulting in acute colitis syndrome, and producing symptoms of mild colic, fever, depression, anorexia and diarrhea in horses of all ages. The disease can also cause abortion in pregnant mares, laminitis, and death. *N. risticii* has been isolated from trematodes infecting fresh water snails, and from caddisflies, mayflies, damselflies, dragonflies and stoneflies. The route of infection appears to be inadvertent ingestion of the aquatic insects carrying *N. risticii*, and the incubation period is 10 to 18 days.

An antigen for use in an assay to detect the presence of *N. risticii* has been claimed in U.S. Pat. No. 4,759,927, which is herein incorporated by reference in its entirety. Its source was later identified as the 25-D strain. A second strain identified as 90-12, was disclosed in U.S. Pat. No. 6,375,954, which is herein incorporated by reference in its entirety. U.S. Pat. No. 6,375,954 claims a method for protecting against *N. risticii* by administering a particular 90-12 protein antigen. Equine vaccines are commercially available, but provide only partial or no protection against newer strains of *N. risticii*, and against strains we have isolated relating to the present invention.

The citation of any reference herein should not be construed as an admission that such reference is available as "prior art" to the instant application.

SUMMARY OF THE INVENTION

The present invention provides three novel strains of *N. risticii* that infect horses, and possibly other mammals. We have identified these three novel *N. risticii* isolates as *N. risticii* Oregon (OR), *N. risticii* New York (NY) and *N. risticii* Michigan (MI), and deposited them with the ATCC, Manassas, Va., USA, as *N. risticii* Oregon (ATCC No. PTA-11232), *N. risticii* New York (ATCC No. PTA-11231) and *N. risticii* Michigan (ATCC No. PTA-11404). We have characterized these strains and have shown them to be biologically and structurally distinguishable from previously known strains.

The invention also provides novel protein antigens that characterize the new strains, as well as nucleic acids encoding these protein antigens, expression vectors that comprise such nucleic acids and express the protein antigens, vaccines comprising the new strains and/or the protein antigens, and/or the expression vectors, compounds comprising their protective antigens, methods for protecting animals, methods for producing the new strains and assays for detecting the novel strains. There is therefore a need for new vaccines against Potomac Horse fever.

These and other aspects of the present invention will be better appreciated by reference to the following figures and Detailed Description.

BRIEF DESCRIPTION OF THE FIGURES

FIGS. 4A-1, 4A-2, 4A-3, 4B-1, 4B-2, 4B-3, 4C-1, 4C-2, 4C-3, and 4D depict a strain specific antigen (SSA) amino acid sequence alignment for the SSA 1 proteins of six *N. risticii* isolates. From the top to bottom:
  *N. risticci* ILL stain-CP001431, SEQ ID NO: 1
  *N. risticci* Oregon, SEQ ID NO: 2
  *N. risticci* 25-D, SEQ ID NO: 3
  *N. risticci,* 90-12 SEQ ID NO: 4
  *N. risticci* Michigan, SEQ ID NO: 5
  *N. risticci* New York, SEQ ID NO: 6

FIGS. 5A-1, 5A-2, 5A-3, 5B-1, 5B-2, 5B-3, and 5C depict a SSA amino acid sequence alignment for the SSA 2 protein of six *N. risticii* isolates. From the top to bottom:
  *N. risticci* ILL stain-CP001431, SEQ ID NO: 7
  *N. risticci* New York, SEQ ID NO: 8
  *N. risticci* 90-12, SEQ ID NO: 9
  *N. risticci,* 25-D, SEQ ID NO: 10
  *N. risticci* Oregon, SEQ ID NO: 11
  *N. risticci,* Michigan, SEQ ID NO: 12

FIGS. 6A-1, 6A-2, 6A-3, 6B-1, 6B-2, 6B-3, and 6C depict a SSA amino acid sequence alignment for SSA 3 protein of six *N. risticii* isolates. From the top to bottom:
  *N. risticci* ILL stain-CP001431, SEQ ID NO: 13
  *N. risticci* New York, SEQ ID NO: 14
  *N. risticci* 90-12, SEQ ID NO: 15
  *N. risticci,* 25-D, SEQ ID NO: 16
  *N. risticci,* Michigan, SEQ ID NO: 17
  *N. risticci,* Oregon, SEQ ID NO: 18

FIGS. 7A-1, 7A-2, 7 A-3, 7B-1, 7B-2, 7 B-3, 7C-1, 7C-2, 7C-3, 7D-1, 7D-2, 7D-3, 7E-1, 7E-2, 7E-3, 7F-1, 7F-2, 7F-3, 7G-1, 7G-2, and 7G-3 depict a SSA nucleic acid sequence alignment for the genes encoding SSA 3 of six *N. risticii* isolates. From the top to bottom:
  *N. risticci* ILL stain-CP001431, SEQ ID NO: 19
  *N. risticci* New York, SEQ ID NO: 20
  *N. risticci* 90-12, SEQ ID NO: 21
  *N. risticci,* 25-D, SEQ ID NO: 22
  *N. risticci,* Michigan, SEQ ID NO: 23
  *N. risticci,* Oregon, SEQ ID NO: 24

FIG. 8 depicts the nucleic acid sequence (SEQ ID NO: 25) for the coding sequence of the SSA#1 protein of *N. risticii* Oregon.

FIG. 9 depicts the nucleic acid sequence (SEQ ID NO: 26) for the coding sequence of the SSA#2 protein of *N. risticii* Oregon.

FIG. 10 depicts the nucleic acid sequence (SEQ ID NO: 27) for the coding sequence of the SSA#1 protein of *N. risticii* New York.

FIG. 11 depicts the nucleic acid sequence (SEQ ID NO: 28) for the coding sequence of the SSA#2 protein of *N. risitcii* New York.

FIG. 12 depicts the nucleic acid sequence (SEQ ID NO: 29) for the coding sequence of the SSA#1 protein of *N. risticii* Michigan.

FIG. 13 depicts the nucleic acid sequence (SEQ ID NO: 30) for the coding sequence of the SSA#2 protein of *N. risticii* Michigan.

FIG. 14 depicts the nucleic acid sequence (SEQ ID NO: 31) for the coding sequence of the SSA#1 protein of *N. risticii* Illinois (CP001431).

FIG. 15 depicts the nucleic acid sequence (SEQ ID NO: 32) for the coding sequence of the SSA#2 protein of *N. risticii* Illinois (CP001431).

DETAILED DESCRIPTION OF THE INVENTION

Figure 1:
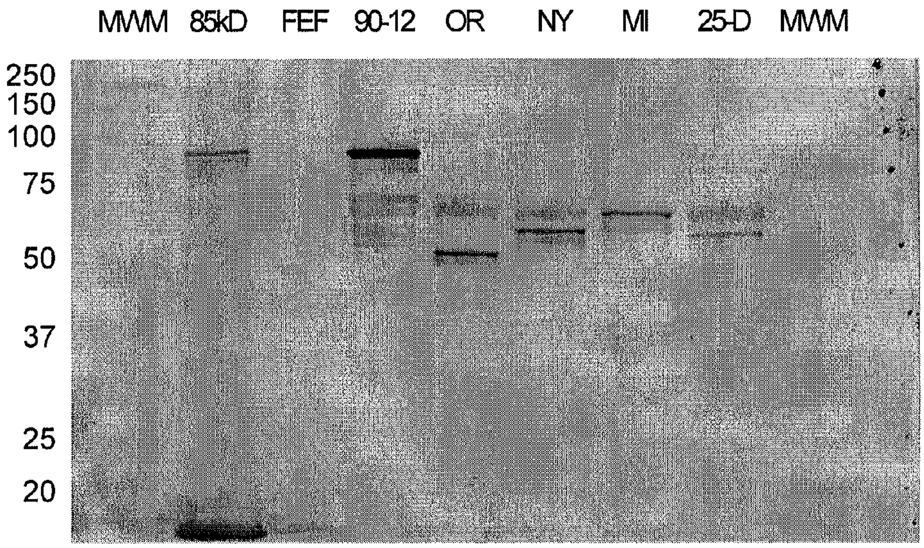
FIG. 1 depicts a Western Blot showing antibody reactivity and antigen banding with rabbit serum against the recombinant 85 kD strain specific antigen (SSA) of the *N. ristcii* 90-12 strain, FEF cells used to propagate *N. risticii*, and the 90-12, OR, NY, MI and 25-D strains.

Commercially available vaccines presently comprise antigens from the Illinois strain of *N. risticii*. Commercially available vaccines include POTOMAVAC™ from Merial, Athens, Ga. and POTOMACGUARD™ from Pfizer Inc, Fort Dodge, Iowa. The available vaccines do not presently provide full protection against all current Potomac Horse Fever (PHF) outbreaks. Therefore, we have sought to identify currently circulating strains that are immunogenically distinguishable from the known vaccine strains. For this purpose, we have solicited serum samples from animals showing clinical signs of PHF, from which we have isolated and characterized the three new *N. risticii* strains of the invention. These three new strains, *N. risticii* Oregon, *N. risticii* New York and *N. risticii* Michigan, can be distinguished both by their strain specific antigens (SSA's), i.e., expressed surface antigens that characterize the different strains of *N. risticii*, and by the failure of available vaccines to fully protect animals against infection upon challenge with these novel strains.

The novel Oregon strain was isolated from a blood sample from a horse in Oregon that had been immunized with a commercially available vaccine, but still exhibited clinical signs of PHF. We found that horses immunized with the *N. risticii* 90-12 strain were not protected when challenged with the newly isolated *N. risticii* Oregon strain. In addition, *N. risticii* Oregon did not to react with monoclonal antibodies raised against the 90-12 strain.

The novel New York (NY) strain was isolated from the blood sample of a horse from New York State exhibiting signs of PHF. We found that horses immunized with the *N. risticii* 90-12 strain showed a significant reduction in clinical disease and bacteremia upon heterologous challenge with the *N. risticii* New York strain. *N. risticii* New York does react with a monoclonal antibody to the 90-12.

The novel Michigan (MI) strain was isolated from the blood sample of a horse from Michigan exhibiting signs of PHF. The MI strain is shown to be unique by its antigen banding pattern (FIGS. 1 and 2) and by its SSA #1 protein sequence when compared with the other isolates.

*N. risticii* bacteria are typically characterized by their strain specific antigens, and the Oregon strain has a SSA #3 of approximately 50 kDa, the New York strain has a SSA #3 of approximately 55 kDa, and the Michigan strain has a SSA#3 of approximately 60 kDa, whereas the 90-12 strain has a SSA #3 of approximately 85 kDa.

In addition to the novel strains of *N. risticii* and their antigens, the present invention also relates to immunogenic compositions and vaccines. The therapeutic agent (also referred to as the antigen, active agent, or the immunogenic composition) that can serve as the basis for a vaccine can be one or more of the following:

a) harvested cultures of host cells that are infected with *N. risticii* bacteria;

b) extracts or fractions of (a) that are enhanced with respect to the concentration of the *N. risticii* bacteria contained within the infected host cells;

c) *N. risticii* bacteria enhanced extracts of (a) that contain remnants of the host cells;

d) isolated and purified *N. risticii* bacterial extracts of (a) that do not contain remnants of the host cells;

e) attenuated or inactivated bacteria;

f) isolated bacterial immunogens;

g) recombinant *N. risticii* proteins;

h) recombinant expression vectors that comprise nucleotide sequences, under the control of one or more promoters, that encode one or more recombinant *N. risticii* proteins (e.g., *N. risticii* strain specific antigens) which can be expressed by the recombinant expression vector; and i) *N. risticii* strain specific antigens.

In some embodiments an *N. risticii* isolate of the present invention, encodes an SSA #1 protein comprising an amino acid sequence that comprises 80% or greater, 90% or greater, 95% or greater, 98% or greater, and/or 99% or greater identity with the amino acid sequence of SEQ ID NO: 2. In some embodiments an *N. risticii* isolate of the present invention, encodes an SSA #2 protein comprising an amino acid sequence that comprises 80% or greater, 90% or greater, 95% or greater, 98% or greater, and/or 99% or greater identity with the amino acid sequence of SEQ ID NO: 11. In some embodiments an *N. risticii* isolate of the present invention, encodes an SSA #3 protein comprising an amino acid sequence that comprises 90% or greater, 95% or greater, 98% or greater, and/or 99% or greater identity with the amino acid sequence of SEQ ID NO: 18. In other embodiments an *N. risticii* isolate of the present invention, encodes an SSA #1 protein comprising an amino acid sequence that comprises 80% or greater, 90% or greater, 95% or greater, 98% or greater, and/or 99% or greater identity with the amino acid sequence of SEQ ID NO: 2, encodes an SSA #2 protein comprising an amino acid sequence that comprises 80% or greater, 90% or greater, 95% or greater, 98% or greater, and/or 99% or greater identity with the amino acid sequence of SEQ ID NO: 11, and encodes an SSA #3 protein comprising an amino acid sequence that comprises 90% or greater, 95% or greater, 98% or greater, and/or 99% or greater identity with the amino acid sequence of SEQ ID NO: 18.

As used herein the following terms shall have the definitions set out below:

"Isolated" when used herein means removed from its naturally occurring environment. Hence, isolated *N. risticii* bacterial cells broadly include those that have been removed from their naturally occurring environments, including without limitation arthropods, insects, infected animals and specimens from infected animals. Isolated *N. risticii* bacterial cells also include those that are contained within host cells as described herein, or separated therefrom, as well as those that are substantially free of other microorganisms, e.g., in a culture.

"Isolated bacterial immunogens" refers to bacterial immunogens that have been completely or partially separated from their respective source bacteria. Compositions of isolated bacterial immunogens can include some whole intact bacteria, portions or components of bacteria, whole intact host cell, portions or components of host cells comprising bacterial antigens, as well as antigens produced by physical, chemical, biological or molecular biological processes.

"*N. risticii* bacterial immunogens" as used herein include whole bacteria, as well as parts thereof, including proteins (lipoproteins, membranous proteins, cytosolic proteins), immunogenic fragments of such proteins, nucleic acids, lipids, saccharides, lipopolysaccharides or other biological molecules derived from the *N. risticii* bacteria. They may be present in live host cells and host cells that are killed or inactivated. The skilled artisan is generally familiar with techniques by which bacteria or host cells can be killed or inactivated. Such techniques include physical, chemical and biological means. Non-limiting examples of inactivation techniques include sonication, freeze-thaw techniques, pressure, treatment with heat, chemicals or enzymes. Non-limiting examples of chemical inactivation agents include treatment with binary ethyleneamine (BEA) and formalin (formaldehyde solution). Immunogens may also be the products of chemical, biological or molecular biological processes.

As used herein one amino acid sequence is 100% "identical" to a second amino acid sequence when the amino acid residues of both sequences are identical. Accordingly, an amino acid sequence is 50% "identical" to a second amino acid sequence when 50% of the amino acid residues of the two amino acid sequences are identical. The sequence comparison is performed over a contiguous block of amino acid residues comprised by a given protein, e.g., a protein, or a portion of the polypeptide being compared. In a particular embodiment, selected deletions or insertions that could otherwise alter the correspondence between the two amino acid sequences are taken into account.

As used herein, nucleotide and amino acid sequence percent identity can be determined using C, MacVector (MacVector, Inc. Cary, N.C. 27519), Vector NTI (Informax, Inc. MD), Oxford Molecular Group PLC (1996) and the Clustal W algorithm with the alignment default parameters, and default parameters for identity. These commercially available programs can also be used to determine sequence similarity using the same or analogous default parameters. Alternatively, an Advanced Blast search under the default filter conditions can be used, e.g., using the GCG (Genetics Computer Group, Program Manual for the GCG Package, Version 7, Madison, Wis.) pileup program using the default parameters.

As used herein, the term "vaccine(s)" means and refers to a product, the administration of which is intended to elicit an immune response that can prevent and/or lessen the severity of one or more infectious diseases.

As used herein, an "immune response" refers to the subject animal's active immunity due to having received one or more vaccines. The immune response can include the production of antibodies to the antigen or immunogen present in the vaccine. "Immune response" in a subject refers to the development of a humoral immune response, a cellular immune response, or a humoral and a cellular immune response to an antigen. Immune responses may be measured using standard immunoassays and neutralization assays, which are known in the art.

"Preventing infection" and like terms means to prevent or inhibit the replication of the bacteria that cause the identified disease, to inhibit transmission of the bacteria or virus, to prevent the bacteria from establishing itself in its host animal or to alleviate the symptoms of the disease caused by infection. The treatment is considered therapeutic if there is a reduction in bacterial load.

"Protection," "Protecting" and the like, as used herein with respect to bacteria, mean that the vaccine prevents or reduces the symptoms of the disease caused by the organism from which the antigen(s) used in the vaccine is derived. The terms "protection," "protecting" and the like also mean that the vaccine may be used to "treat" the disease or one of more symptoms of the disease that already exists in a subject.

"Treating" refers to reversing, alleviating, inhibiting the progress of, or preventing a disorder, condition or disease to which such term applies, or to preventing one or more symptoms of such disorder, condition or disease.

"Pharmaceutically acceptable" as used herein refers to substances (e.g., adjuvants, immunostimulants, carriers, diluents, emulsifying or stabilizing agents) that are within the scope of sound medical judgment, suitable for use in contact with the tissues of subjects without undue toxicity, irritation, allergic response, and the like, commensurate with a reasonable benefit-to-risk ratio, and effective for their intended use. Pharmaceutically acceptable substances do not interfere with the effectiveness of the therapeutic agent.

A vaccine contains an antigen (or, "active agent," "immunogen," "therapeutic agent," or "immunogenic composition"), including a host cell infected with *N. risticii* bacteria, whole intact bacteria, or bacterial fractions or parts or biomolecules that act to stimulate the immune system in an animal, particularly the SSA's of the novel strain. An antigen may be a live attenuated or killed preparation of bacteria-infected host cells, live attenuated or killed bacteria, living irradiated cells, crude fractions or purified bacterial immunogens. A vaccine can comprise enriched, isolated or purified antigen. The vaccines can be made from inactivated or killed cultures of infected host cells, or inactivated or killed bacteria or alternatively, comprise a recombinant expression vector that comprises one or more nucleotide sequence, under the control of one or more promoters, that encode one or more recombinant *N. risticii* proteins (e.g., *N. risticii* strain specific antigens) which can be expressed by the recombinant expression vector.

A vaccine of the present invention may also comprise a combination of antigens from more than one *N. risticii* bacterial species and/or a combination of *N. risticii* antigens. For example, a vaccine of the present invention can comprise a combination of two or more of the following strains: *N. risticci* Oregon, *N. risticci* 90-12, *N. risticci* Illinois, *N. risticci* New York, *N. risticci* 90-12, *N. risticci,* 25-D, and/or *N. risticci*, Michigan. In a particular embodiment of this type, the vaccine can comprise *N. risticci* Oregon, and *N. risticci* 90-12. In another such embodiment, the combination vaccine can comprise *N. risticci* Oregon, and *N. risticci* New York. In yet another embodiment, the combination vaccine can comprise *N. risticci* New York and *N. risticci*, Michigan. In still another embodiment, the vaccine can comprise *N. risticci* Oregon, *N. risticci* 90-12, and *N. risticci* New York. All other such combinations are further envisioned by the present invention. In addition, any *N. risticii* vaccine of the present invention can further include antigens from other pathogens (e.g. viral, bacterial parasitical or fungal), as described further below.

Vaccines made from material cultured according to the present invention comprise a therapeutically effective amount of the antigen. In the context of this disclosure, a "therapeutically effective amount" refers to an amount of an antigen or vaccine that would induce an immune response in an animal receiving the antigen or vaccine that is adequate to prevent or ameliorate signs or symptoms of disease caused by infection with a *N. risticii* bacterium. Humoral immunity or cell-mediated immunity, or both humoral and cell-mediated immunity, may be induced. The immunogenic response of an animal to a vaccine may be evaluated, e.g., indirectly through measurement of antibody titers, via microscopic analysis, or directly through monitoring signs and symptoms after challenge with wild type strain. The protective immunity conferred by a vaccine may be evaluated by measuring, e.g., reduction in clinical signs such as mortality, morbidity, body temperature and overall physical condition and overall health and performance of the subject. The amount of a vaccine that is therapeutically effective may vary depending on the particular antigen used, or the condition of the subject, and may be determined by one skilled in the art through well known means.

The novel *N. risticii* strains according to the present invention can also be used to diagnose diseases or illnesses caused by *N. risticii* bacteria. Non-limiting examples of such diagnostic applications include use of bacterial fractions, proteins or other biomolecules in antibody binding assays. The bacterial fractions, proteins or other biomolecules may also be used to generate polyclonal or monoclonal antibodies for such assays.

Host Cell Growth

Host cells for culturing bacterial organisms according to the present invention are first prepared prior to infecting with the desired bacterial organism. Examples of appropriate cell lines include: feline embryonic fibroblast cells, mouse macrophage P388D1 cells (ATCC No.: TIB 63), or a human histiocyte (HH) cell line (ATCC No. U937).

In one embodiment a sample of an isolated feline embryonic fibroblast cell line is seeded into media for either suspended or adherent growth. As used herein, adherent growth conditions exist when a layer of cells coats surfaces contained within the vessel in which the cells are cultured. The surfaces can include the interior surface of the vessel itself, or surfaces of glass or polymeric beads contained within the vessel to increase surface area. Microcarriers can also be used to increase surface area and host cell growth. In contrast to adherent growth, host cells may also be grown in suspension, in which the host cells need not bind to surfaces within the culturing vessel.

The skilled artisan is generally familiar with the varieties of culturing media that may be used to grow the host cells. The host cell growth media may be derived from animals. Alternatively, the host cell growth media may be vegetable or yeast based, and may be animal protein-free. The growth media may be derived from soy bean extracts or from other protein-rich plants or protein-rich plant food products including, for example, legumes. Non-limiting examples of specific media useful for growing host cells include Dulbecco's Modified Eagle's Medium (D-MEM), Eagle's Minimal Essential Media (MEM), Glasgow-Minimal Essential Media, RPMI1640, OptiMEM, and AIM V. The growth media may contain or be supplemented with fetal bovine serum (FBS), tryptose solution, lactos-albumin hydrosolate solution, L-glutamine, sodium bicarbonate; lactalbumin hydrolysate, Polymyxin B, sodium pyruvate, glucose, and/or magnesium sulfate.

Fresh growth media may be fed or replenished to the host cells prior to or after infection or exposure of the host cells to the bacteria. Cells may be grown at 36-38° C. for 2-9 days at 5% $CO_2$.

Infecting the Host Cells

The host cells may be exposed to or infected with bacterial organisms by bringing the host cells into contact with other eukaryotic cells known to be infected with the bacterial organisms. The skilled artisan is familiar with determining whether such other eukaryotic cells from a mammal, for example, are infected with such bacterial organisms. The infected mammalian cells may be derived from any tissue, including the spleen, liver, pancreas, lungs, heart or other muscle tissue, brain, gall bladder, blood, kidneys, lymph nodes or stomach. The infected mammalian cells may be prepared from a tissue extract via blender homogenization in an appropriate isotonic solution. The homogenate can then be used to innoculate (i.e., infect) a culture of host cells, applied as a layer over the host cells or simply brought into contact with them.

Alternatively, the host cells may be exposed to or infected with isolated bacterial organisms. The skilled artisan is familiar with techniques of isolating such bacterial organisms, or can obtain stocks of isolated bacterial organisms from a biological depository.

The growth medium used to prepare host cells prior to contact with bacteria may be the same as the medium used to propagate the host cells after such contact. The bacteria-exposed (or infected) host cells may be cultured for up to 95 days, up to 35 days, or for about 5 to 14 days, to achieve a titer of $0.1\times10^4$ $TCID_{50}$ (Tissue Culture Infectious Dose), and then the culture may be harvested and processed.

Harvesting

The bacteria infected host cells may be harvested by collecting the tissue cell culture fluids and/or cells. The host cells may be harvested from the media (and the culture vessels) with the bacterial cells contained with the walls of the host cells. Alternatively, during harvesting the concentration of the bacteria may be enriched by techniques that improve the liberation of the infective bacterial cells from the growth substrate, e.g., sonication, freeze thawing, heating, pressure or chemical or selective enzymatic lysis of the eukaryotic host cells. An enriched harvest of bacteria can include material that is free of host cells or host cell material. Alternatively, an enriched harvest of bacteria can include material that contains host cells or host cell material.

Inactivating

The skilled artisan is generally familiar with the techniques by which bacteria or host cells can be killed or inactivated. Such techniques include, physical, chemical and biological means. Non-limiting examples of inactivation techniques include sonication, freeze-thaw techniques, pressure, treatment with heat, chemicals or enzymes. Non-limiting examples of chemical inactivation agents include treatment with binary ethyleneimine (BEI), formalin (formaldehyde solution), beta-propiolactone, merthiolate, gluteraldehyde, sodium dodecyl sulfate, or the like, or a mixture thereof. The host cells can also be inactivated by heat or psoralen in the presence of ultraviolet light. These chemical inactivation agents or physical inactivation means can also be used to inactivate the bacterial cells after their having been extracted or separated from the host cells.

Formulating

The inactivated, infected host cells or enriched bacterial cells can serve as the antigen and may be formulated as a liquid suspension or may be lyophilized for its use in the preparation of a vaccine against diseases caused by the organisms. Material cultured according to the present invention can be formulated with any pharmaceutically acceptable adjuvants, immunostimulants, carriers, diluents, emulsifying or stabilizing agents, non-limiting examples of which are discussed below. The skilled artisan, however, would recognize that other adjuvants, immunostimulants, carriers, diluents, emulsifying agents or stabilizing agents may be used in formulating vaccines based upon material cultured according to the present invention.

Adjuvants & Immunostimulants

An adjuvant in general is a substance that boosts the immune response of the target in a non-specific manner. Many different adjuvants are known in the art. Non-limiting examples of adjuvants that may be used in the formulation of a vaccine made with material according to the present invention include aluminum salts (e.g., alum, aluminum hydroxide, aluminum phosphate, aluminum oxide), cholesterol, monophosphoryl lipid A adjuvants, amphigen, tocophenols, monophosphenyl lipid A, muramyl dipeptide, oil emulsions, glucans, carbomers, block copolymers, Avridine lipid-amine adjuvant, heat-labile enterotoxin from *E. coli* (recombinant or otherwise), cholera toxin, muramyl dipeptide, Freund's Complete and-Incomplete adjuvant, vitamin E, non-ionic block polymers and polyamines such as dextransulphate, carbopol, pyran, saponins and saponin derivatives, block copolymers, and adjuvants such as those identified in U.S. Pat. Nos. 4,578,269, 4,744,983, 5,254,339, which are all herein fully incorporated by reference. Non-limiting examples of peptides that can serve as adjuvants include muramyldipeptides, dimethylglycine, or tuftsin. Non-limiting examples of oils that can serve as adjuvants include mineral oils, vegetable oils, animal oils and emulsions thereof.

Vaccines made from material according to the present invention may be formulated as oil-in water emulsions, as water-in-oil emulsions or as water-in-oil-in-water emulsions. Non-limiting examples of oil-in-water emulsions include paraffin oil-in-water emulsions, or emulsions made from one or more of squalene, block copolymers of ethylene oxide and propylene oxide, polysorbate surfactants, and/or threonyl analogs of muramyl dipeptide.

Oils used as adjuvants may be metabolizable by the subject receiving the vaccine such as vegetable or animal oils. Such oils typically consist largely of mixtures of triacylglycerols, also known as triglycerides or neutral fats. These nonpolar, water insoluble substances are fatty acid triesters of glycerol. Triacylglycerols differ according to the identity and placement of their three fatty acid residues.

Adjuvants may also consist of components that cannot be metabolized by the body of the animal subject to which the emulsion is administered. Non-metabolizable oils suitable for use in the emulsions of the present invention include alkanes, alkenes, alkynes, and their corresponding acids and alcohols, the ethers and esters thereof, and mixtures thereof. The individual compounds of the oil may be light hydrocarbon compounds, e.g., compounds having 6 to 30 carbon atoms. The oil may be synthetically prepared or purified from petroleum products. Non-limiting examples of non-metabolizable oils for use in the preparation of vaccines based upon material cultured according to the present invention include mineral oil, paraffin oil, and cycloparaffins, for example. The term "mineral oil" refers to a non-metabolizable adjuvant oil that is a mixture of liquid hydrocarbons obtained from petrolatum via a distillation technique. The term is synonymous with "liquefied paraffin," "liquid petrolatum" and "white mineral oil." The term is also intended to include "light mineral oil," i.e., oil which is similarly obtained by distillation of petrolatum, but which has a slightly lower specific gravity than white mineral oil.

Other compounds capable of enhancing a humoral immunity response that may be used in the formulation of vaccines based upon material cultured according to the present invention include, without limitation, ethylene maleic anhydrate (EMA) copolymer, latex emulsions of a copolymer of styrene with a mixture of acrylic acid and methacrylic acid.

In addition to the adjuvant, a vaccine based upon material cultured according to the present invention can include immunomodulatory agents such as, e.g., interleukins, interferons, or other cytokines (e.g., Th1-related cytokines, such as interleukin-12 (IL-12), interleukin-18 (IL-18), or gamma interferon).

The amount of adjuvant or immunostimulant added in a vaccine formulation based upon material cultured according to the present invention depends on the nature of the adjuvant or immunostimulant itself. The skilled artisan is capable of selecting an amount that is sufficient to enhance an immune response to the bacterial immunizing agent.

Carriers

Pharmaceutically acceptable carriers suitable for use in vaccines comprising material according to the present invention may be any conventional liquid carrier suitable for veterinary pharmaceutical compositions, including balanced salt solutions suitable for use in tissue culture media. Pharmaceutically acceptable carriers are understood to be compounds that do not adversely effect the health of the animal to be vaccinated, at least not to the extent that the adverse effect is worse than the effects seen when the animal is not vaccinated. Suitable carriers also include sterile water, saline, aqueous buffers such as PBS, solvents, diluents, isotonic agents, buffering agents, dextrose, ethanol, mannitol, sorbitol, lactose and glycerol, and the like.

Vehicle

Vaccines formulated from material according to the present invention may also comprise a vehicle. A vehicle is a compound to which the host cells, bacterial cells, or proteins, protein fragments, nucleic acids or parts thereof adhere, without being covalently bound to it. Non-limiting examples of such vehicles include bio-microcapsules, micro-alginates, liposomes and macrosols. Some materials that serve as adjuvants can also serve as vehicles such as aluminum-hydroxide, aluminum phosphate, aluminum sulphate or aluminum oxide, silica, kaolin, and bentonite, all known in the art.

Stabilizers

Often, a vaccine is mixed with stabilizers, e.g., to protect degradation-prone components from being degraded, to enhance the shelf-life of the vaccine, or to improve freeze-drying efficiency. Non-limiting examples of stabilizers that may be added to vaccine formulations based upon material cultured according to the present invention include SPGA, skimmed milk, gelatins, bovine serum albumin, carbohydrates (e.g., sorbitol, mannitol, trehalose, starch, sucrose, dextran or glucose), proteins (e.g., albumin, casein or degradation products thereof), non-animal origin stabilizers, and buffers (e.g., alkali metal phosphates).

Multivalent Vaccines

An immunogen according to the present invention may be formulated in a vaccine comprising one or more additional antigens. Additional immunoactive component(s) may be whole parasites, bacteria or viruses (inactivated or modified live), or a fractionated portion or extract thereof (e.g., proteins, lipids, lipopolysacharides, carbohydrates or nucleic acids).

Where the immunogen according to the present invention is used in an equine vaccine, antigens from other pathogens may be added into the formulation. Non-limiting examples of other pathogens for which additional antigens may be added include one or more (including all) of the following: Tetanus, Rabies, Eastern Encephalomyelitis, Western Encephalomyelitis, influenza virus, herpesvirus, West Nile virus (including a yellow fever virus/west nile virus chimeric flavivirus, live or killed, see e.g., US 2009/0246233, hereby incorporated by reference in its entirety) and Venezuelan Encephalomyelitis. Alternatively, a vaccine based upon material according to the present invention may be administered simultaneously with other live or inactivated vaccines.

Freeze-Drying/Reconstitution

For reasons of stability or economy, vaccines based upon material cultured according to the present invention may be freeze-dried. In general this will enable prolonged storage at temperatures above 0° C., e.g., at 4° C. Procedures for freeze-drying are known to persons skilled in the art. Equipment for freeze-drying at different scales is available commercially. To reconstitute the freeze-dried vaccine, it may be suspended in a physiologically acceptable diluent. Such diluents may be as simple as sterile water, a physiological salt solution or other carrier as discussed above.

Dosaging

Vaccines based upon material according to the present invention may be formulated in a dosage unit form to facilitate administration and ensure uniformity of dosage. A dosage unit as it pertains to the vaccine composition refers to physically discrete units suitable as unitary dosages for animals, each unit containing a predetermined quantity of bacterial immunogen calculated to produce the desired immunogenic effect in association with the required adjuvant system and carrier or vehicle.

The effective immunizing amount of bacterial immunogen can vary depending upon the chosen strain or strains and may be any amount sufficient to evoke a protective immune response. For example, amounts wherein the dosage unit comprises at least about $1\times10^4$ $TCID_{50}$ inactivated bacterin are suitable.

Administering

Administration of the vaccine to a subject results in stimulating an immune response in the subject mammal. The route of administration for vaccines according to the present invention may be administered to the mammalian target according to methods known in the art. Such methods include, but are not limited to, intradermal, intramuscular, intraocular, intraperitoneal, intravenous, mucosal, oral, oronasal, and subcutaneous, as well as inhalation, suppository, or transdermal. The vaccine may be administered by any means that includes, but is not limited to, syringes, nebulizers, misters, needleless injection devices, or microprojectile bombardment gene guns.

Alternative routes of application that are feasible are by topical application as a drop, spray, gel or ointment to the mucosal epithelium of the eye, nose, mouth, anus, or vagina, or onto the epidermis of the outer skin at any part of the body; by spray as aerosol or powder. Alternatively, application may be via the alimentary route, by combining with the food, feed or drinking water, e.g., as a powder, a liquid, or tablet, or by administration directly into the mouth as a liquid, a gel, a tablet, or a capsule, or to the anus as a suppository. The preferred application route is by intramuscular or by subcutaneous injection.

The vaccine according to the invention may be in several forms, e.g., a liquid, a gel, an ointment, a powder, a tablet, or a capsule, depending on the desired method of application to the target. The scheme of the application of the vaccine according to the invention to the target mammal may be in single or multiple doses, which may be given at the same time or sequentially, in a manner compatible with the dosage and formulation, and in such an amount as will be immunologically effective.

Challenge Model

In order to effectively study and evaluate the pathogenic mechanisms of the bacteria and the defense mechanisms of the host mammals, and thereby to advance the vaccine art and improve vaccine products, an effective challenge model should be employed.

A challenge model, for example, may be based upon the percentage of test animals that demonstrate persistent and severe clinical symptoms commonly associated with the disease.

Several other cellular diagnostic methods exist to determine the presence of infection. For example, the presence of infection may be determined by direct or indirect immunofluorescence. Other methods to detect infection include staining, e.g., Giemsa, Wright/Giemsa. Acridine Orange can also be utilized to stain the organisms.

Unless defined otherwise, all technical and scientific terms used herein have the same meaning as commonly understood by one of ordinary skill in the art to which this invention belongs. All publications mentioned herein are hereby wholly incorporated by reference.

For a clearer understanding of the invention, examples are set forth below. These examples are merely illustrative and are understood to not limit the scope or underlying principles of the invention in any way. Indeed, various modifications of the invention, in addition to those shown and described herein, will become apparent to those skilled in the art from the examples set forth hereinbelow and the foregoing description. Such modifications are also intended to fall within the scope of the appended claims.

EXAMPLES

Example 1

Identification and Characterization of *Neorickettsia Risticii* Isolates from Oregon, New York and Michigan A blood sample was obtained from a horse in Oregon showing clinical signs of Potomac Horse Fever. We found the Oregon (OR) sample to be positive for *N. risticii* by PCR and by immunofluorescent antibody testing (IFA). We discovered this unique *N. risticii* Oregon strain to be distinct from the 90-12 strain. When tested by IFA, it did not react with a monoclonal antibody to the 90-12 strain.

Horses vaccinated with the 90-12 strain of *N. risticii* (study E-05-09-PHF) were challenged with the *N. risticii* Oregon. The vaccinated horses were not protected from disease. Serologically, the 90-12 vaccinated horses had no detectable antibody response to *N. risticii* Oregon after vaccination, and most of the unvaccinated control horses challenged with *N. risticii* Oregon did not have a detectable antibody response to the 90-12 strain 23 days after challenge.

A blood sample was obtained from a horse in New York showing clinical signs of Potomac Horse Fever. Unlike the corresponding Oregon isolate disclosed above, the New York (NY) sample was shown to react with the monoclonal antibody to the 90-12 strain by IFA. When horses vaccinated with the 90-12 strain of *N. risticii* (study E-01-09-PHF) were challenged with *N. risticii* New York, the vaccinated horses showed a significant reduction in clinical disease and bacterial isolation.

A blood sample was obtained from a horse in Michigan showing clinical signs of Potomac Horse Fever. We found the Michigan (MI) sample to be positive for *N. risticii* by PCR and by immunoflorescent antibody testing. We discovered this unique *N. risticii* strain to be distinct from the 90-12 strain. When tested by Western Blot, it did not react with a monoclonal antibody to the 90-12 strain.

Example 2

*N. Risticii* Host Animal Protection Studies

TABLE 1

PHF Vaccine Formulations

| Component | Lot Number | Volume |
|---|---|---|
| E-13-06-PHF Vaccine | | |
| *N. risticii* (90-12) antigen | 120306 | 300 mL |
| Havlogen Adjuvant | 024 | 200 mL |
| PBS #2 | 095 | 1276 mL |
| Glycerin | 005 | 200 mL |
| EDTA (240 mM) | 006 | 20 mL |
| Thimerosal (10% stock solution) | 025 | 2 mL |
| Phenol Red (1% stock solution) | 005 | 2 mL |
| Total Volume: | | 2000 mL |
| E-01-09-PHF Vaccine | | |
| *N. risticii* (90-12) antigen | 101608 | 52 mL |
| Carbopol 971P Adjuvant | 002 | 300 mL |
| PBS #2 | 436 | 2642 mL |
| Thimerosal (10% stock solution) | 043 | 2.95 mL |
| Phenol Red (1% stock solution) | 008 | 3 mL |
| Total Volume: | | 3000 mL |
| E-05-09-PHF Vaccine | | |
| *N. risticii* (90-12) antigen | 013009 | 48 mL |
| Carbopol 971P Adjuvant | 003 | 200 mL |
| PBS #2 | 504 | 1748 mL |
| Thimerosal (10% stock solution) | 043 | 1.95 mL |
| Phenol Red (1% stock solution) | 008 | 1.95 mL |
| Total Volume: | | 2000 mL |
| E-03-10-PHF Vaccine | | |
| *N. risticii* (Oregon) antigen | 120809 | 5.2 mL |
| Carbopol 971P Adjuvant | 003 | 10 mL |
| PBS #2 | 601 | 84.6 mL |
| Thimerosal (10% stock solution) | 062 | 0.095 mL |
| Phenol Red (1% stock solution) | 008 | 0.095 mL |
| Total Volume: | | 100 mL |

Example 2a 90-12 Vaccination/90-12 Challenge (Study E-13-06-PHF)

The purpose of this study was to evaluate the efficacy of an inactivated vaccine containing the 90-12 strain of *N. risticii*, against challenge with the homologous 90-12 *N. risticii* isolate, in host animals.

Eight month-old horses, antibody negative to *N. risticii*, were randomized into two treatment groups, with fifteen horses per group. The horses were vaccinated twice intramuscularly three weeks apart with 1.0 mL of vaccine containing the inactivated 90-12 strain of *N. risticii* (Lot 120306), or with 1.0 mL of a placebo vaccine. The horses were challenged with the 90-12 strain of *N. risticii* at twenty-one days following the second vaccination. Horses were observed for 24 days post-challenge for clinical signs of PHF, and whole blood samples were collected daily from 6 to 24 days post-challenge for bacterial isolation and white blood cell (WBC) counts. The clinical signs of PHF disease include rectal body temperature of >1.5° F. over baseline temperature (established as the average of the rectal temperatures for 3 days prior to challenge), anorexia, depression, or diarrhea, and laminitis.

Clinical Disease

Horses that exhibited at least one clinical sign of PHF post-challenge were classified as affected. Fifteen of the fifteen (100%) placebo-vaccinated control horses were affected. None of the fifteen (0%) horses vaccinated with *N. risticii* 90-12 vaccine were affected.

The prevented fraction was 1.00 with a 95% confidence interval of [0.77, 1.00], therefore the data supports the claim of "aid in the prevention of disease caused by *N. risticii*".

*N. Risticii* Bacteremia

Horses with a positive isolation from a buffy coat sample were classified as affected. Fifteen of the fifteen (100%) placebo-vaccinated control horses were bacteremic for 5-8 days following challenge. Six of the fifteen (40%) horses vaccinated with *N. risticii* 90-12 vaccine were bacteremic for only one day following challenge.

The prevented fraction was 0.60 with a 95% confidence interval of [0.32, 0.80], therefore the data supports the claim of "aid in the prevention of bacteremia caused by *N. risticii*".

Conclusion

The data demonstrated that inactivated *N. risticii* 90-12 strain vaccine is protective against challenge with homologous *N. risticii* strain 90-12.

Example 2b 90-12 Vaccination/NY Challenge (Study E-01-09-PHF)

The purpose of this study was to evaluate the efficacy of an inactivated vaccine containing the 90-12 strain of *N. risticii*, against challenge with the heterologous NY *N. risticii* strain, in host animals.

Eleven month-old horses, antibody negative to *N. risticii*, were randomized into two treatment groups, with fifteen horses per group. The horses were vaccinated twice intramuscularly three weeks apart with 1.0 mL of vaccine containing the inactivated 90-12 strain of *N. risticii* (Lot 101608), or with 1.0 mL of a placebo vaccine. The horses were challenged with the NY strain of *N. risticii* fourteen days following the second vaccination. Horses were observed for 21 days following challenge for clinical signs of disease associated with PHF, and whole blood samples were collected daily from 6 to 18 days post-challenge for bacterial isolation. The clinical signs of PHF disease include rectal body temperature of >1.5° F. over baseline temperature (established as the average of the rectal temperatures for 3 days prior to challenge), anorexia, depression, diarrhea, colic or laminitis, when associated with the other clinical signs of PHF.

Clinical Disease

Horses that exhibited at least one clinical sign of PHF post-challenge on at least one day post-challenge were classified as affected.

The severity of clinical disease was considered to be the number of post-challenge days with at least one clinical sign, and was analyzed using the Wilcoxon Rank Sum test. The mitigated fraction was 0.54 with a lower confidence interval of 0.17, therefore the data supports the claim of "aid in the reduction of severity of clinical disease caused by *N. risticii*".

*N. Risticii* Bacteremia

Horses with a positive isolation from a buffy coat sample were classified as affected. The placebo-vaccinated control horses had an average of 6.4 days of positive isolations following challenge. The horses vaccinated with inactivated *N. risticii* 90-12 strain vaccine had an average of 3.5 days of positive isolations following challenge.

The duration of bacteremia was analyzed using the Wilcoxon Rank Sum test. The mitigated fraction was 0.59 with a lower confidence interval of 0.24, therefore the data supports the claim of "aid in the reduction of bacteremia caused by *N. risticii*".

Conclusion

The data demonstrated that inactivated *N. risticii* 90-12 strain vaccine reduces the severity of clinical disease and bacteremia, following challenge with heterologous *N. risticii* strain NY.

Example 2c 90-12 Vaccination/OR Challenge (Study E-05-09-PHF)

The purpose of this study was to evaluate the efficacy of an inactivated vaccine containing only the OR strain of *N. risticii*, against challenge with the OR *N. risticii* isolate, in host animals.

Five to six month-old horses, antibody negative to *N. risticii*, were randomized into two treatment groups, with fifteen horses per group. The horses were vaccinated twice intramuscularly three weeks apart with 1.0 mL of the inactivated vaccine containing the inactivated 90-12 strain of *N. risticii* (Lot 013009), or with 1.0 mL of a placebo vaccine. The horses were challenged with the heterologous OR strain of *N. risticii* fourteen days following the second vaccination. Horses were observed for 21 days post-challenge for clinical signs of PHF, and whole blood samples were collected daily from 6 to 18 days post-challenge for bacterial isolation. The clinical signs of PHF disease include rectal body temperature of >1.5° F. over baseline temperature (established as the average of the rectal temperatures for 3 days prior to challenge), anorexia, depression, or diarrhea, and additionally colic or laminitis, when associated with the other clinical signs of PHF.

Clinical Disease

Horses that exhibited at least one clinical sign of PHF post-challenge were classified as affected. Twelve of the fifteen (80%) placebo-vaccinated control horses were affected, and twelve of the fifteen (80%) horses vaccinated with inactivated *N. risticii* 90-12 strain vaccine were affected. The inactivated *N. risticii* 90-12 strain vaccine provided no protection from clinical disease caused by heterologous OR strain *N. risticii.*

*N. Risticii* Bacteremia

Horses with a positive isolation from a buffy coat sample were classified as affected. Two of the fifteen (13%) placebo-vaccinated control horses had a positive isolation on one day following challenge. Eight of the fifteen (53%) horses vaccinated with inactivated *N. risticii* 90-12 strain vaccine had a positive isolation on at least one day following challenge. The inactivated *N. risticii* 90-12 strain vaccine provided no protection from bacteremia caused by heterologous OR strain *N. risticii.*

Conclusion

The data demonstrates that the inactivated *N. risticii* 90-12 strain vaccine did not protect against, or reduce the severity of, clinical disease or bacteremia following challenge with heterologous *N. risticii* strain OR.

Example 2d

OR Vaccination/OR Challenge (Study E-03-10-PHF)

The purpose of this study was to evaluate the efficacy of an inactivated vaccine containing only the OR strain of *N. risticii*, against challenge with the homologous OR *N. risticii* isolate, in host animals.

Ten to twelve month-old horses, antibody negative to *N. risticii*, were enrolled in the study and were randomized into treatment groups, with eight horses per group. The horses were vaccinated twice intramuscularly three weeks apart with 1.0 mL of the inactivated vaccine containing the OR strain of *N. risticii* (Lot 120809), or with 1.0 mL of a placebo vaccine. The horses were challenged with the OR strain of *N. risticii* at twenty days following the second vaccination. Horses were observed for 24 days post-challenge for clinical signs of PHF, until resolution of the clinical signs, and whole blood samples were collected daily from 7 to 18 days post-challenge for bacterial isolation. Horses were weighed prior to challenge and following the post-challenge period, as an additional non-subjective indication of illness, anorexia, and diarrhea caused by PHF, and percent weight gains or losses during the post-challenge period were determined. The clinical signs of PHF disease include rectal body temperature of >1.5° F. over baseline temperature (established as the average of the rectal temperatures for 4 days prior to challenge), anorexia, depression, or diarrhea, and additionally colic or laminitis, when associated with the other clinical signs of PHF.

Clinical Disease

Horses that exhibited at least one clinical sign of PHF post-challenge were classified as affected. Seven of the eight (88%) placebo-vaccinated control horses were affected. Three of the eight (38%) horses vaccinated with experimental *N. risticii* OR strain vaccine were affected.

The Fisher test p-value was 0.0594. The proportion of affected horses vaccinated with *N. risticii* OR strain vaccine was marginally less than the proportion of horses vaccinated with placebo.

Severity of Disease

To evaluate disease severity, the number of post-challenge days with at least one clinical sign of PHF was analyzed using the Wilcoxon Rank Sum test. The p-value was 0.0485, therefore the number of post-challenge days with at least one clinical sign of PHF for horses vaccinated with *N. risticii* OR strain vaccine was marginally less than for the placebo-vaccinated horses.

The Wilcoxon Rank Sum test was also used to evaluate the number of clinical signs of PHF present during the post-challenge period, as an additional measure of disease severity. The p-value was 0.0485, indicating that the total number of clinical signs of PHF present during the post-challenge period was marginally less for the horses vaccinated with experimental *N. risticii* OR strain vaccine than for the placebo-vaccinated control horses.

*N. Risticii* Bacteremia

Horses with a positive isolation from a buffy coat sample were classified as affected. Two of the eight (25%) placebo-vaccinated control horses had a positive isolation on one day following challenge. One of the eight (13%) horses vaccinated with experimental *N. risticii* OR strain vaccine had a positive isolation on one day following challenge.

The Fisher test p-value was 0.3354, therefore there was no statistical difference in bacteremia between the horses vaccinated with experimental *N. risticii* OR strain vaccine and the placebo-vaccinated horses.

Weight

Horses were weighed prior to and following challenge. Four of the eight placebo-vaccinated control horses lost weight during the post-challenge period, and the average percent of body weight gain for all eight horses was only 0.3%. The horses vaccinated with experimental *N. risticii* OR strain vaccine had an average percent weight gain of 5.2%, and none of the eight vaccinated horses lost weight.

Conclusion

This data demonstrates that vaccination of horses with *N. risticii* OR strain vaccine reduces the incidence and severity of clinical PHF disease, compared to placebo-vaccinated control horses, following challenge with homologous OR strain *N. risticii*. Table 2 provides a comparison of the clinical results of sixteen horses challenged with *N. risticii* Oregon, eight of which received a vaccine containing the *N. risticii* Oregon isolate and eight of which received a placebo.

TABLE 2

| Treatment Group | Control Horses (Placebo) | Vaccinated Horses (Oregon strain) |
|---|---|---|
| No. of Horses with ≥1 Clinical Sign of PHF | 7/8 | 3/8 |
| No. of Horses with Fever | 5/8 | 1/8 |
| No. of Horses with Anorexia | 4/8 | 2/8 |
| No. of Horses with Depression | 1/8 | 0/8 |
| No. of Horses with Diarrhea | 3/8 | 1/8 |
| No. of Horses with Laminitis | 1/8 | 0/8 |
| No. of Horses with Bacteremia | 2/8 | 1/8 |
| Average % Weight Gain | 0.3 | 5.2 |

These data show that vaccination of horses with *N. risticii* Oregon strain vaccine reduces the incidence and severity of clinical PHF, compared to placebo-vaccinated control horses.

Example 3

Serological Cross-Reactivity of *N. Risticii* Strains

Immunofluorescent antibody (IFA) testing was performed on sera collected from horses following vaccination and/or challenge with various strains of *N. risticii*, to measure the antibody reactivity against the five different strains of *N. risticii*. For the IFA assay, fixed feline embryonic fibroblast (FEF) cells, infected with one of the *N. risticii* strains (OR, 90-12, NY, MI, or 25-D), were reacted with serial dilutions of the equine serum samples. The plates were read using a fluorescence microscope for positive fluorescence, as indicated by bright green, specific cytoplasmic staining. The antibody titer was the reciprocal of the highest serum dilution that showed positive fluorescence.

The IFA results show that for most strains of *N. risticii* there is some serological cross-reactivity to other strains of *N. risticii*, but there appears to be very little cross-reactivity in sera from horses challenged with the OR strain of *N. risticii*, to other strains of *N. risticii*. The OR strain of *N. risticii* appears to be highly unique antigenically.

TABLE 3

| Oregon Challenged Horses (21, 22 or 24 days post-challenge) | | | | | | | |
|---|---|---|---|---|---|---|---|
| Study No. | Horse ID | Oregon IFA Results | New York FA Results | 90-12 IFA Results | Michigan IFA Results | 25D IFA Results | OSU* IFA Results |
| E-05-09 | 121 | 1280 | 80 | 40 | 40 | 80 | 40 |
| E-05-09 | 123 | 2560 | 320 | 160 | 320 | 320 | 2560 |
| E-05-09 | 126 | 640 | 80 | <20 | 80 | 80 | 320 |
| E-05-09 | 127 | 320 | 40 | <20 | 40 | 40 | 40 |
| E-05-09 | 128 | 1280 | 40 | <20 | <20 | 20 | <20 |
| E-05-09 | 130 | 640 | <20 | <20 | <20 | 40 | <20 |
| E-05-09 | 132 | 640 | 80 | <20 | 20 | 40 | <20 |
| E-05-09 | 133 | 320 | <20 | <20 | <20 | <20 | <20 |
| E-05-09 | 136 | 1280 | <20 | <20 | <20 | <20 | <20 |
| E-05-09 | 137 | 1280 | 40 | <20 | 40 | <20 | <20 |
| E-05-09 | 138 | 640 | 20 | <20 | 40 | 40 | <20 |
| E-05-09 | 140 | 320 | <20 | <20 | <20 | <20 | <20 |
| E-05-09 | 144 | 640 | 20 | <20 | <20 | <20 | <20 |
| E-05-09 | 147 | 2560 | 80 | <20 | 80 | 160 | <20 |
| E-05-09 | 148 | 640 | 40 | <20 | 160 | 40 | <20 |
| E-07-08 | 2 | 1280 | <20 | <20 | <20 | <20 | NT |
| E-07-08 | 5 | 1280 | <20 | <20 | <20 | <20 | NT |
| E-07-08 | 10 | 640 | <20 | <20 | <20 | <20 | NT |
| E-07-08 | 22 | 640 | <20 | <20 | <20 | <20 | NT |
| E-07-08 | 11 | 1280 | 80 | <20 | 40 | <20 | NT |
| E-07-08 | 12 | 2560 | 80 | <20 | <20 | 160 | NT |
| E-07-08 | 17 | 640 | <20 | <20 | <20 | <20 | NT |
| E-07-08 | 21 | 640 | <20 | <20 | <20 | <20 | NT |
| E-10-10 | 328 | 80 | <20 | <20 | <20 | <20 | NT |
| E-10-10 | 331 | 640 | <20 | <20 | <20 | <20 | NT |
| E-10-10 | 333 | 160 | 40 | <20 | <20 | 40 | NT |
| E-10-10 | 337 | 320 | 80 | <20 | <20 | <20 | NT |
| E-10-10 | 336 | 1280 | 160 | <20 | 40 | <20 | NT |
| E-10-10 | 338 | 80 | <20 | <20 | <20 | <20 | NT |
| E-10-10 | 339 | 640 | 80 | <20 | 40 | 80 | NT |
| E-03-10 | 162 | 640 | 80 | 80 | 40 | 80 | NT |
| E-03-10 | 165 | 640 | <20 | 20 | <20 | 80 | NT |
| E-03-10 | 167 | 1280 | 80 | 40 | 40 | 20 | NT |
| E-03-10 | 173 | 640 | 80 | 80 | 80 | <20 | NT |

TABLE 3-continued

| Oregon Challenged Horses (21, 22 or 24 days post-challenge) | | | | | | | |
|---|---|---|---|---|---|---|---|
| Study No. | Horse ID | Oregon IFA Results | New York FA Results | 90-12 IFA Results | Michigan IFA Results | 25D IFA Results | OSU* IFA Results |
| E-03-10 | 177 | 320 | 40 | 40 | 40 | <20 | NT |
| E-03-10 | 179 | 640 | 40 | 40 | 40 | 40 | NT |
| E-03-10 | 214 | 640 | 80 | 80 | 80 | 80 | NT |
| E-03-10 | 216 | 640 | 40 | 40 | 40 | 40 | NT |
| Average: | | 859 | 53 | 27 | 42 | 46 | 208 |

TABLE 4

| Oregon Vaccinated and Challenged Horses (24 days post-challenge) | | | | | | |
|---|---|---|---|---|---|---|
| Study No. | Horse ID | Oregon IFA Results | New York IFA Results | 90-12 IFA Results | Michigan IFA Results | 25D IFA Results |
| E-03-10 | 171 | 1280 | 640 | 320 | 640 | 640 |
| E-03-10 | 175 | 2560 | 640 | 640 | 1280 | 1280 |
| E-03-10 | 204 | 1280 | 320 | 160 | 320 | 640 |
| E-03-10 | 208 | 1280 | 320 | 320 | 320 | 640 |
| E-03-10 | 213 | 1280 | 320 | 320 | 320 | 320 |
| E-03-10 | 217 | 1280 | 320 | 320 | 320 | 640 |
| E-03-10 | 218 | 1280 | 320 | 80 | 80 | 640 |
| E-03-10 | 219 | 2560 | 2560 | 2560 | 2560 | 2560 |
| Average: | | 1600 | 680 | 590 | 730 | 920 |

TABLE 5

| New York Challenged Horses (22 days post-challenge) | | | | | | | |
|---|---|---|---|---|---|---|---|
| Study No. | Horse ID | Oregon IFA Results | New York IFA Results | 90-12 IFA Results | Michigan IFA Results | 25D IFA Results | OSU IFA Results |
| E-07-08 | 4 | 160 | 640 | 320 | 320 | 640 | NT |
| E-07-08 | 6 | 40 | 160 | 80 | <20 | <20 | NT |
| E-07-08 | 14 | 160 | 1280 | 320 | 640 | 640 | NT |
| E-07-08 | 19 | 40 | 320 | 160 | 160 | 320 | NT |
| E-07-08 | 9 | 80 | 320 | 160 | 160 | 320 | NT |
| E-07-08 | 15 | 80 | 640 | 160 | 320 | 640 | NT |
| E-07-08 | 23 | 160 | 1280 | 320 | 320 | 320 | NT |
| E-07-08 | 24 | 80 | 1280 | 640 | 320 | 320 | NT |
| E-01-09 | 74 | <20 | 1280 | 1280 | 320 | 640 | 640 |
| E-01-09 | 76 | 160 | 1280 | 1280 | 640 | 640 | 640 |
| E-01-09 | 77 | 80 | 640 | 640 | 320 | 320 | 160 |
| E-01-09 | 78 | 80 | 640 | 1280 | 320 | 640 | 320 |
| E-01-09 | 79 | <20 | 640 | 1280 | 640 | 640 | 320 |
| E-01-09 | 81 | 160 | 320 | 640 | 160 | 320 | 80 |
| E-01-09 | 87 | 160 | 640 | 1280 | 640 | 640 | 320 |
| E-01-09 | 92 | <20 | 1280 | 1280 | 1280 | 640 | 1280 |
| E-01-09 | 93 | <20 | 2560 | 640 | 640 | 1280 | 640 |
| E-01-09 | 96 | 640 | 1280 | 640 | 1280 | 1280 | 1280 |
| E-01-09 | 97 | <20 | 1280 | 640 | 320 | 640 | 320 |
| E-01-09 | 98 | 160 | 2560 | 2560 | 1280 | 2560 | 1280 |
| E-01-09 | 100 | <20 | 2560 | 640 | 320 | 640 | 320 |
| E-01-09 | 102 | 80 | 1280 | 1280 | 640 | 320 | 320 |
| E-01-09 | 106 | <20 | 2560 | 640 | <20 | <20 | 320 |
| Average: | | 105 | 1162 | 790 | 481 | 627 | 549 |

TABLE 6

| 90-12 Challenged Horses (21 days post-challenge) | | | | | | |
|---|---|---|---|---|---|---|
| Study No. | Horse ID | Oregon IFA Results | New York IFA Results | 90-12 IFA Results | Michigan IFA Results | 25D IFA Results |
| E-08-08 | 27 | 80 | 1280 | 640 | 320 | 320 |
| E-08-08 | 30 | 640 | 1280 | 2560 | 1280 | 320 |

TABLE 6-continued

| 90-12 Challenged Horses (21 days post-challenge) | | | | | | |
|---|---|---|---|---|---|---|
| Study No. | Horse ID | Oregon IFA Results | New York IFA Results | 90-12 IFA Results | Michigan IFA Results | 25D IFA Results |
| E-08-08 | 32 | 80 | 1280 | 1280 | 640 | 640 |
| E-08-08 | 40 | 640 | 2560 | 5120 | 2560 | 5120 |
| E-08-08 | 45 | 320 | 2560 | 2560 | 2560 | 2560 |
| E-08-08 | 46 | 640 | 5120 | 2560 | 2560 | 2560 |
| E-08-08 | 48 | 320 | 2560 | 2560 | 1280 | 2560 |
| E-08-08 | 49 | 160 | 1280 | 640 | 640 | 1280 |
| E-08-08 | 52 | 160 | 1280 | 1280 | 640 | 1280 |
| E-08-08 | 53 | 160 | 1280 | 640 | 640 | 1280 |
| E-08-08 | 55 | 80 | 1280 | 640 | 640 | 320 |
| E-08-08 | 57 | 80 | 1280 | 640 | 640 | 640 |

TABLE 6-continued

| 90-12 Challenged Horses (21 days post-challenge) | | | | | | |
|---|---|---|---|---|---|---|
| Study No. | Horse ID | Oregon IFA Results | New York IFA Results | 90-12 IFA Results | Michigan IFA Results | 25D IFA Results |
| E-08-08 | 59 | 160 | 2560 | 5120 | 2560 | 2560 |
| E-08-08 | 66 | 640 | 2560 | 2560 | 5120 | 5120 |

TABLE 6-continued

| 90-12 Challenged Horses (21 days post-challenge) | | | | | | |
|---|---|---|---|---|---|---|
| Study No. | Horse ID | Oregon IFA Results | New York IFA Results | 90-12 IFA Results | Michigan IFA Results | 25D IFA Results |
| E-08-08 | 71 | 40 | 640 | 640 | 640 | 640 |
| Average: | | 280 | 1920 | 1963 | 1515 | 1813 |

TABLE 7

| 90-12 Vaccinated and Challenged Horses (21 days post-challenge) | | | | | | |
|---|---|---|---|---|---|---|
| Study No. | Horse ID | Oregon IFA Results | New York IFA Results | 90-12 IFA Results | Michigan IFA Results | 25D IFA Results |
| E-08-08 | 26 | 1280 | 10240 | 10240 | 5120 | 2560 |
| E-08-08 | 29 | 1280 | 10240 | 10240 | 2560 | 5120 |
| E-08-08 | 34 | 1280 | 5120 | 5120 | 2560 | 5120 |
| E-08-08 | 35 | 640 | 10240 | 10240 | 2560 | 5120 |
| E-08-08 | 36 | 1280 | 10240 | 10240 | 5120 | 10240 |
| E-08-08 | 37 | 1280 | 10240 | 10240 | 10240 | 10240 |
| E-08-08 | 38 | 1280 | 10240 | 10240 | 5120 | 5120 |
| E-08-08 | 39 | 2560 | 10240 | 10240 | 10240 | 10240 |
| E-08-08 | 41 | 1280 | 5120 | 2560 | 5120 | 10240 |
| E-08-08 | 44 | 2560 | 10240 | 10240 | 10240 | 10240 |
| E-08-08 | 50 | 1280 | 10240 | 10240 | 5120 | 10240 |
| E-08-08 | 51 | 640 | 5120 | 5120 | 5120 | 10240 |
| E-08-08 | 60 | 1280 | 2560 | 5120 | 5120 | 2560 |
| E-08-08 | 64 | 1280 | 5120 | 10240 | 10240 | 5120 |
| E-08-08 | 69 | 2560 | 5120 | 10240 | 10240 | 10240 |
| Average: | | 1451 | 8021 | 8704 | 6315 | 7509 |

TABLE 8

| Michigan Challenged Horses (21 days post-challenge) | | | | | | |
|---|---|---|---|---|---|---|
| Study No. | Horse ID | Oregon IFA Results | New York IFA Results | 90-12 IFA Results | Michigan IFA Results | 25D IFA Results |
| E-10-10 | 326 | 320 | 640 | 320 | 640 | 1280 |
| E-10-10 | 327 | <20 | <20 | <20 | 80 | 80 |
| E-10-10 | 335 | 320 | 2560 | 640 | 640 | 1280 |
| Average: | | 218 | 1072 | 325 | 453 | 880 |

TABLE 9

| 25D Challenged Horses (21 days post-challenge) | | | | | | |
|---|---|---|---|---|---|---|
| Study No. | Horse ID | Oregon IFA Results | New York IFA Results | 90-12 IFA Results | Michigan IFA Results | 25D IFA Results |
| E-10-10 | 329 | 40 | 160 | 40 | 40 | 320 |
| E-10-10 | 332 | <20 | 160 | 80 | 40 | 320 |
| E-10-10 | 334 | <20 | 320 | 160 | 160 | 640 |
| E-10-10 | 340 | <20 | 160 | 40 | 80 | 640 |
| Average: | | 21 | 200 | 80 | 80 | 480 |

NT = Not Tested,
NA = Not Applicable
<20 assigned a value of 15 for average titer calculations
Antigen Lots: Oregon Lot 012010, 90-12 Lot 101910, Michigan Lot 100510, New York Lot 101310, 25-D Lot 101210
*OSU = Oregon State University Veterinary Diagnostic Laboratory

Example 4

Western Blot Analysis of *N. Risticii* Strains

Western Blots were performed to evaluate the antibody reactivity and antigen banding patterns of rabbit and horse serum against the recombinant 85 kDa protein of the *N. risticii* 90-12 strain with FEF cells used to propagate *N. risticii* and against the 90-12, OR, NY, MI and 25-D strains of *N. risticii*. Rabbit serum lot 02x1808a was a pool of sera collected from four rabbits following hyperimmunization with purified recombinant 85 kDa protein from the 90-12 strain of *N. risticii*. Horse serum lot 112310 was a pool of sera collected from four horses following challenge with the 90-12, OR, NY, or MI strains of *N. risticii*. Horse serum lot 012809 was collected from a horse that had not previously been exposed to, vaccinated or challenged with *N. risticii*, and served as a negative control to identify non-specific reactivity to FEF cells and *N. risticii.*

The pooled serum from rabbits immunized with the recombinant 85 kDa protein of the *N. risticii* 90-12 strain reacted with the 85 kDa recombinant protein on the Western Blot at the expected molecular weight, and at the same approximate molecular weight for the 90-12 strain of *N. risticii*. (FIG. 1). The serum reacted at differing, lower molecular weight bands of approximately 50, 55, 60 and 55 kDa for the OR, NY, MI and 25-D strains of *N. risticii*, respectively. No reactions were observed for the FEF cells.

Figure 2:
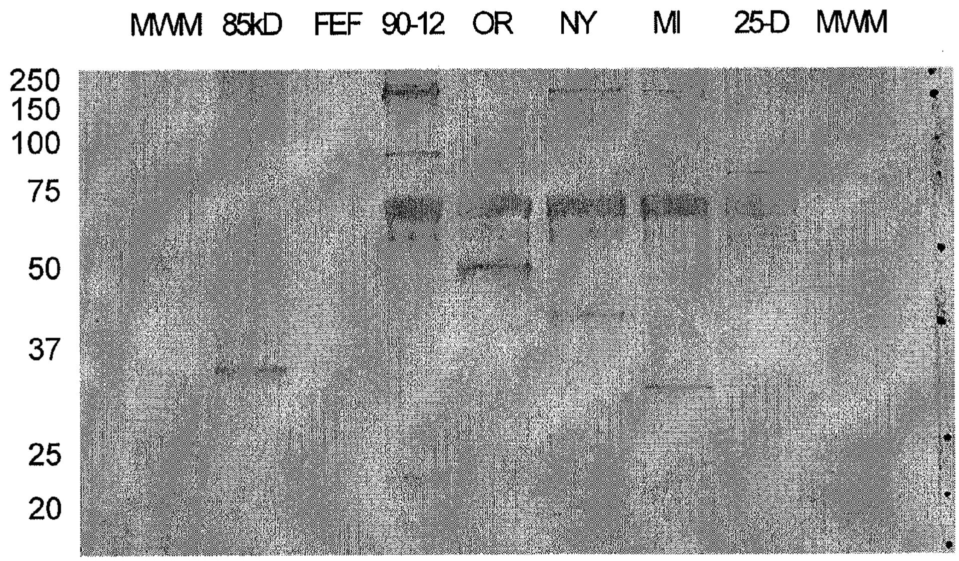
FIG. 2 depicts a Western Blot showing antibody reactivity and antigen banding with horse serum against the recombinant 85 kD SSA of the *N. ristcii* 90-12 strain, FEF cells used to propagate *N. risticii*, and the 90-12, OR, NY, MI and 25-D strains.
Figure 3:
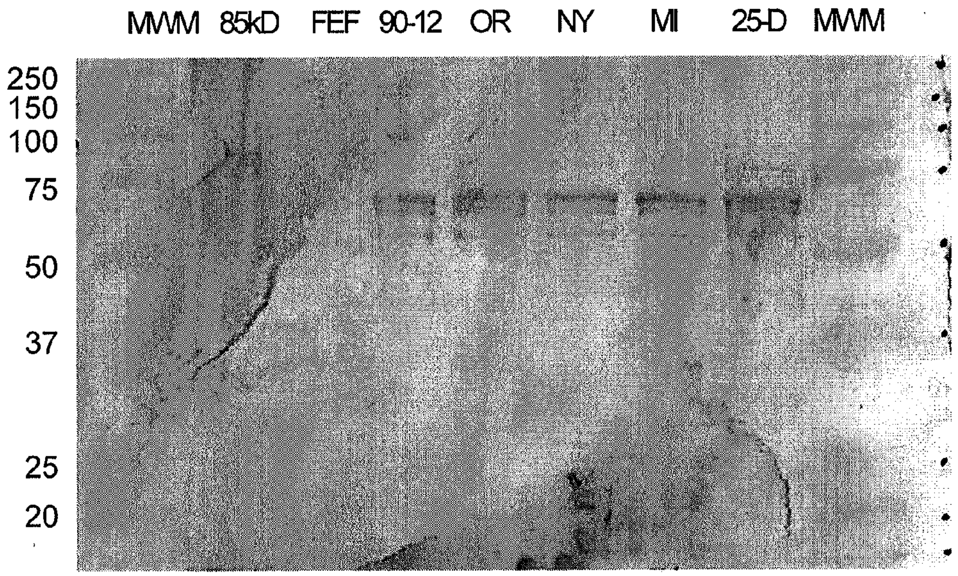
FIG. 3 depicts a Western Blot showing reactivity, or lack thereof, of the same antigens against seronegative horse serum.
Figures 2, 4A:
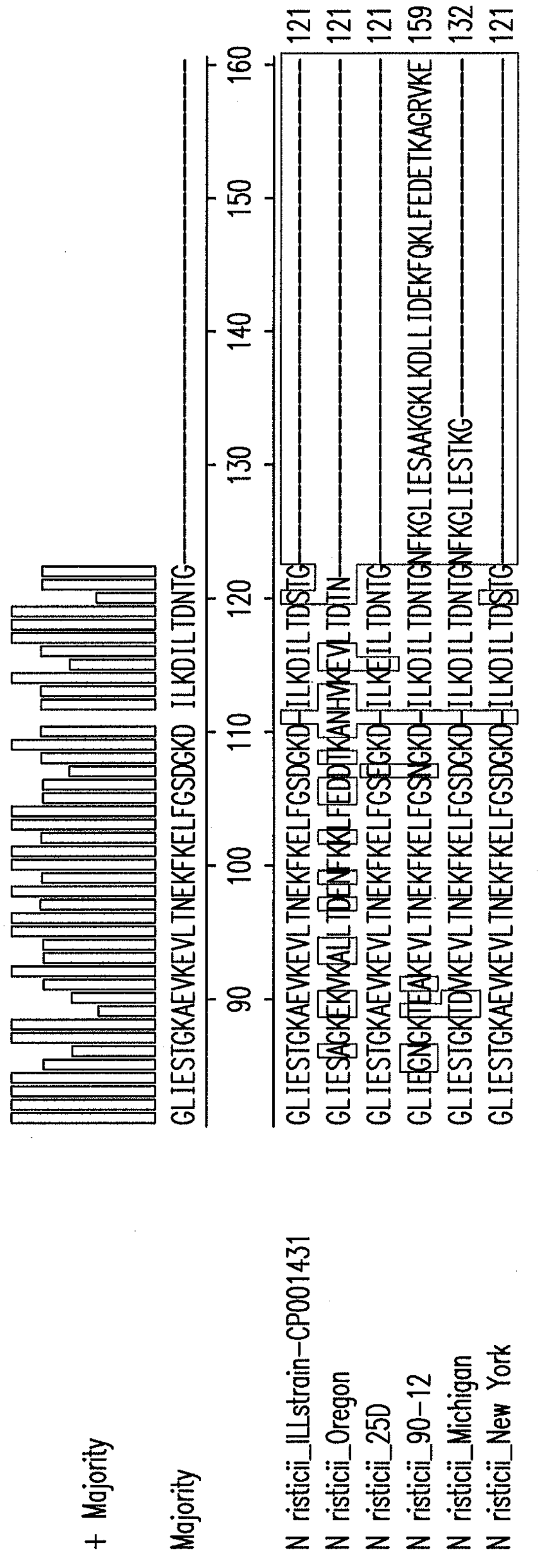
Figures 3, 4A:
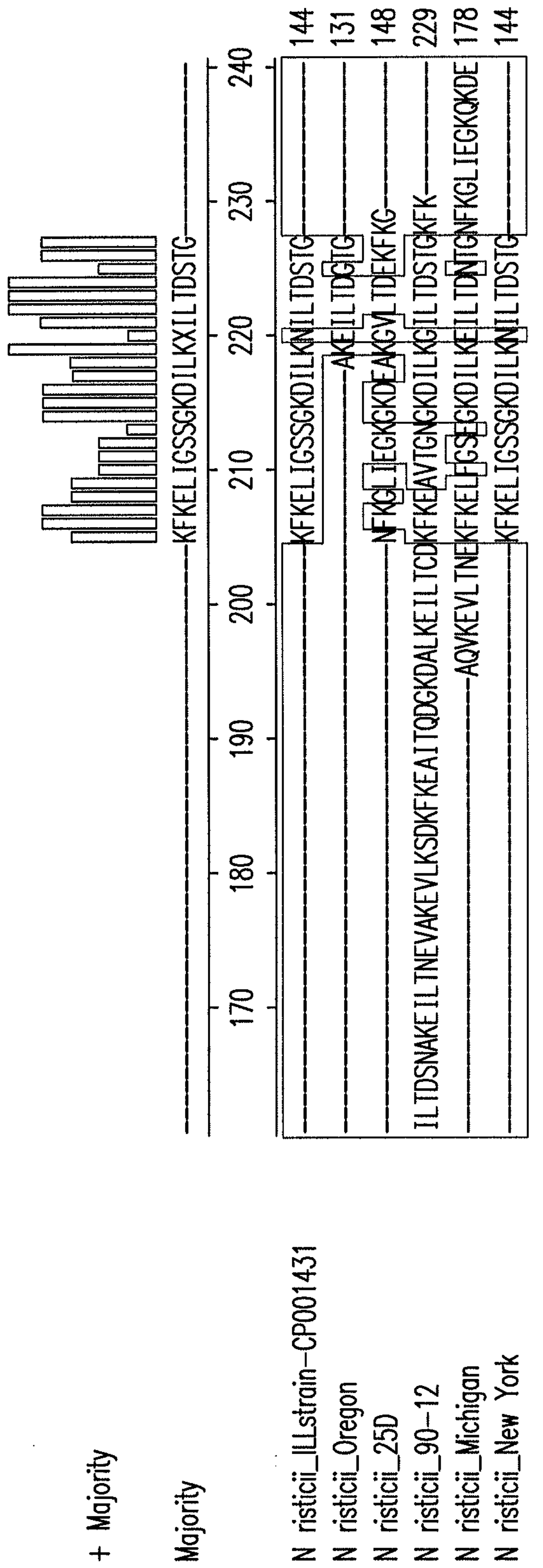
Figures 1, 4B:
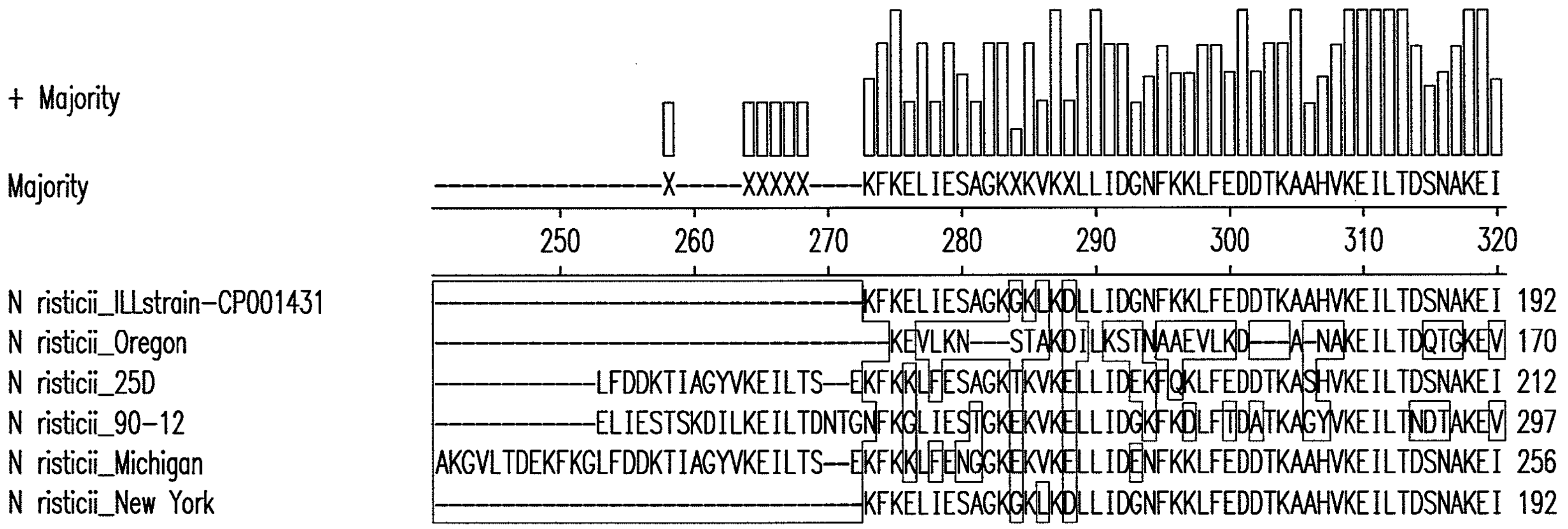
Figures 2, 4B:
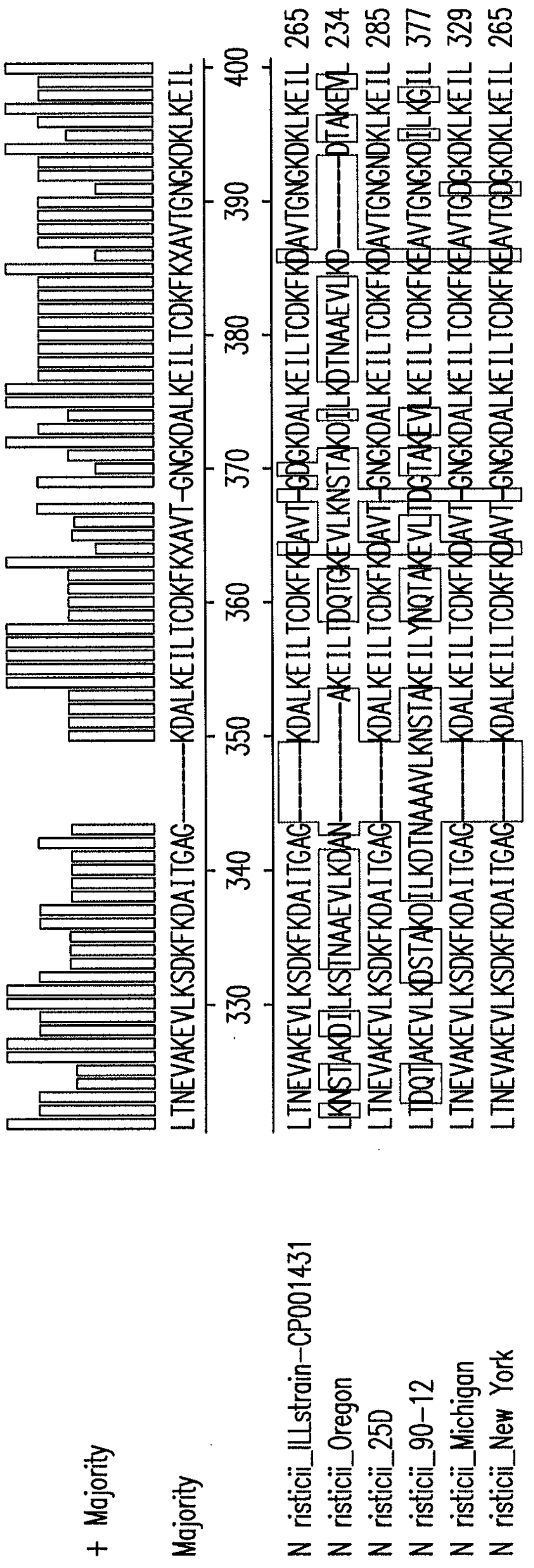
Figures 3, 4B:
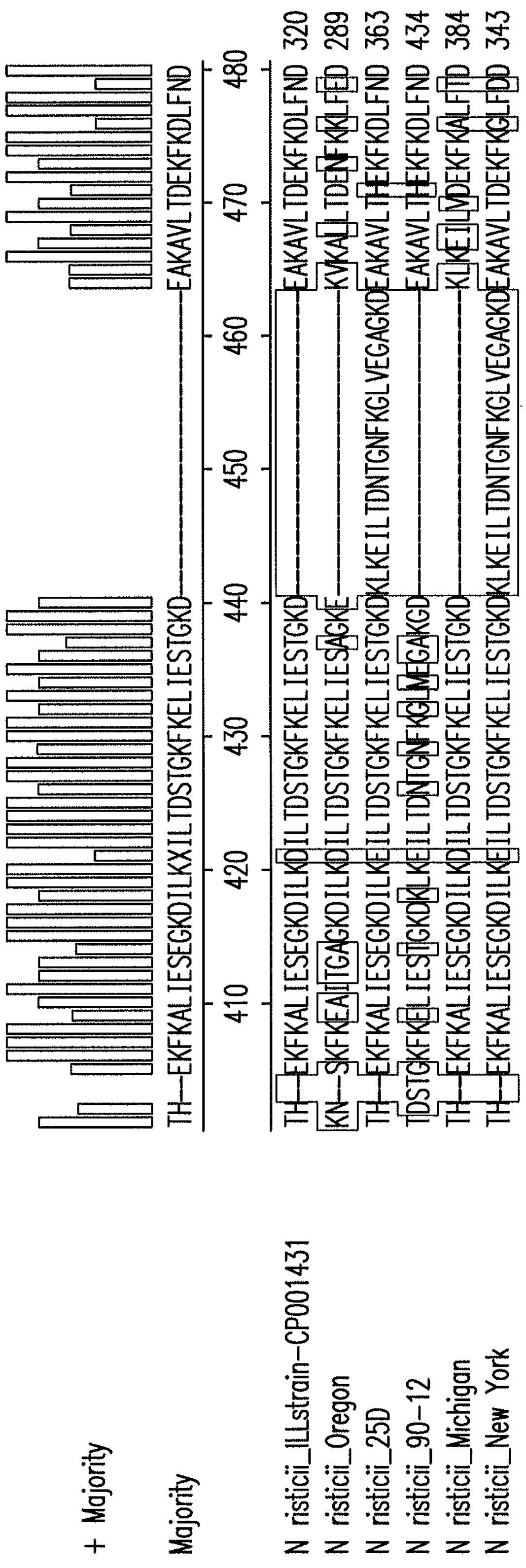
Figures 1, 4C:
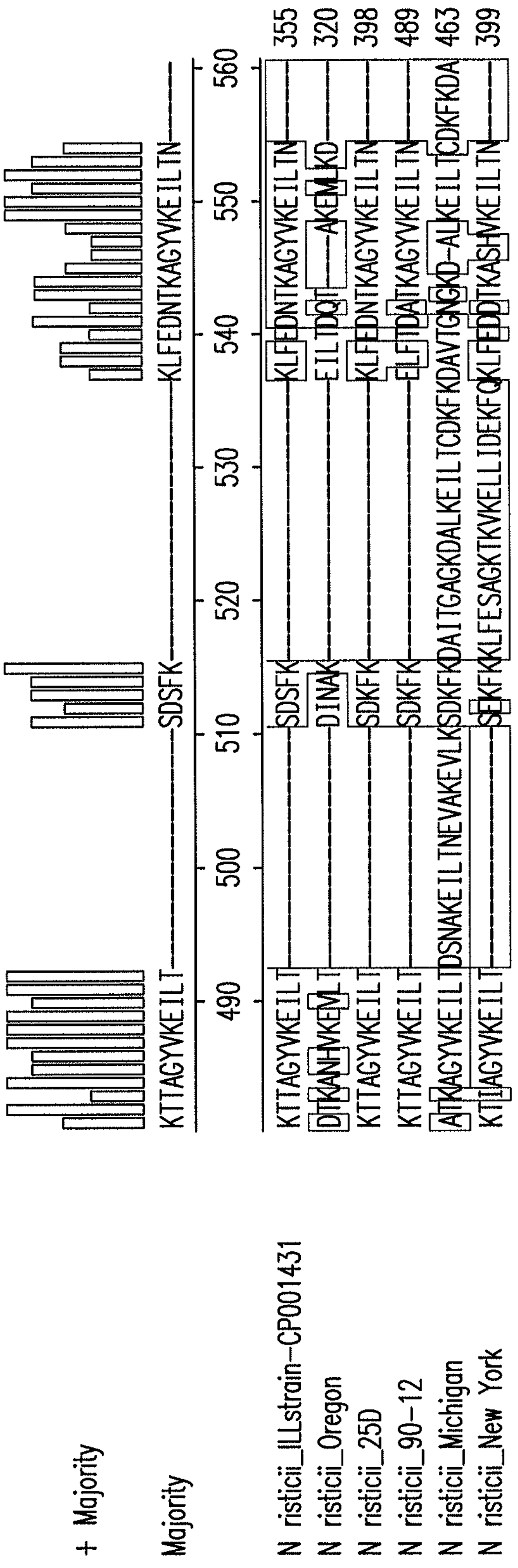
Figures 2, 4C:
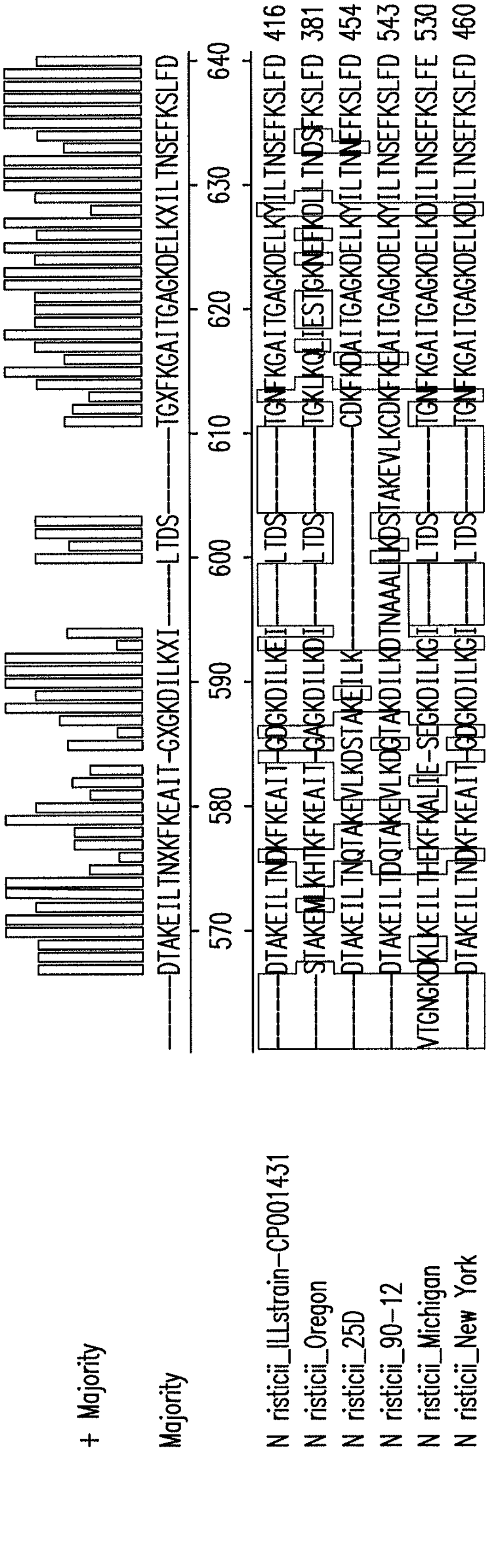
Figures 3, 4C:
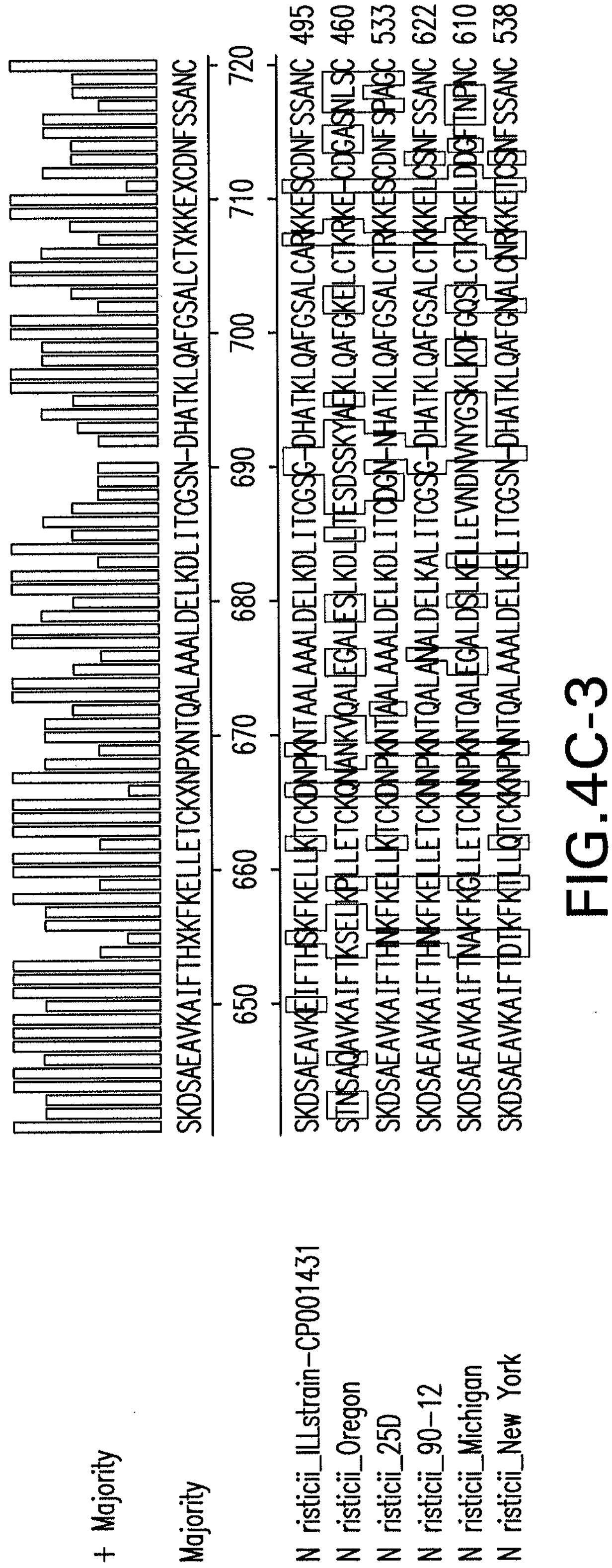
Figure 4D:
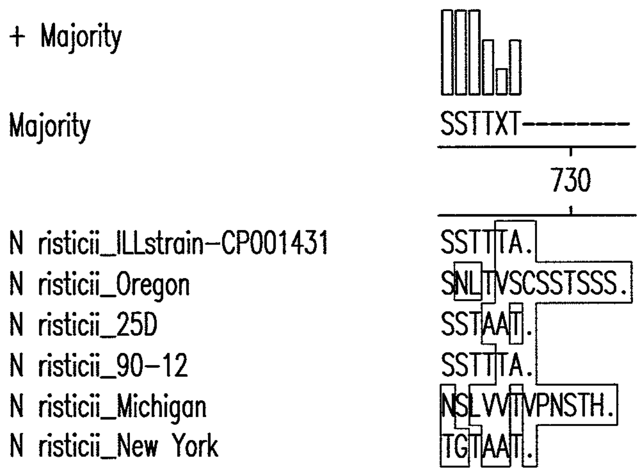
Figures 1, 5B:
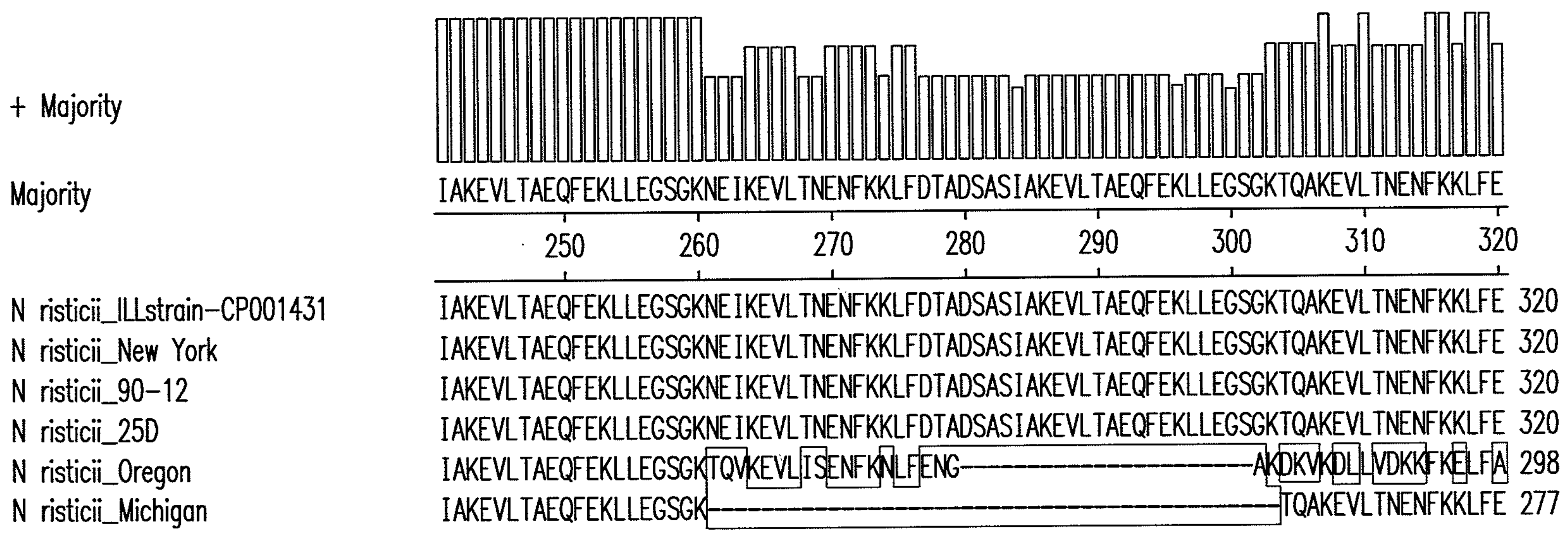
Figures 2, 5B:
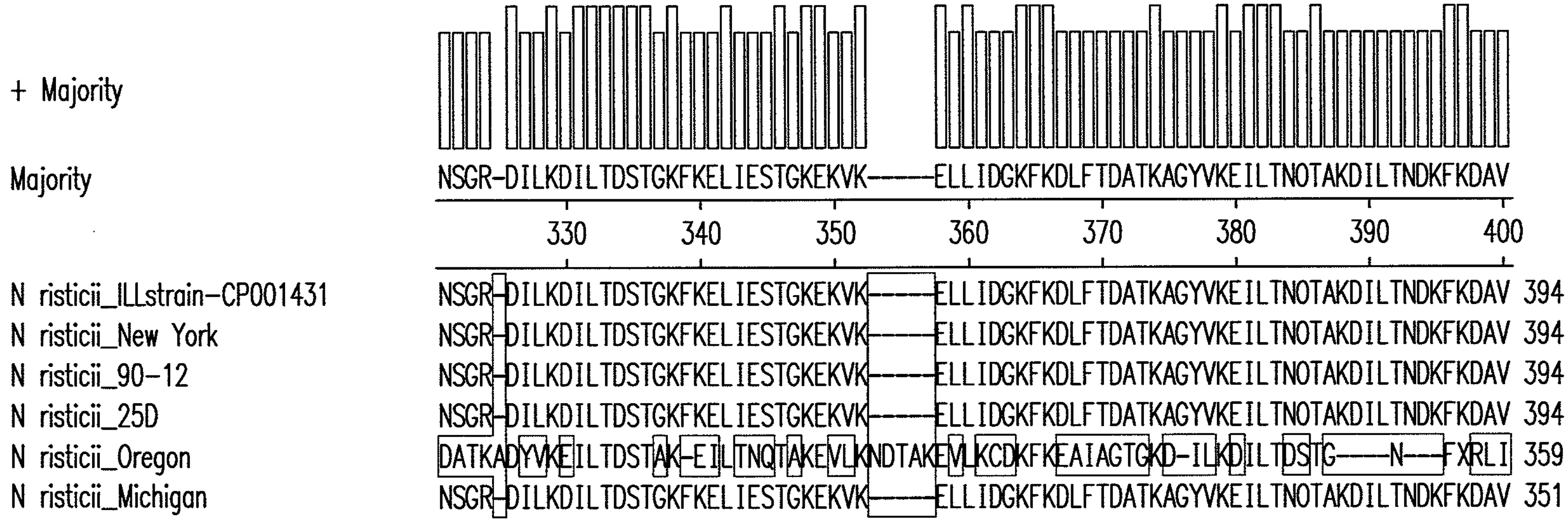
Figures 3, 5B:
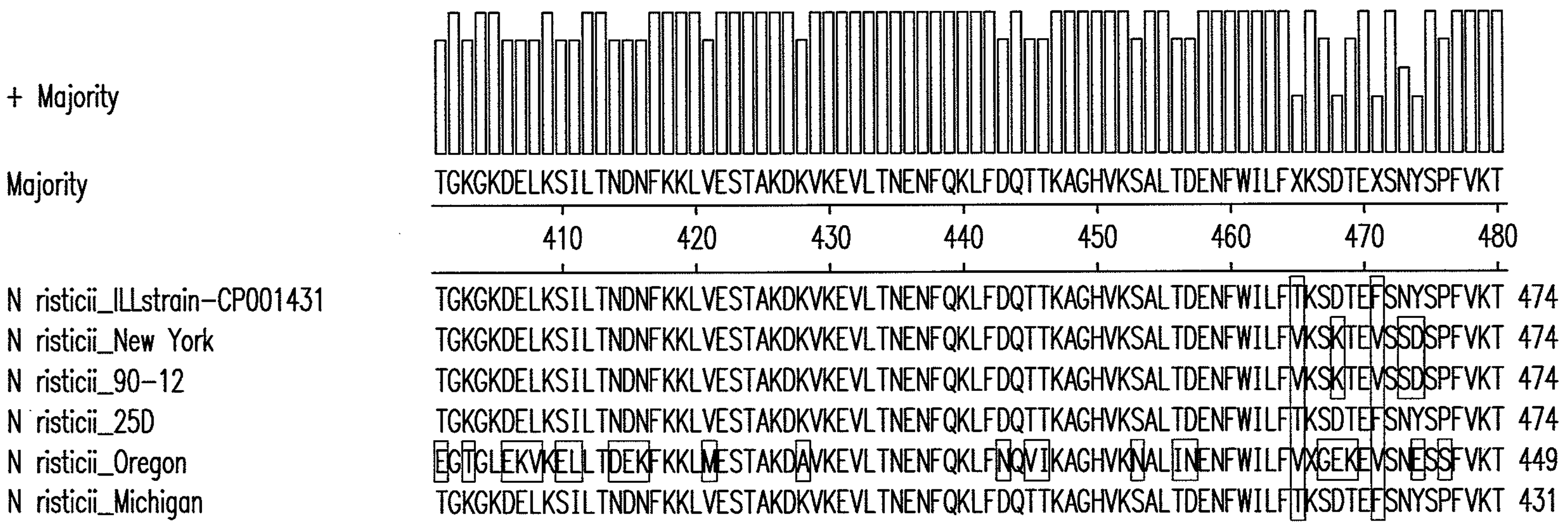
Figures 2, 6A:
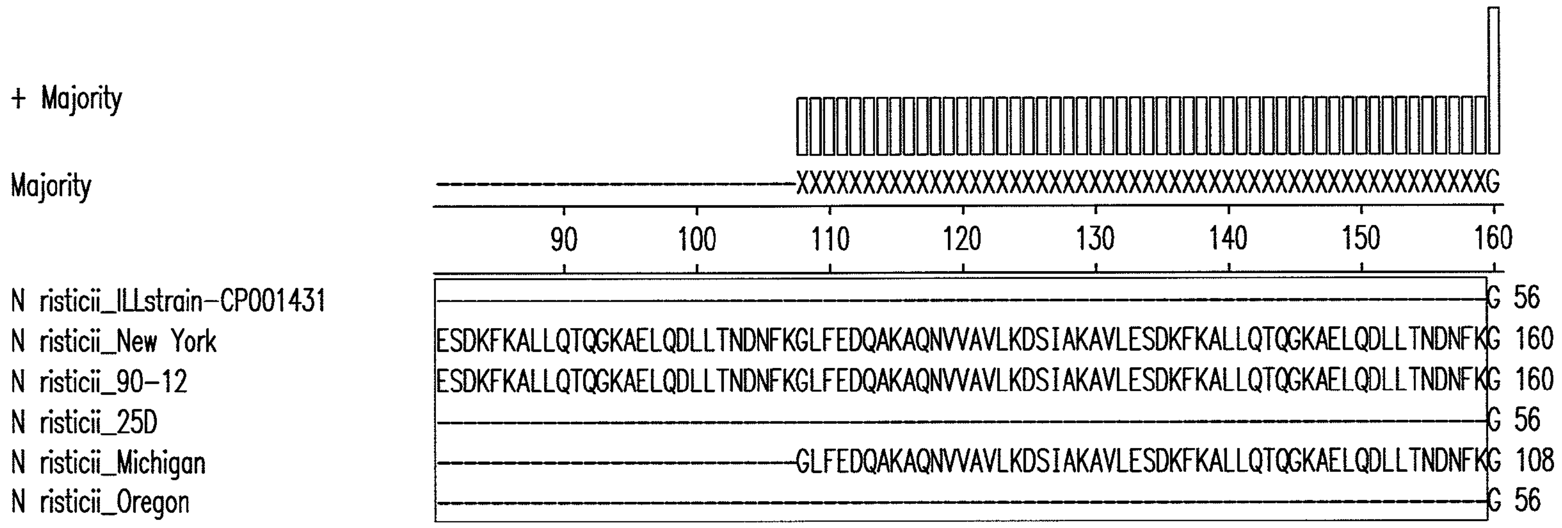
Figures 2, 7B:
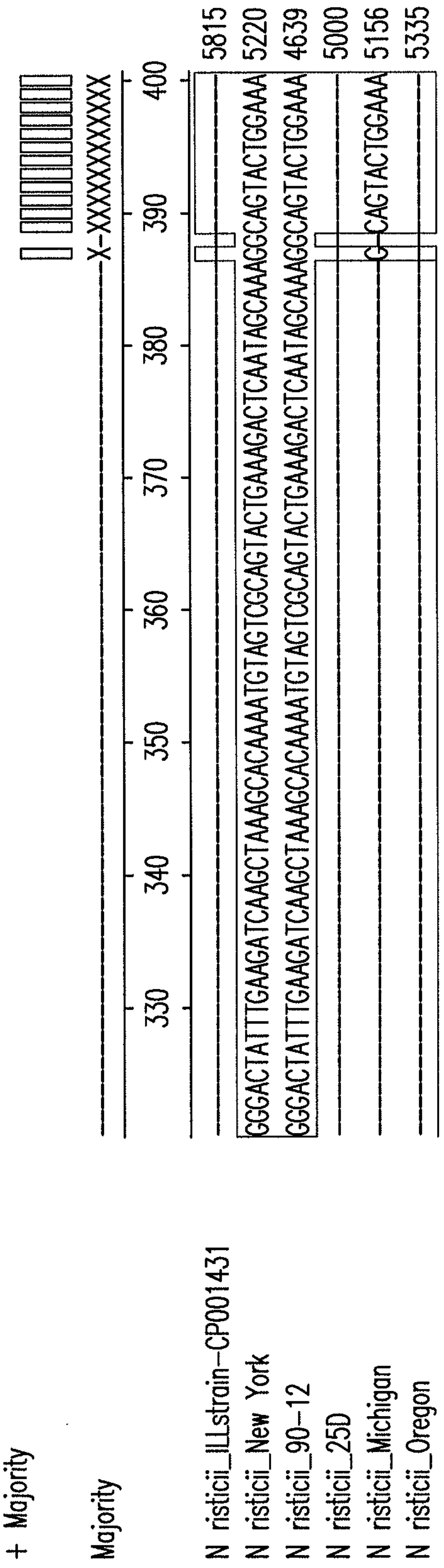
Figures 1, 7C:
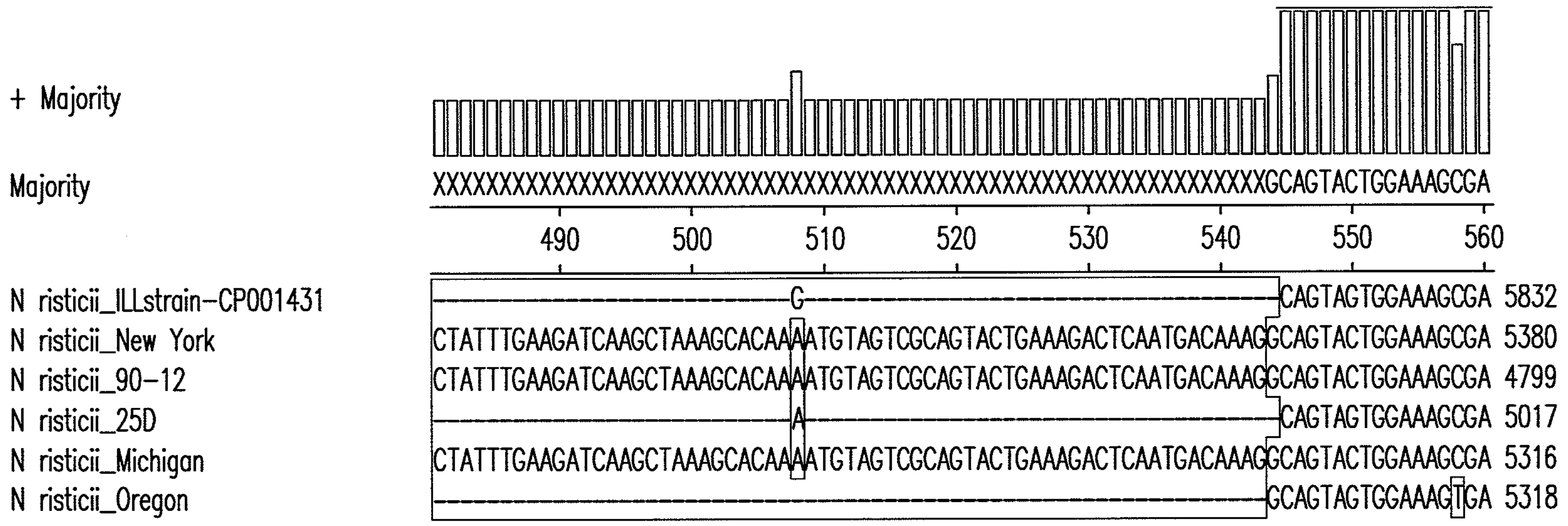
Figures 3, 7D:
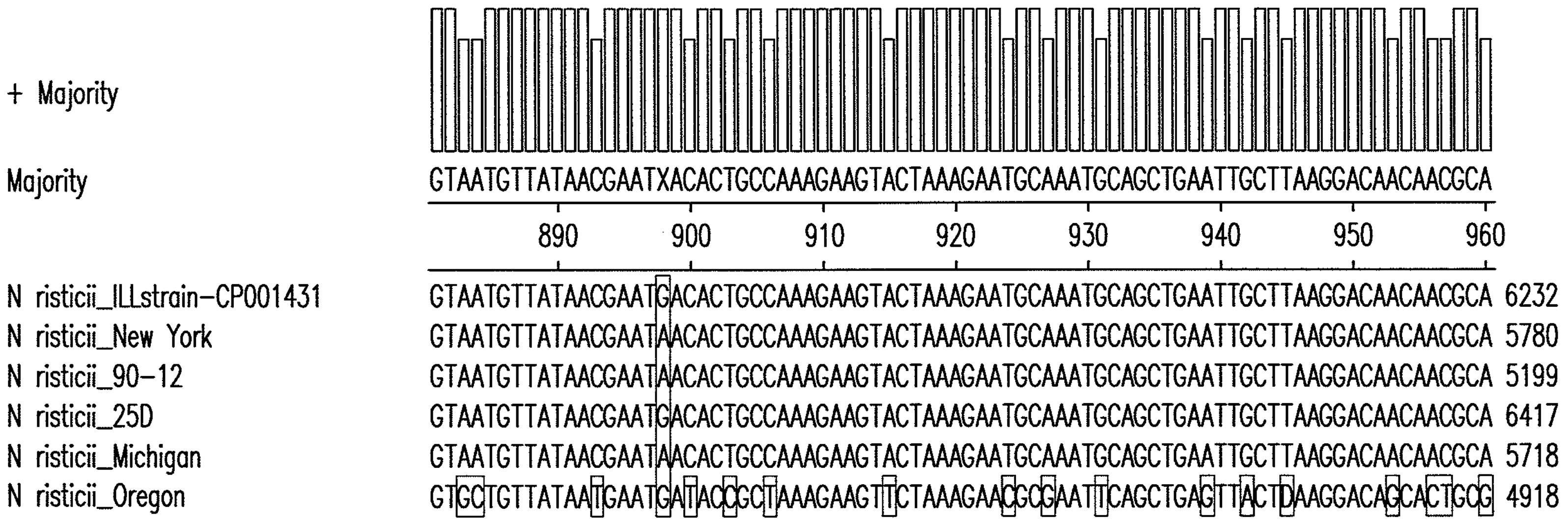
Figures 1, 7E:
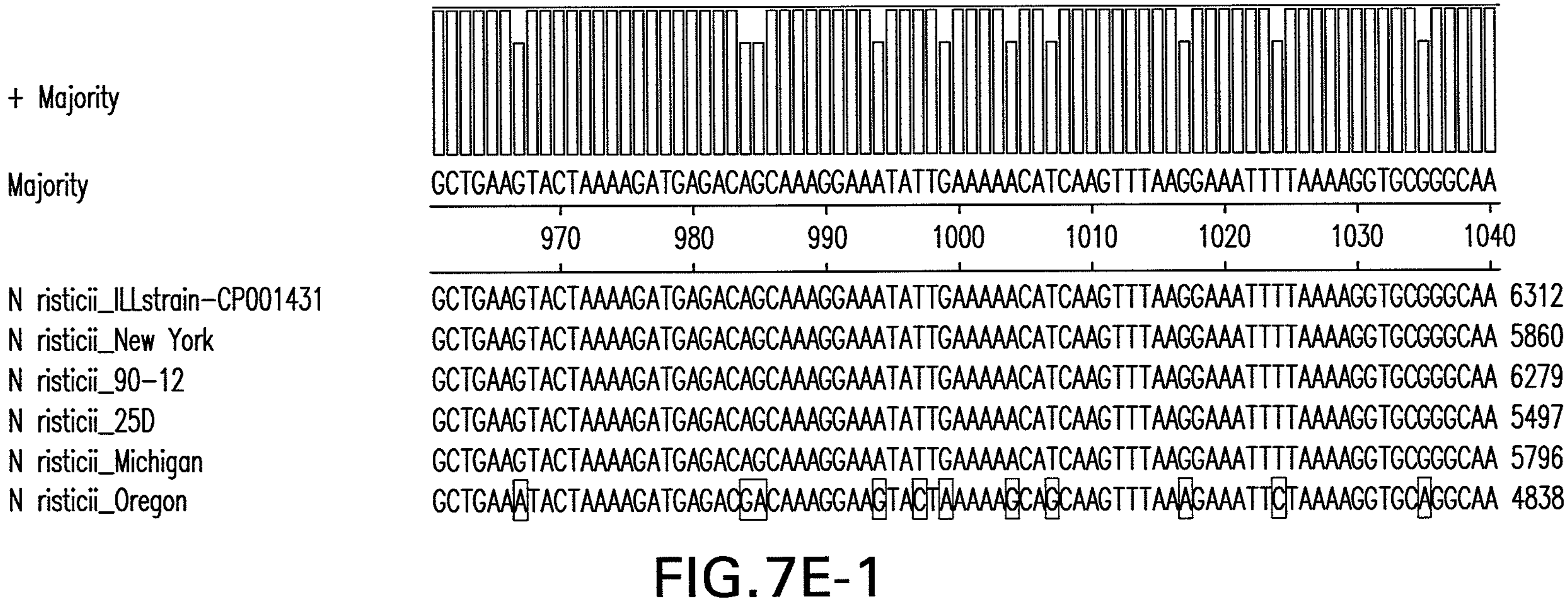
Figures 3, 7G:
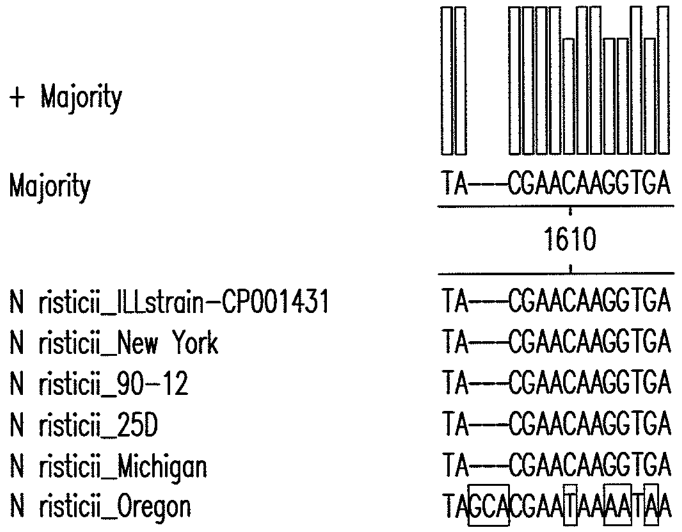

The pooled serum from horses challenged with one of four strains of *N. risticii*, reacted with the recombinant 85 kDa protein at a lower than expected molecular weight of approximately 33 kDa on the Western Blot. (FIG. 2). The predominant unique bands for strain 90-12 of *N. risticii* had molecular weights of approximately 177, 89, and 22 kDa. The serum reacted at differing molecular weight bands of approximately 47 for the OR strain, 180 and 39 kDa for the NY strain, 180 and 31 kDa for the MI strain, and 79 kDa for the 25-D strain of *N. risticii*. No reactions were observed for the FEF cells. These banding patterns indicate that the challenge strains are distinctive and unique.

The bands that appear at the molecular weights of approximately 61-63 kDa and 54-56 kDa of the *N. risticii* strains are non-specific bands that also react with seronegative horse serum.

Example 5

DNA Sequencing Analysis of *N. Risticii* Strains

GeneWiz generated consensus sequences for MAH for the strain specific antigen (SSA) locus of the 90-12, OR, NY, MI and 25-D strains of *N. risticii*. The sequences were analyzed and compared with each other and with the currently published sequences for the *N. risticii* Illinois strain. Both nucleotide sequences and predicted protein sequences were analyzed using the National Center for Biotechnology Information (NCBI) Basic Local Alignment Search Tool (BLAST). In addition, DNASTAR™ LASERGENE MEGALIGN analysis software (version 8.0.2) was used to align and compare sequences with one another.

TABLE 10

| DNA Size comparison: | | | | |
|---|---|---|---|---|
| *N. risticii* Strain | SSA Locus | SSA-1 | SSA-2 | SSA-3 |
| Illinois (acc# CP001431) | ~6600 bp | 1560 bp | 1539 bp | 1302 bp |
| 90-12 | 6356 bp | 1887 bp | 1539 bp | 1614 bp |
| OR | 6871 bp | 1422 bp | 1464 bp | 1305 bp (inverted) |
| NY | 6916 bp | 1638 bp | 1539 bp | 1614 bp |
| MI | 6917 bp | 1869 bp | 1410 bp | 1458 bp |
| 25-D | 6620 bp | 1620 bp | 1539 bp | 1302 bp |

The BLAST results differ slightly from those obtained using the DNASTAR™ LASERGENE MEGALIGN program, which indicates that the NY strain shares the highest identity with the published Illinois strain. MEGALIGN software uses the CLUSTALW, SLOW ACCURATE algorithm for aligning multiple sequences (FIGS. 4-7), while the NCBI BLAST search uses the BLASTN and BLASTP algorithms (TABLE 11). In FIG. 7 the nucleic acid sequence for OR SSA#3 is the reversed complimentary sequence from the wild type sequence in order to match it with the genes of the compared *N. risticii* strains.

TABLE 11

| BLAST Analysis Results Summary: | | | |
|---|---|---|---|
| Strain | Portion analyzed | Top Blast Hit (% identity) | Genebank Accession No. |
| 90-12 | whole fragment (DNA) | 92.5% to Illinois (94% to 90-12: 85 kd)* | CP00143 |
| | SSA1 (amino acid sequence) | 82.5% to 90-12: 85 kd | AAC31428 |
| | SSA2 (amino acid sequence) | 99.0% to Illinois (37% to 90-12: 85 kd) | YP_0030 |
| | SSA3 (amino acid sequence) | 94.2% to Illinois | YP_0030 |
| OR | whole fragment (DNA) | 87.3% to Illinois | CP00143A |
| | SSA1 (amino acid sequence) | 52.6% to Illinois | YP_0030 |
| | SSA2 (amino acid sequence) | 63.5% to Illinois | YP_0030 |
| | SSA3 (amino acid sequence) | 88.1% to Illinois | YP_0030 |
| NY | whole fragment (DNA) | 94.0% to Illinois | CP00143 |
| | SSA1 (amino acid sequence) | 86.3% to Illinois | YP_0030 |
| | SSA2 (amino acid sequence) | 98.8% to Illinois | YP_0030 |
| | SSA3 (amino acid sequence) | 94.2% to Illinois | YP_0030 |
| MI | whole fragment (DNA) | 97.0% to Illinois | CP00143 |
| | SSA1 (amino acid sequence) | 69.0% to 25-D: 50 kd (67% to Illinois) | AAC31427 |
| | SSA2 (amino acid sequence) | 90.9% to Illinois | YP_0030 |
| | SSA3 (amino acid sequence) | 85.6% to Illinois | YP_0030 |
| 25-D | whole fragment (DNA) | 96.3% to Illinois | CP00143A |
| | SSA1 (amino acid sequence) | 98.0% to 25-D: 50 kd | AAC31427 |
| | SSA2 (amino acid sequence) | 99.8% to Illinois | YP_0030 |
| | ssa3 (amino acid seq.) | 99.8% to Illinois | YP_0030 |

*Accession AF059673 (strain 90-12) 85 kd SSA gene nucleotide sequence is smaller than whole fragment sequenced.

Biological Deposit

Cultures of the following biological materials have been deposited with the following international depository: American Type Culture Collection (ATCC) 10801 University Boulevard, Manassas, Va. 20110-2209, U.S.A., under conditions that satisfy the requirements of the Budapest Treaty.

| Organism | Accession No. | Date of Deposit |
|---|---|---|
| *Neorickettsia risticii* Oregon | PTA-11232 | Jul. 27, 2010 |
| *Neorickettsia risticii* New York | PTA-11231 | Jul. 27, 2010 |
| *Neorickettsia risticii* Michigan | PTA-11404 | Oct. 13, 2010 |

| SEQUENCE LISTING TABLE | | | |
|---|---|---|---|
| SEQ ID NO: | STRAIN | SS# | Type |
| 1 | Illinois | 1 | AA |
| 2 | Oregon | 1 | AA |
| 3 | 25-D | 1 | AA |
| 4 | 90-12 | 1 | AA |
| 5 | Michigan | 1 | AA |
| 6 | New York | 1 | AA |
| 7 | Illinois | 2 | AA |
| 8 | New York | 2 | AA |
| 9 | 90-12 | 2 | AA |
| 10 | 25-D | 2 | AA |
| 11 | Oregon | 2 | AA |
| 12 | Michigan | 2 | AA |
| 13 | Illinois | 3 | AA |
| 14 | New York | 3 | AA |
| 15 | 90-12 | 3 | AA |
| 16 | 25-D | 3 | AA |
| 17 | Michigan | 3 | AA |
| 18 | Oregon | 3 | AA |
| 19 | Illinois | 3 | NA |
| 20 | New York | 3 | NA |
| 21 | 90-12 | 3 | NA |
| 22 | 25-D | 3 | NA |
| 23 | Michigan | 3 | NA |
| 24 | Oregon | 3 | NA |
| 25 | Oregon | 1 | NA |
| 26 | Oregon | 2 | NA |
| 27 | New York | 1 | NA |
| 28 | New York | 2 | NA |
| 29 | Michigan | 1 | NA |
| 30 | Michigan | 2 | NA |
| 31 | Illinois | 1 | NA |
| 32 | Illinois | 2 | NA |
| 33 | 25-D | 1 | NA |
| 34 | 25-D | 2 | NA |
| 35 | 90-12 | 1 | NA |
| 36 | 90-12 | 2 | NA |

AA is an amino acid sequence;

NA is a nucleic acid sequence.

It is to be understood that all base sizes or amino acid sizes, and all molecular weight or molecular mass values, provided to describe nucleic acids and polypeptides according to the invention are approximate within conventional measurement variations.

We claim:

1. A composition comprising a *N. risticii* Michigan isolate having the ATCC deposit number PTA-11404; wherein the *N. risticii* is killed or inactivated.

2. The composition of claim 1 wherein the *N. risticii* is killed or inactivated by a method selected from the group comprising sonication, freeze-thaw techniques, pressure, treatment with heat, a chemical and an enzyme.

3. The composition of claim 2 wherein the chemical is selected from the group consisting of binary ethyleneimine and formalin.

* * * * *